US012806397B2

(12) United States Patent
Forrester

(10) Patent No.: US 12,806,397 B2
(45) Date of Patent: Nov. 24, 2026

(54) HEATED RESPIRATORY HOSE SUPPORT HELIX INCORPORATING LUMENS

(71) Applicant: GLOBALMED, INC., Trenton (CA)

(72) Inventor: Martin E Forrester, Trenton (CA)

(73) Assignee: GLOBALMED, INC., Trenton (CA)

( * ) Notice: Subject to any disclaimer, the term of this patent is extended or adjusted under 35 U.S.C. 154(b) by 436 days.

(21) Appl. No.: 18/536,950

(22) Filed: Dec. 12, 2023

(65) Prior Publication Data

US 2024/0115847 A1 Apr. 11, 2024

Related U.S. Application Data

(63) Continuation-in-part of application No. 16/920,718, filed on Jul. 5, 2020, now Pat. No. 11,839,719, which (Continued)

(51) Int. Cl.
*A61M 39/08* (2006.01)
*A61M 16/00* (2006.01)

(Continued)

(52) U.S. Cl.
CPC ........ *A61M 39/08* (2013.01); *A61M 16/0003* (2014.02); *B29C 48/0021* (2019.02);

(Continued)

(58) Field of Classification Search
CPC .............. A61M 39/08; A61M 16/0003; A61M 16/0883; A61M 2016/0039; A61M 2205/3334; A61M 2205/3368; A61M 2205/3633; A61M 2205/3653; A61M 2207/00; A61M 2207/10; A61M 16/0875; A61M 16/1095; A61M 16/0833; A61M 16/0051; A61M 16/024; B29C 48/0021; B29C 48/131; B29C 53/582; B29C 53/586; B29C 53/62; B29C 53/78; B29C 53/827;

(Continued)

(56) References Cited

U.S. PATENT DOCUMENTS 4,510,004 A * 4/1985 Hawerkamp ....... B29C 53/8016 156/143
6,367,510 B1 * 4/2002 Carlson .................. F16L 11/118 138/121

(Continued)

*Primary Examiner* — Jeffrey M Wollschlager
(74) *Attorney, Agent, or Firm* — Benjamin D. Burge Co., LLC

(57) ABSTRACT

A method includes: extruding a continuous web of plastics material from an extruder of a hose making apparatus; helically winding the extruded web about a mandrel or at least one rotating rod of the hose making apparatus to form a wall of the hose about a central axis of the hose; extruding a continuous bead of plastics material to have a cross-section that defines a lumen at a location within the cross-section; cooling the extruded bead sufficiently to cool the plastics material adjacent the location within the cross-section of the extruded bead to cause the lumen to retain its size and shape within the cross-section; re-heating the extruded bead sufficiently to cause outer surface portions of the plastics material of the extruded bead to become molten; and helically winding the extruded bead onto and about an external surface of the wall to provide the wall a support helix.

16 Claims, 51 Drawing Sheets

Related U.S. Application Data is a continuation-in-part of application No. 16/506,989, filed on Jul. 9, 2019, now Pat. No. 11,813,403, which is a continuation-in-part of application No. 15/882,257, filed on Jan. 29, 2018, now Pat. No. 11,052,214.

(60) Provisional application No. 62/499,623, filed on Jan. 30, 2017.

(51) Int. Cl.

| | |
|---|---|
| ***B29C 48/00*** | (2019.01) |
| ***B29C 48/03*** | (2019.01) |
| ***B29C 53/58*** | (2006.01) |
| ***B29C 53/62*** | (2006.01) |
| ***B29C 53/78*** | (2006.01) |
| ***B29C 53/82*** | (2006.01) |
| ***B29C 65/02*** | (2006.01) |
| ***B29L 23/00*** | (2006.01) |

(52) U.S. Cl.
CPC .......... *B29C 48/131* (2019.02); *B29C 53/582* (2013.01); *B29C 53/586* (2013.01); *B29C 53/62* (2013.01); *B29C 53/78* (2013.01); *B29C 53/827* (2013.01); *B29C 65/02* (2013.01); *B29L 2023/007* (2013.01)

(58) Field of Classification Search
CPC ......... B29C 65/02; B29C 48/08; B29C 48/09; B29C 48/13; B29C 48/154; B29C 53/583; B29L 2023/007; B29D 23/00
See application file for complete search history.

(56) References Cited

U.S. PATENT DOCUMENTS

| | | | | |
|---|---|---|---|---|
| 6,932,119 | B2 * | 8/2005 | Carlson | B29C 53/585 138/121 |
| 9,717,874 | B2 * | 8/2017 | Smith | B29C 66/112 |
| 2020/0398014 | A1 * | 12/2020 | Petrochenko | A61M 16/0833 |
| 2021/0077765 | A1 * | 3/2021 | Peiris | A61M 16/161 |

* cited by examiner

HEATED RESPIRATORY HOSE SUPPORT HELIX INCORPORATING LUMENS

REFERENCE TO RELATED APPLICATIONS

This Utility Patent Application is a continuation-in-part of U.S. patent application Ser. No. 16/920,718 filed Jul. 5, 2020; which is a continuation-in-part of U.S. patent application Ser. No. 16/506,989 filed Jul. 9, 2019 (since issued as U.S. Pat. No. 11,813,403); which is a continuation-in-part of U.S. patent application Ser. No. 15/882,257 filed Jan. 29, 2018 (since issued as U.S. Pat. No. 11,052,214); which claims the benefit of the filing date of U.S. Provisional Application Ser. No. 62/499,623 filed Jan. 30, 2017; the disclosures of all of which are incorporated herein by reference in their respective entireties for all purposes.

BACKGROUND

The present invention relates to the field of hoses to convey respiratory gases to and from patients as part of treating various medical conditions, such as traumatic lung injury, sleep apnea, asthma, chronic obstructive pulmonary disease (COPD), hypoxemia and hypotension. Such hoses may be incorporated into assemblies of used to convey respiratory gases between a medical device, such as a ventilator or continuous positive airway pressure (CPAP) device, and a face mask, an endotracheal tube or tracheostomy stoma of a patient. Such equipment may be used in a hospital or other medical facility, or may be used at a patient's home, such as at a patient's bedside while sleeping.

It is usually deemed desirable for such gases conveyed to a patient include some degree of water vapor to avoid drying tissues of a patient's respiratory system. Also, the respiratory gases that a patient breathes out also typically include some amount of water vapor. An issue arising from the water vapor in the respiratory gases conveyed both to and from a patient is that of condensation within the hoses. If the temperature of the gases in one of the hoses falls below the dew point of the gases within that hose, then water vapor condenses within that hose, and possibly leads to pooling of liquid water within the lowest portion of the hose. As a result, the flow of gases through that hose may be constricted or even cut off entirely in a manner very much akin to the pooling of water within a sink drain trap. Alternatively or additionally, depending on where such pooling occurs within a hose, it is possible for a patient to be caused to breathe in pooled water from within a hose and/or for pooled water within a hose to be sent into the medical device. Such developments may be acutely and immediately harmful to the patient such that the patient may be caused to actually drown from inhalation of liquid water into the lungs, and/or the medical device may be damaged by the intake of liquid water, instead of gases breathed out by the patient.

Among prior art efforts to address such issues is the addition of water traps to each such hose. A water trap serves, in essence, as a designated location along the length of a hose where liquid water can be allowed to pool relatively harmlessly out of the path of flow of gases through the hose to at least minimize any possible obstruction to the passage of gases through the hose. Unfortunately, the use of water traps suffers various drawbacks. For a water trap to work effectively, it must be positioned at a point along its respective hose that is lowest in elevation such that any liquid water that is caused to condense from the respiratory gases is caused by the force of gravity to proceed toward the water trap, instead of pooling elsewhere within the hose. This requires some deliberate effort on the part of those who use such hoses and caregivers who prepare such hoses for use to ensure that the manner in which such hoses are installed and used does indeed result in the water traps being at the point of lowest elevation along the hoses. However, even if this is successful, each of the water traps holds a finite volume of liquid, and is therefore required to be opened and emptied on a regular basis to prevent overfilling. Also of concern is the possibility of the liquid within a water trap collecting and growing pathogens that may then propagate into the respiratory gases passing through the hoses, and thereby potentially infect the patient.

Another prior art effort to address such issues is to lay heating wires inside each of such hoses to raise the temperature of the gases therein to be higher than the dew point, thereby avoiding the occurrence of condensation altogether. Unfortunately, it has been found that simply laying heating wires within a hose results in uneven heating of the gases therein, thereby possibly leaving portions of the hose with a temperature that is still low enough relative to the dew point of the gases therein to allow condensation to occur.

Other issues exist in prior art heated respiratory hose assemblies beyond that of condensation. The heating of such assemblies often entails the use of a temperature sensor that must be inserted at the correct location among the circulatory flow of gases to and from the patient to be effective. Also, many medical devices also employ a gas flow sensor to provide continual confirmation of there being a flow of respiratory gases from the medical device to the patient, and this sensor must also be positioned at the correct location among the circulatory flow of gases to and from the patient to be effective. Unfortunately, many prior art heated respiratory hose assemblies use numerous individual fittings to connect the lengths of hose together to form the assembly, and to connect the assembly to both the medical device and the face mask, endotracheal tube or tracheostomy stoma at the patient end of the assembly. These numerous fittings often include separate fittings for the locations of the flow and temperature sensors, thereby providing opportunities for errors to occur in the connection and placement of these sensors.

SUMMARY

The present invention addresses such needs and deficiencies as are explained above by providing a heated respiratory hose assembly that includes a pair of heated hoses and various fittings to convey respiratory gases in a closed circuit between a medical device, such as a ventilator or CPAP device, and a patient. Such a hose assembly may be used in a medical environment, such as a hospital, outpatient care facility or other medical facility, or a non-medical environment, such as a patient's home or workplace. Such a hose assembly may incorporate a relatively minimal set of components to reduce opportunities for errors in assembling those components, as well as connecting various sensors thereto, as part of preparing the hose assembly for use.

Each hose of the heated respiratory hose assembly may incorporate electrical wires into its support helix, which may include heating wires to enable even distribution of the heat generated by the heating wires within the interior of the hose. Such heating wires may be positioned within the support helix at a location closer to the interior of the hose and in a manner that uses much of the material of the support helix as an insulator against the environment external to the hose to cause a greater proportion of the heat generated by the heating wires to radiated into the interior of the hose, rather than wastefully radiated into the environment external to the hose. To achieve such placement, a bead of plastics material that forms the support helix may be extruded around the heating wires as the heating wires are fed through the extruder that extrudes the bead of plastics material during formation of the hose. Additionally, tension may be exerted on the heating wires during formation of the hose to cause the heating wires to be drawn through plastics material of the bead, while still molten, and closer to the interior of the hose.

In other embodiments, the bead of plastics material that forms the support helix may be more fully formed at a stage that precedes the formation of the wall of the hose such that the heating and/or other electrical wires may already be positioned as desired within the support helix before the support helix is combined with the one or more extrusions used to form the wall. More specifically, the bead of plastics material may be extruded around the heating and/or other electrical wires as those wires are fed through the extruder that extrudes the bead. However, instead of directly winding the newly formed bead around the wall of the hose, the newly formed bead may be routed through a trough of water (or other cooling device) to cool the plastics material of the newly formed bead enough to cause the plastics material to be hardened enough to prevent the heating and/or other electrical wires from migrating within the plastics material. In this way, the cross-section of the newly formed bead is stabilized such that the position of the heating and/or other electrical wires therein is set.

Following such cooling, the newly formed and cooled bead may then be fed through a heating tube in which the bead is re-heated to a controlled degree that causes outer surface portions thereof to slightly molten such that the outer surface portions are softened and become tacky, while avoiding heating the bead to such an extent that inner portions thereof are also caused to become molten such that the heating and/or other electrical wires therein are caused to be able to migrate to new positions therein. By softening the outer surface portions, the now re-heated bead is now less resistant to being wrapped around the exterior of the wall of a hose. By making the outer surface portions tacky, the now re-heated bead is caused to readily bond to the exterior wall of the hose as it is wrapped around the exterior wall of the hose, thereby becoming the support helix of the heated hose and completing the formation of the heated hose.

Alternatively, following such cooling, the newly formed and cooled bead may, instead of being immediately re-heated and used as the support helix in the formation of a heated hose, be stored in a roll (e.g., wound on a spindle, etc.) for storage for later use in the formation of a heated hose at a later time. It may be deemed desirable to store rolls of multiple types of beads, each having a different external cross-sectional shape, and/or a different assortment of heating and/or other electrical wires formed therein, and/or with different positional arrangements of heating and/or other electrical wires therein. Such storage of such a variety of beads may enable the on-demand or just-in-time manufacturing of heated hoses where the type of bead to be included is able to be selected from among such a variety for each heated hose that is to be made.

Regardless of whether the newly formed and cooled bead is used immediately in forming a heated hose or stored for later use in forming a heated hose, in some embodiments, the re-heating of the outer surface portions of the newly formed and cooled bead may entail feeding the newly formed and cooled bead through a heating tube into which hot air is blown. The temperature and/or volume of the hot air blown into the heating tube may be adjusted to control the degree to which outer surface portions of the bead are caused to become molten. Such hot air temperature and/or volume control may be based on various factors, including and not limited to, the cross-section of the heating tube, the cross-section of the bead, the length of the heating tube and/or the speed at which the bead is fed through the heating tube.

Each hose of the heated respiratory hose assembly may incorporate a pair of hose fittings, one at each end of each hose. Each such hose fitting may be formed of rigid plastics material and may be shaped and sized to enable connection of its corresponding end of a hose to a medical device or to a face mask, endotracheal tube, tracheostomy stoma or other component worn by or otherwise carried by a patient, and may do so directly or through at least one other component interposed therebetween. Each such hose fitting may be permanently coupled to its corresponding end of a hose by an undermold coupling formed of flexible plastics material to provide a gas-tight seal between the fitting and its corresponding end of the hose, and/or to provide a strain relief to prevent damage to the hose where the end of the hose is coupled to its corresponding fitting.

Each undermold coupling may be formed as a single piece of the flexible plastics material, and may include a generally cylindrical tubular portion and at least one ladder-like grating. Threads may be formed on the interior surface of the cylindrical tubular portion to enable the cylindrical tubular portion to be threaded onto the exterior of an end of a hose as part of coupling the undermold coupling to an end of a hose. Each hose fitting may be formed as a single piece of the rigid plastics material, and may include a generally cylindrical tubular portion. The cylindrical tubular portion may have a slightly larger diameter than the cylindrical tubular portion of its corresponding undermold coupling to receive and closely surround the cylindrical tubular portion of its corresponding undermold coupling therein.

A set of slots may be formed through a portion of the cylindrical wall of the cylindrical tubular portion of each hose fitting to interact with the at least one ladder-like grating of the corresponding undermold coupling as part of forming a permanent mechanical coupling between the fitting and the corresponding undermold coupling. As the cylindrical tubular portion of an undermold coupling is received within the cylindrical tubular portion of a hose fitting, a ladder-like grating of the undermold coupling may be hinged or may be otherwise partly pulled away from contact with the exterior of the cylindrical tubular portion of the undermold coupling to allow portions of the ladder-like grating to be positioned to overlie, and then extend into and through the slots formed through the cylindrical wall of the cylindrical tubular portion of the hose fitting. In so extending through the slots, those portions of the ladder-like grating are allowed to come back into contact with the exterior of the cylindrical tubular portion of the undermold coupling. Such an assembled combination of a hose fitting and a corresponding undermold coupling may then be heated to cause bonding of the flexible plastics material of the undermold coupling to the rigid plastics material of the hose fitting to form a gas-tight seal therebetween, and to cause bonding between the portions of the ladder-like grating that extend through the slots and the exterior surface of the cylindrical tubular portion of the undermold to aid in permanently mechanically interlocking the hose fitting to the undermold.

At one end of each hose, the support helix may be partially unwound, and the unwound end of the support helix may be extended at least partially within the corresponding hose fitting to an electrical connector through which the heating and/or other electrical wires within the support helix may be provided with electrical power and/or may exchange various electrical signals. At the electrical connector, the ends of the heating and/or other electrical wires at the unwound end of the support helix may each be directly soldered to, or otherwise directly electrically connected to, an electrical contact of the electrical connector to. In embodiments in which the hose fitting is a Y-fitting, a T-fitting, or some other form of three-way fitting, such an electrical connector may be carried within a plug that may be carried within, and may entirely close, one of the three cylindrical connections of the hose fitting. In this way, one of the three cylindrical connections of the hose fitting through which gases may have otherwise been caused to flow may be repurposed to serve as an electrical connection point.

In other embodiments, the electrical connector may be located entirely outside of the hose fitting. In such embodiments, the unwound end of the support helix may be caused to further extend out of the hose fitting and to the location of the electrical connector in the environment external to the hose fitting and external to the corresponding hose. The portion of the unwound end of the support helix that extends out of the hose fitting may be sheathed in heat-shrink tubing or other material to provide a degree of physical protection to that portion of the unwound end of the support helix. Such heat-shrink tubing or other material providing such a sheath may also provide thermal insulation to prevent a patient or other person who comes into contact with that portion of the unwound end of the support helix being burned by the heat emitted by heating wires that may extend therethrough. In this way, the portion of the unwound end of the support helix that extends outside of the hose fitting is repurposed to serve as a "pigtail" to enable an electrical connection to a medical device to provide electric power to the heating wires and/or to enable an exchange of electrical signals with other electrical wires within the support helix.

BRIEF DESCRIPTION OF THE DRAWINGS

A fuller understanding of what is disclosed in the present application may be had by referring to the description and claims that follow, taken in conjunction with the accompanying drawings, wherein:

FIGS. 60, 6P, 6Q, 6R and 6S, together, provide cross-sectional views of a variety of embodiments of support helix having a generally rectangular cross-section.

DETAILED DESCRIPTION

Figure 1A:
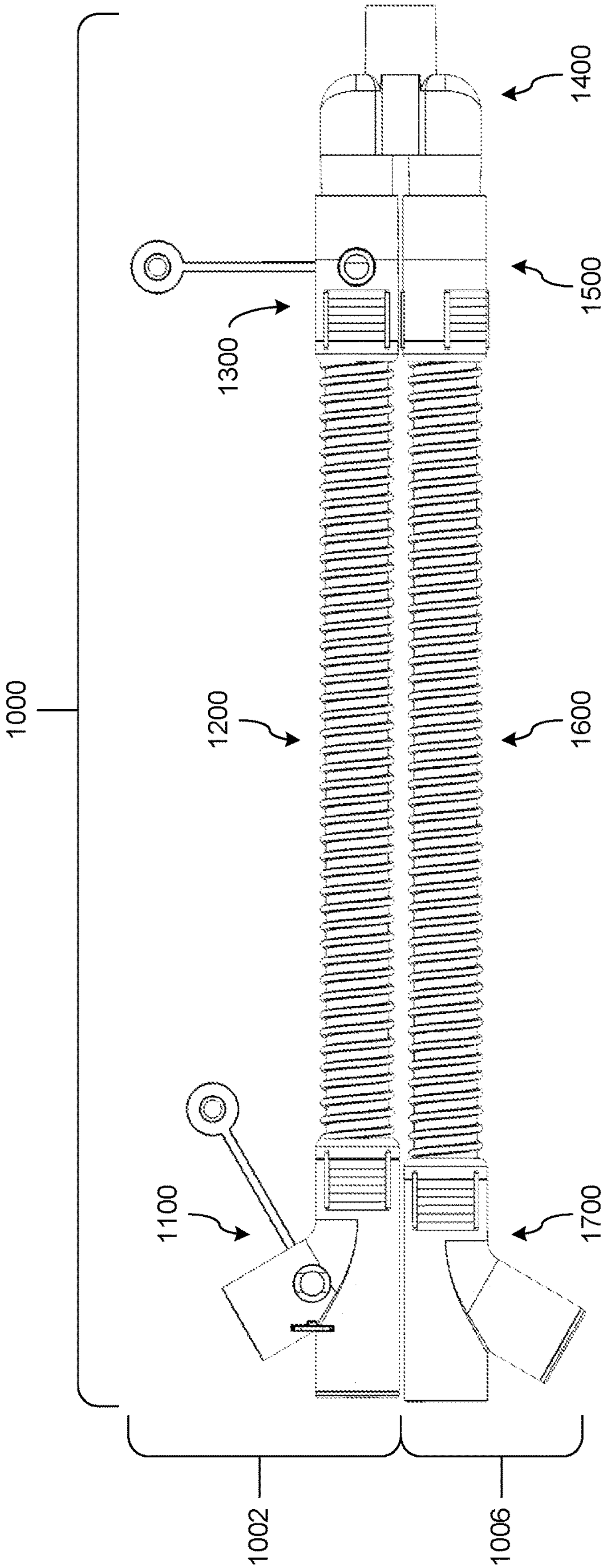
FIG. 1A is an elevational view of an example embodiment of a heated respiratory hose assembly.

FIGS. 1A through 1E, taken together, depict aspects of a novel heated respiratory hose assembly 1000 that addresses many of the shortcomings of prior art assemblies, including those discussed above. As depicted in FIG. 1A, the heated respiratory hose assembly 1000 may include two sub-assemblies, specifically an inspiratory hose assembly 1002 by which respiratory gases may be conveyed from a medical device to a patient to breathe in, and an expiratory hose assembly 1006 by which respiratory gases breathed out by the patient may be conveyed back to the medical device. This circular flow is also conceptually depicted in FIG. 2A.

The inspiratory hose assembly 1002 includes an inspiratory inlet fitting 1100 for connection to a medical device 990 (e.g., a ventilator or CPAP device), an inspiratory outlet fitting 1300 for connection to a parallel Y-fitting 1400 at the patient end, and an inspiratory hose 1200 to convey respiratory gases received by the inspiratory inlet fitting 1100 from the medical device 990 and to the inspiratory outlet fitting 1300 to be conveyed onward to the patient through the parallel Y-fitting 1400. Correspondingly, the expiratory hose assembly 1006 includes an expiratory inlet fitting 1500 for connection to the parallel Y-fitting 1400 at the patient end, an expiratory outlet fitting 1700 for connection to the medical device 990, and an expiratory hose 1600 to convey respiratory gases received by the expiratory inlet fitting 1500 from the patient through parallel Y-fitting 1400 and to the expiratory outlet fitting 1700 to be conveyed onward to the medical device 990. At the patient end, the parallel Y-fitting 1400 may connect the heated respiratory hose assembly 1000 to a face mask 940, an endotracheal tube 940, a tracheostomy stoma 940 (see FIG. 2A) or other component.

Figure 1B:
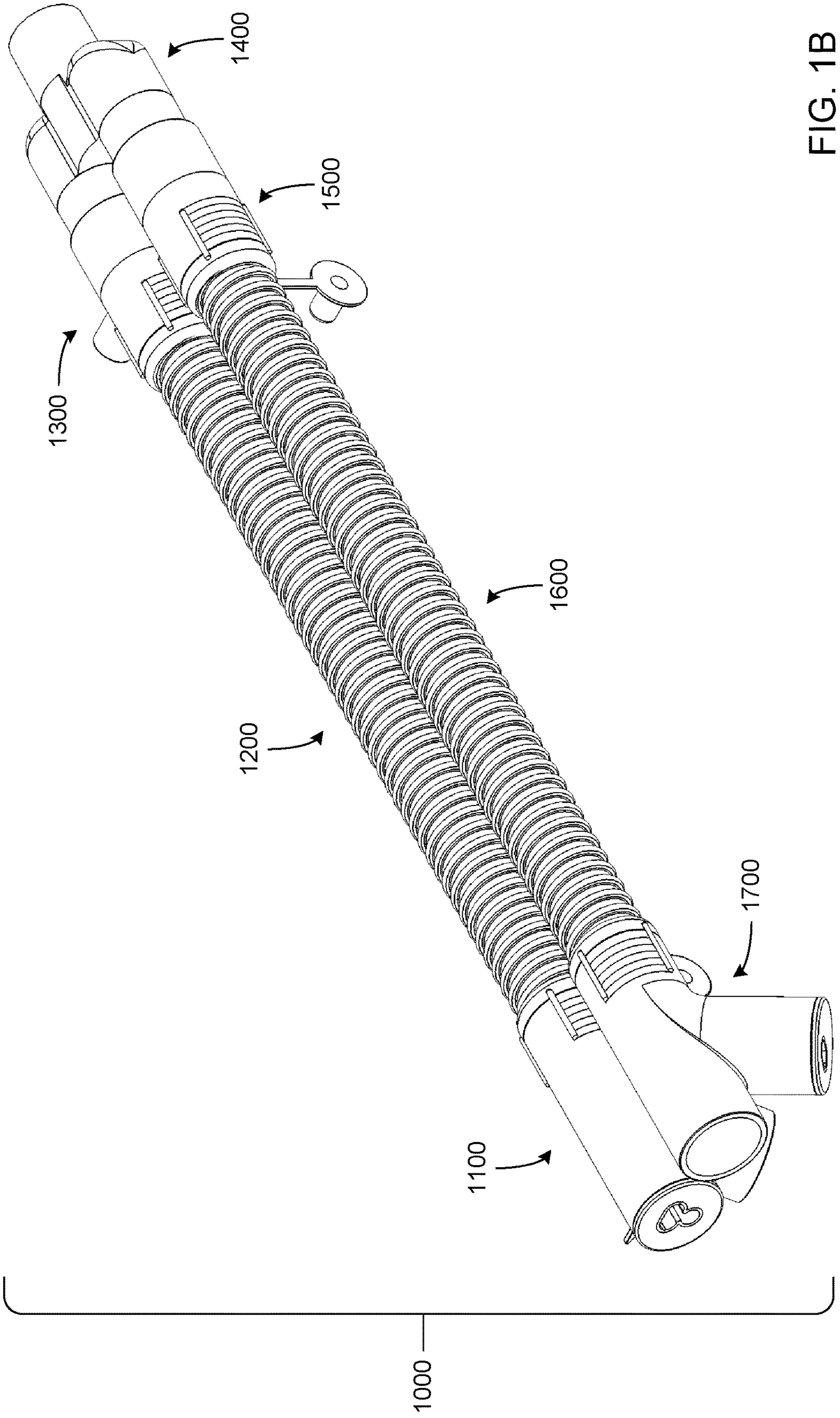
FIG. 1B is a perspective view of the heated respiratory hose assembly of FIG. 1A showing details of electrical connectors thereof.
Figure 1C:
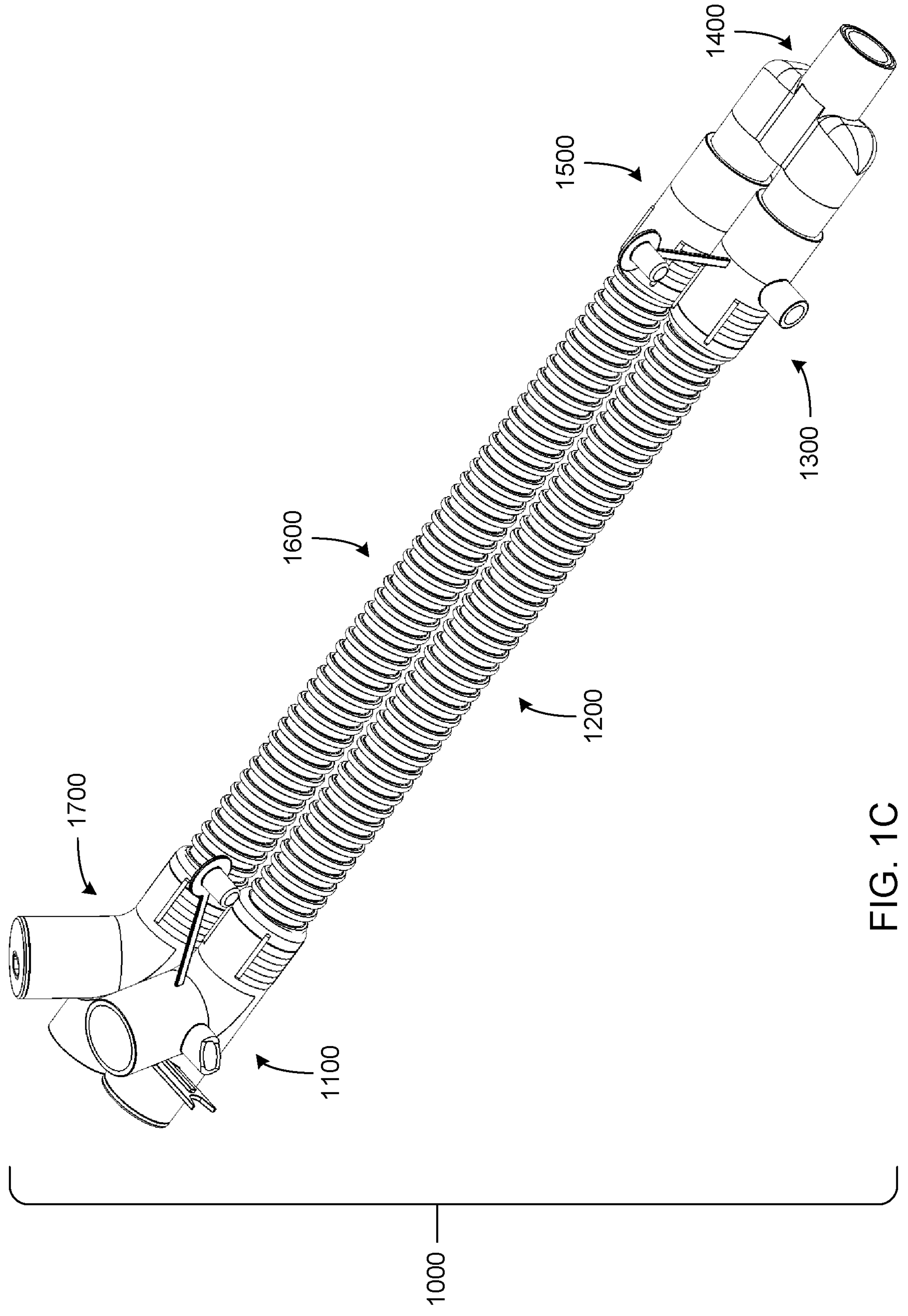
FIG. 1C is another perspective view of the heated respiratory hose assembly of FIG. 1A.
Figure 1D:
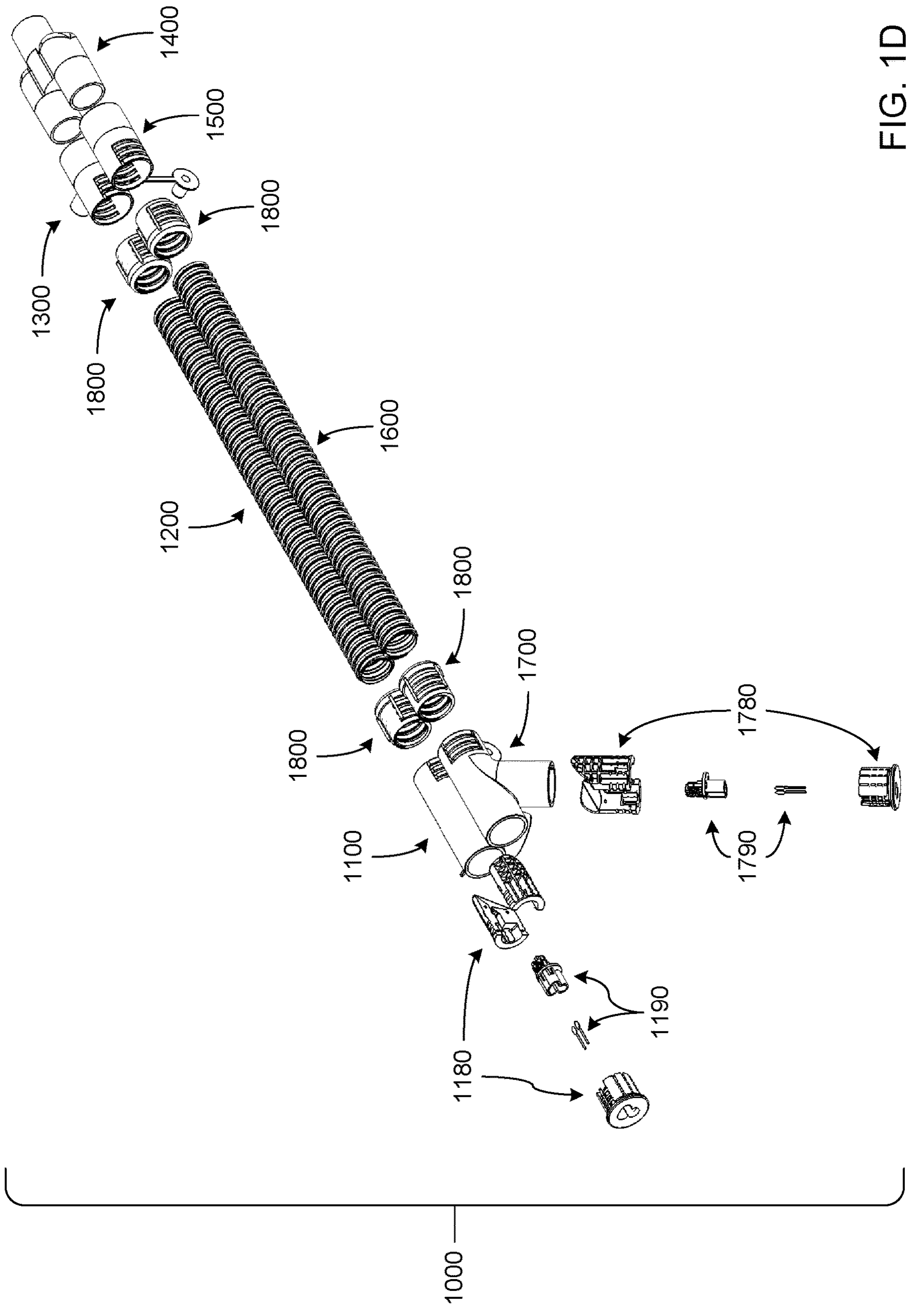
FIG. 1D is an exploded perspective view of the heated respiratory hose assembly of FIG. 1A showing details of the electrical connectors thereof and details of the coupling of hoses to hose fittings thereof.
Figure 1E:
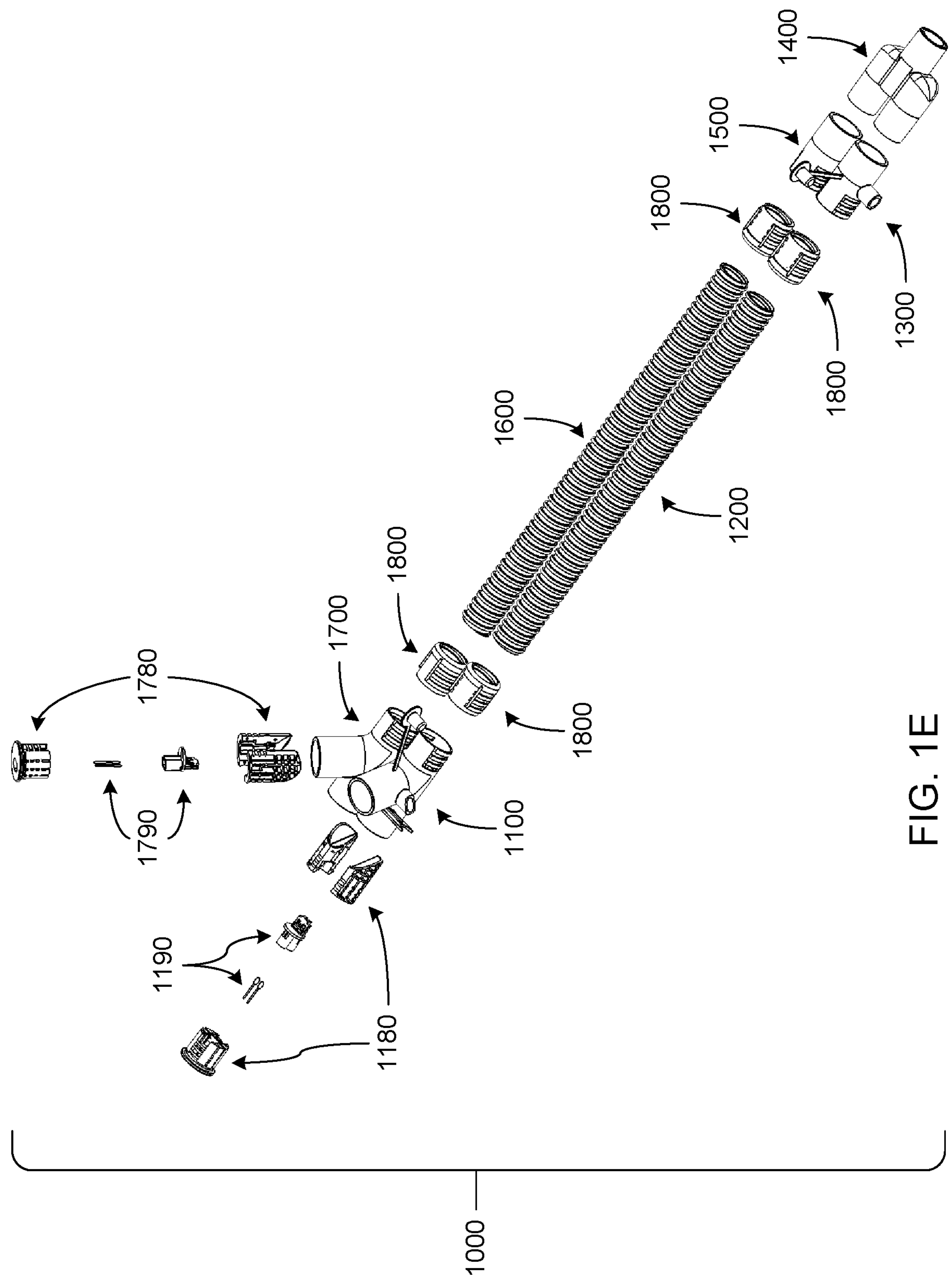
FIG. 1E is another exploded perspective view of the heated hose assembly of FIG. 1A.

Each of FIGS. 1B and 1C provide a perspective view of one embodiment of the heated respiratory hose assembly 1000 in which the inspiratory inlet fitting 1100 and the expiratory outlet fitting 1700 are both implemented with 120-degree Y-fittings in which there is both a straight-through path for either gases or wiring to pass from the hoses 1200 and 1600, respectively, and an angled path that branches off from the straight-through path at a 120-degree angle relative to the connections to the hoses 1200 and 1600, respectively. Each of FIGS. 1D and 1E provide an exploded perspective view of this embodiment. In this embodiment, one of the connections of each of the Y-fittings 1100 and 1700 is occupied by a plug 1180 and 1780 that carries an electrical connector 1190 and 1790, respectively. In the depicted variant of this embodiment, at the inspiratory inlet fitting 1100, the straight-through connection (relative to the connection to the inspiratory hose 1200) is occupied by the plug 1180 that carries the electrical connector 1190 by which electric power is able to be provided to a pair of heating wires incorporated into the support helix of the inspiratory hose 1200, as will be explained in greater detail. Correspondingly, in this depicted variant of this embodiment, at the expiratory outlet fitting 1700, the 120-degree connection (relative to the connection to the expiratory hose 1600) is occupied by the plug 1780 that carries the electrical connector 1790 by which electric power is able to be provided to a pair of heating wires incorporated into the helix of the expiratory hose 1600, as will also be explained in greater detail.

It should be noted that, despite such a depiction of the use of particular ones of the three connections of each of the Y-fittings 1100 and 1700 in FIGS. 1A-E as being occupied by plugs carrying electrical connectors, different connections of the Y-fittings 1100 and 1700 may be so occupied in other variants of the embodiment of the heated respiratory hose assembly 1000 of FIGS. 1A-E. Also, and as will be depicted in subsequent figures, it should be noted that other embodiments of the heated respiratory hose assembly 1000 may employ hose fitting(s) 1100 and/or 1700 of an entirely different type that may each provide a different selection of connections from which one may be chosen to be occupied by a plug carrying an electrical connector.

Figure 2A:
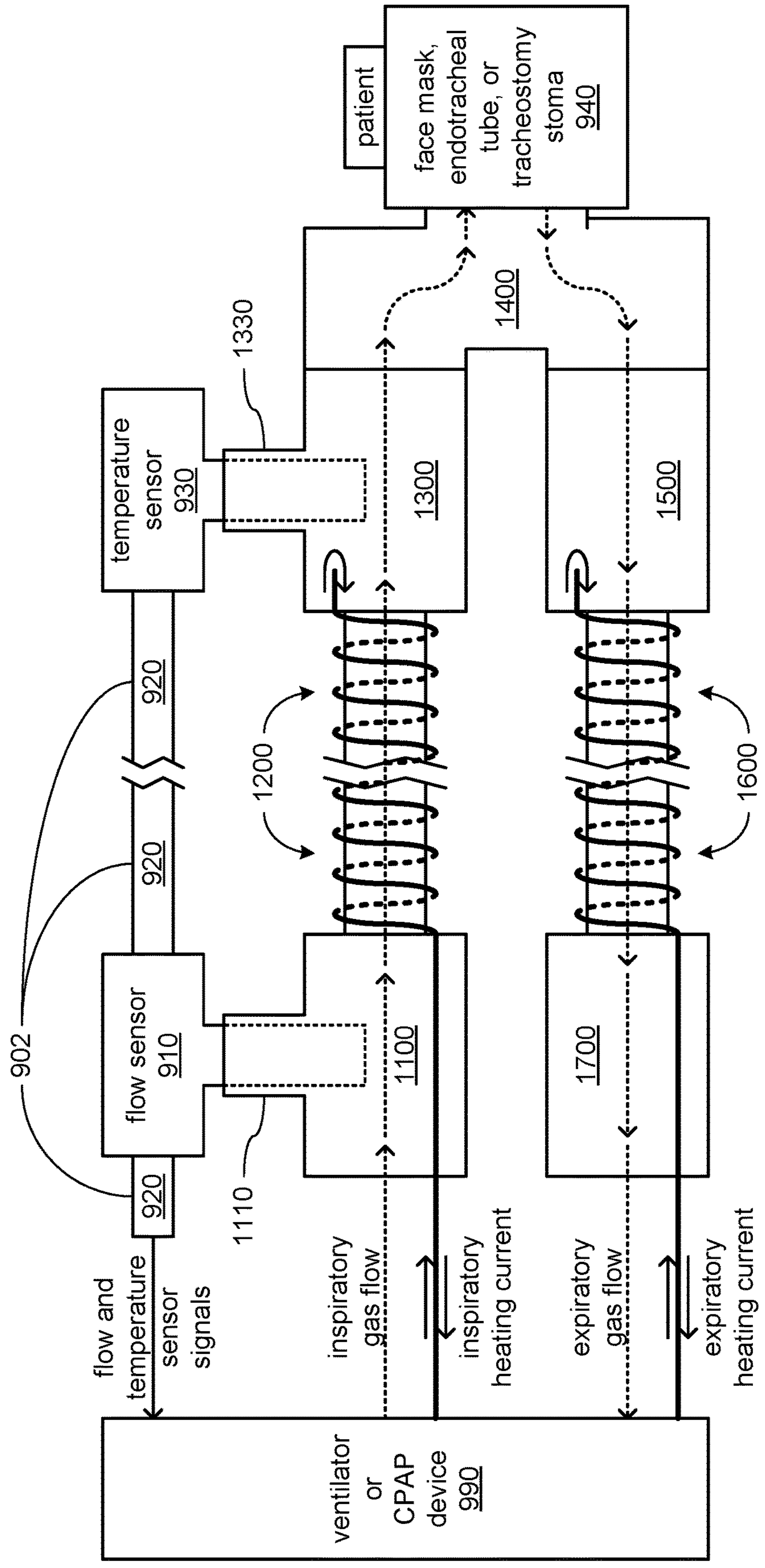
FIG. 2A is a block diagram of heated respiratory hose assembly of FIG. 1A showing details of the flow of respiratory gases therethrough and the monitoring of flow and temperature thereof.
Figure 2B:
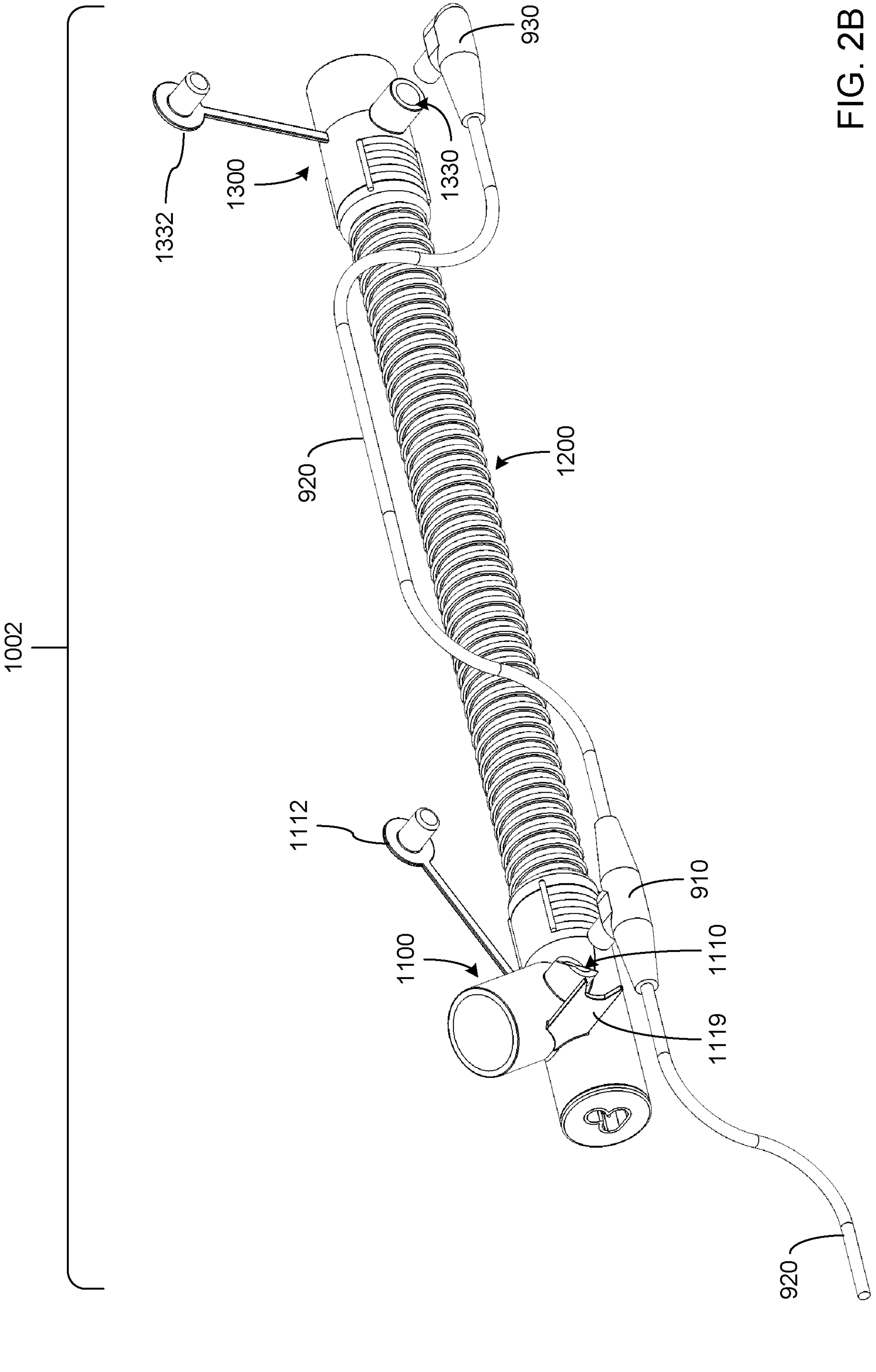
FIG. 2B is a perspective view of the inspiratory hose assembly of the heated respiratory hose assembly of FIG. 1A showing details of a sensor harness that is to be connected thereto.
Figure 2C:
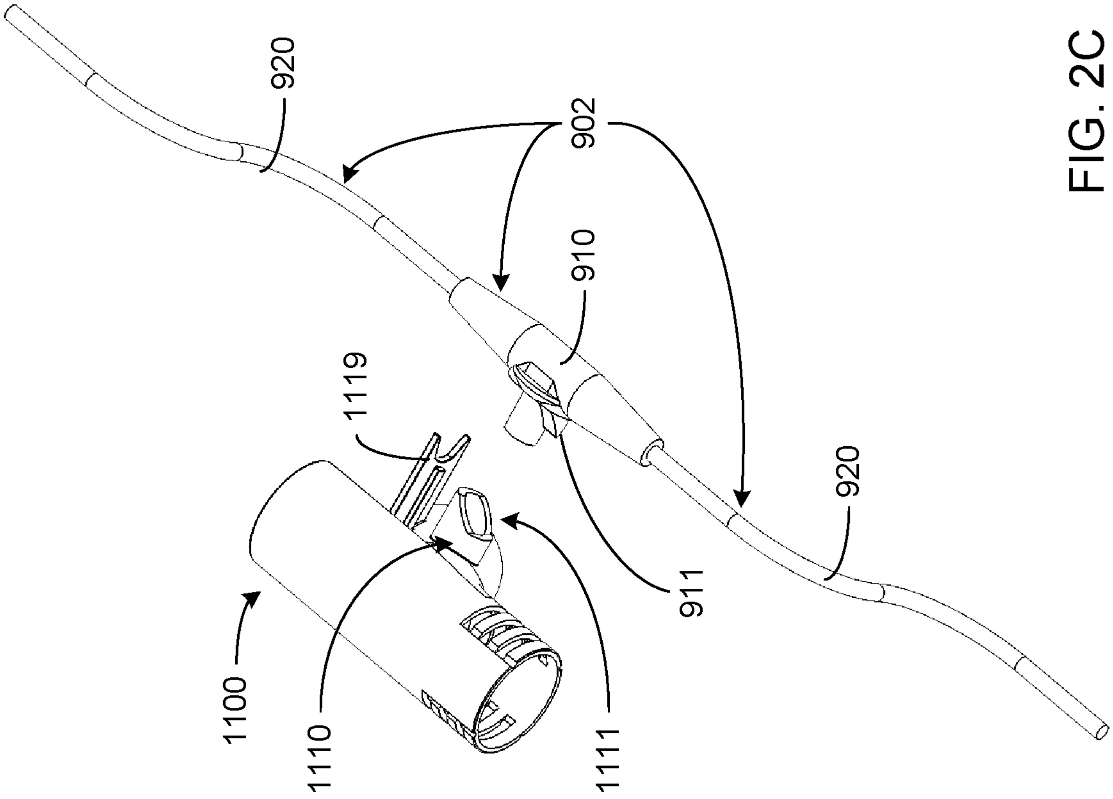
FIG. 2C is a perspective view of the inspiratory inlet fitting of the inspiratory hose assembly of FIG. 2B showing features of the inspiratory inlet fitting to aid in correctly connecting a flow sensor of the sensor harness to enable correct operation thereof.

FIGS. 2A through 2C, taken together, depict aspects of the use of sensors with at least the inspiratory hose assembly 1002 of the heated respiratory hose assembly 1000 to monitor the flow and/or temperature of at least respiratory gases from the medical device 990 to the patient. As depicted, the inspiratory inlet fitting 1100 may additionally include a flow sensor port 1110 formed through a portion of the wall of the inspiratory inlet fitting 1100. The flow sensor port 1110 provides an opening into the inspiratory interior of the inlet fitting 1100 through which a flow sensor 910 of a sensor harness 902 is able to be inserted to continually confirm the flow of respiratory gases from the medical device 990 and toward the patient at the patient end. As will be explained in greater detail, the flow sensor 910 is directional in nature such that it must be installed within the flow sensor port 1110 in a correct orientation to function properly.

As depicted, the inspiratory outlet fitting 1300 may additionally include a temperature sensor port 1330 formed through the wall of the inspiratory outlet fitting 1300. The temperature sensor port 1330 provides an opening into the interior of the inspiratory outlet fitting 1300 by which a temperature sensor 930 of the sensor harness 902 is able to be inserted to continually monitor the temperature of the respiratory gases output by the medical device 990 at a location towards the patient end (i.e., just before those respiratory gases are conveyed through the inspiratory outlet fitting 1300 and into the parallel Y-fitting 1400 to be conveyed onward to the patient).

In some embodiments, and as can best be seen in FIG. 2B, the inspiratory inlet fitting 1100 may carry a port plug 1112 that may be used to close and seal the flow sensor port 1110 in situations where at least the inspiratory hose assembly 1002 is used without the flow sensor 910 installed within the flow sensor port 1110. Alternatively or additionally, the inspiratory outlet fitting 1300 may carry a port plug 1332 that may similarly be used to close and seal the temperature sensor port 1330 in situations where at least the inspiratory hose assembly 1002 is used without the temperature sensor 930 installed within the temperature sensor port 1330. As depicted, the port plugs 1112 and 1332 may be carried by the hose fittings 1100 and 1300, respectively, by being attached thereto with elongate stretches of the rigid plastics material of the hose fittings 1100 and 1300 that are long and thin enough as to be sufficiently flexible that the port plugs 1112 and 1332 are able to be maneuvered to and from the ports 1110 and 1330, respectively, for a relatively limited number of times without the elongate stretches breaking.

As also depicted, the flow sensor 910 and the temperature sensor 930 may be physically connected by a length of cabling 920 of the sensor harness 902 that is meant to follow the length of the inspiratory hose 1200, and by which signals of the temperature sensor 930 are conveyed toward the location of the flow sensor 910. As can also be seen, there may also be another length of cabling 920 of the sensor harness 902 that extends from the flow sensor 910 and towards the medical device 990 to convey the signals of both sensors 910 and 930 to the medical device 990.

Referring more specifically to FIG. 2A, during operation of the medical device 990, respiratory gases to be breathed in by a patient are conveyed from the medical device 990, through the inspiratory inlet fitting 1100, then the inspiratory hose 1200, then the inspiratory outlet fitting 1300, then the parallel Y-fitting 1400, and then to the patient via still another component, such as a face mask 940, an endotracheal tube 940, a tracheostomy stoma 940 or other component. Also during operation of the medical device 990, respiratory gases breathed out by the patient are conveyed from the patient through such a component (e.g., the face mask 940, the tracheal tube 940, the tracheostomy stoma 940 or other component), then the parallel Y-fitting 1400, then the expiratory inlet fitting 1500, then the expiratory hose 1600, then the expiratory outlet fitting 1700, and onward to the medical device 990.

While this circular flow of respiratory gases goes on between the medical device 990 and the patient, the medical device 990 monitors the flow sensor 910 to ensure that respiratory gases to be breathed in by the patient are, in fact, output by the medical device 990 and into the inspiratory hose assembly 1002 of the heated respiratory hose assembly 1000 towards the patient. If a lack of flow and/or flow in a wrong direction is detected by the sensor 910, then the medical device 990 may sound an alarm and/or provide some other audio and/or visual indication of the lack of flow and/or the incorrect direction of flow. Also while this circular flow of respiratory gases goes on between the medical device 990 and the patient, the medical device monitors the temperature sensor 930 to ensure that the respiratory gases that reach the patient end of the inspiratory hose 1200 are of a correct temperature, both to prevent condensation within the inspiratory hose 1200, and for the health of the patient.

Referring more specifically to FIG. 2C, as just discussed, the directional nature of the flow sensor 910 requires correct installation of the flow sensor 910 within the interior of the inspiratory inlet fitting 1100 to ensure that it is caused to sense the flow of respiratory gases towards the patient with a correct orientation. Otherwise, it may be that the flow sensor 910 is caused to at least attempt to detect a flow of respiratory gases in a direction opposite of the correct direction towards the patient. The inspiratory inlet fitting 1100 may carry a flow sensor guide 1119 adjacent to the flow sensor port 1110 to cooperate with the shape of a portion of the exterior of the flow sensor 910 to aid in correctly positioning the flow sensor 910 relative to the flow sensor port 1110 and the interior of the inspiratory inlet fitting 1100. Alternatively or additionally, the flow sensor port 1110 may be formed to include a short tube-like portion with a bevel cut 1111 to interact with an orientation key 911 carried on a portion of the exterior of the flow sensor 910 to aid in correctly positioning the flow sensor 910 relative to the flow sensor port 1110 and the interior of the inspiratory inlet fitting 1100.

The medical device 990 may selectively turn on and off the provision of electric power to heating wires within the inspiratory hose 1200 and the expiratory hose 1600 to selectively apply heat thereto based on the temperature sensed by the temperature sensor 930. More specifically, and as will be explained in greater detail, each of the hoses 1200 and 1600 may incorporate at least a pair of heating wires that may be connected to the medical device 990 at one end of each of the hoses 1200 and 1600, and that may be soldered, crimped or otherwise electrically connected at the other end of each of the hoses 1200 and 1600 to form a separate closed loop of electric current through each of the hoses 1200 and 1600.

Some medical devices 990 may turn on and off the provision of electric power to the heating wires of both hoses together. Indeed, some medical devices 990 may selectively provide the very same voltage from the very same power source to the heating wires of both hoses. However, it may be the case that each of the two hoses 1200 and 1600 are to be heated to different temperatures. Thus, the heating wires employed in the two hoses 1200 and 1600 may be of different resistances and/or have other differing characteristics to bring about such a difference in temperature. More specifically, it may be deemed desirable to heat the respiratory gases being conveyed to the patient through the inspiratory hose 1200 to a higher temperature than the respiratory gases being conveyed from the patient through the expiratory hose 1600. The heating of gases conveyed to the patient may be deemed of greater importance for such purposes as achieving a particular higher temperature to help the patient maintain a particular body temperature, aid in treating the patient for a particular respiratory illness, etc. Such heating of the gases conveyed to the patient would also be intended to prevent condensation from occurring within the inspiratory hose 1200. In contrast, the heating of gases conveyed from the patient may be solely for the purpose of preventing condensation from occurring within the expiratory hose 1600.

Figure 3A:
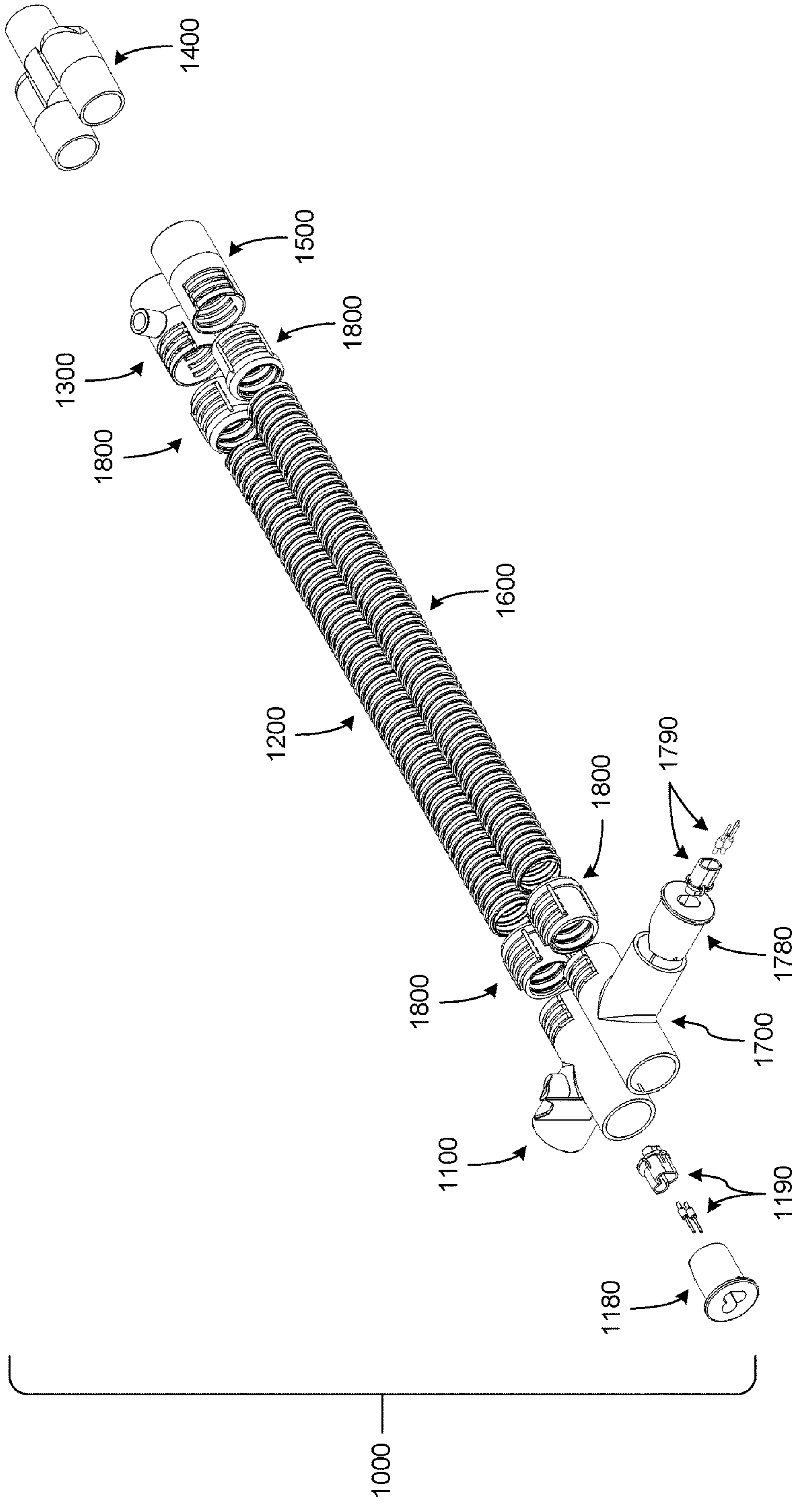
FIG. 3A is an exploded perspective view of an alternate embodiment of a heated respiratory hose assembly.
Figure 3B:
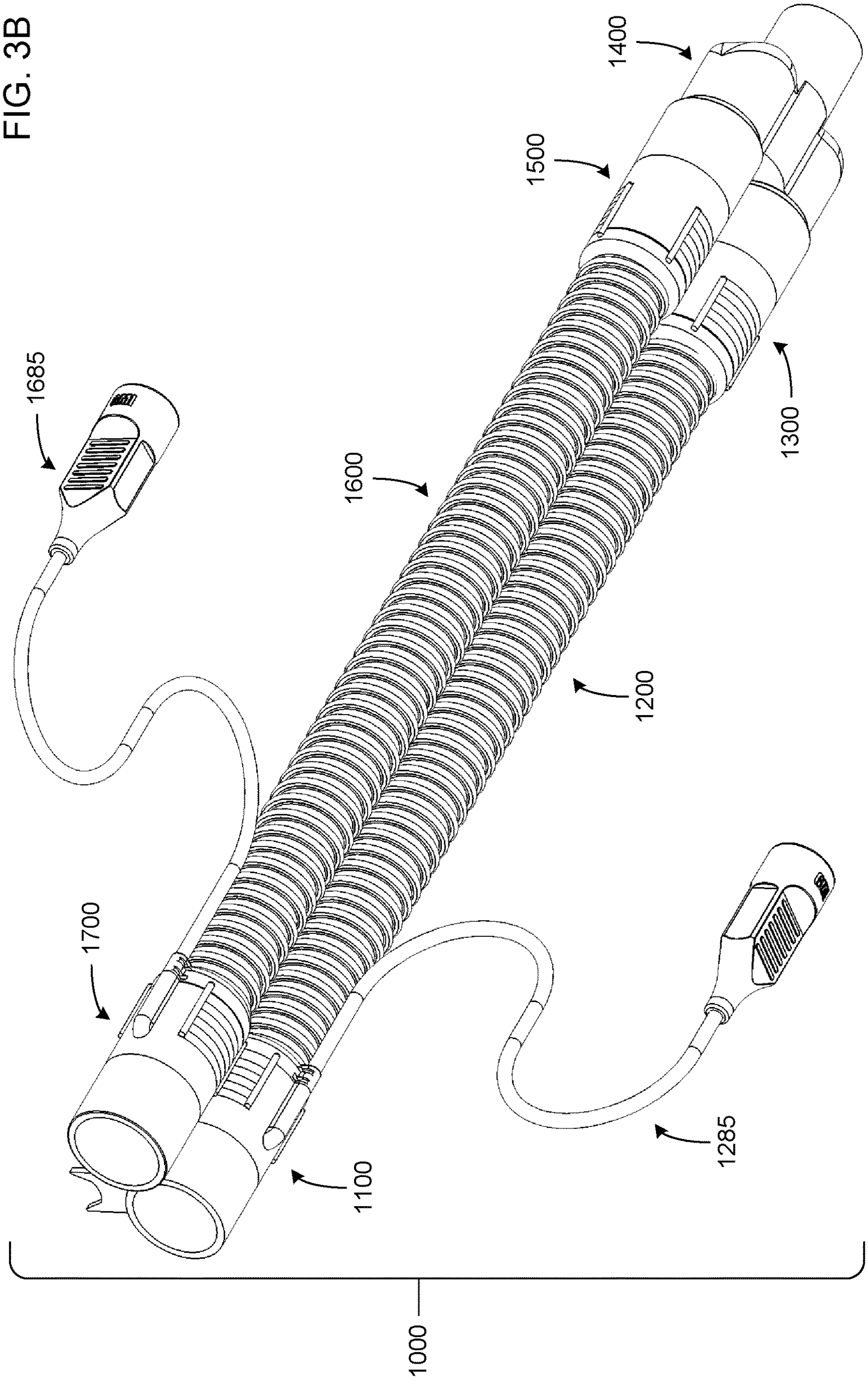
FIG. 3B is a perspective view of another alternate embodiment of a heated respiratory hose assembly.
Figure 3C:
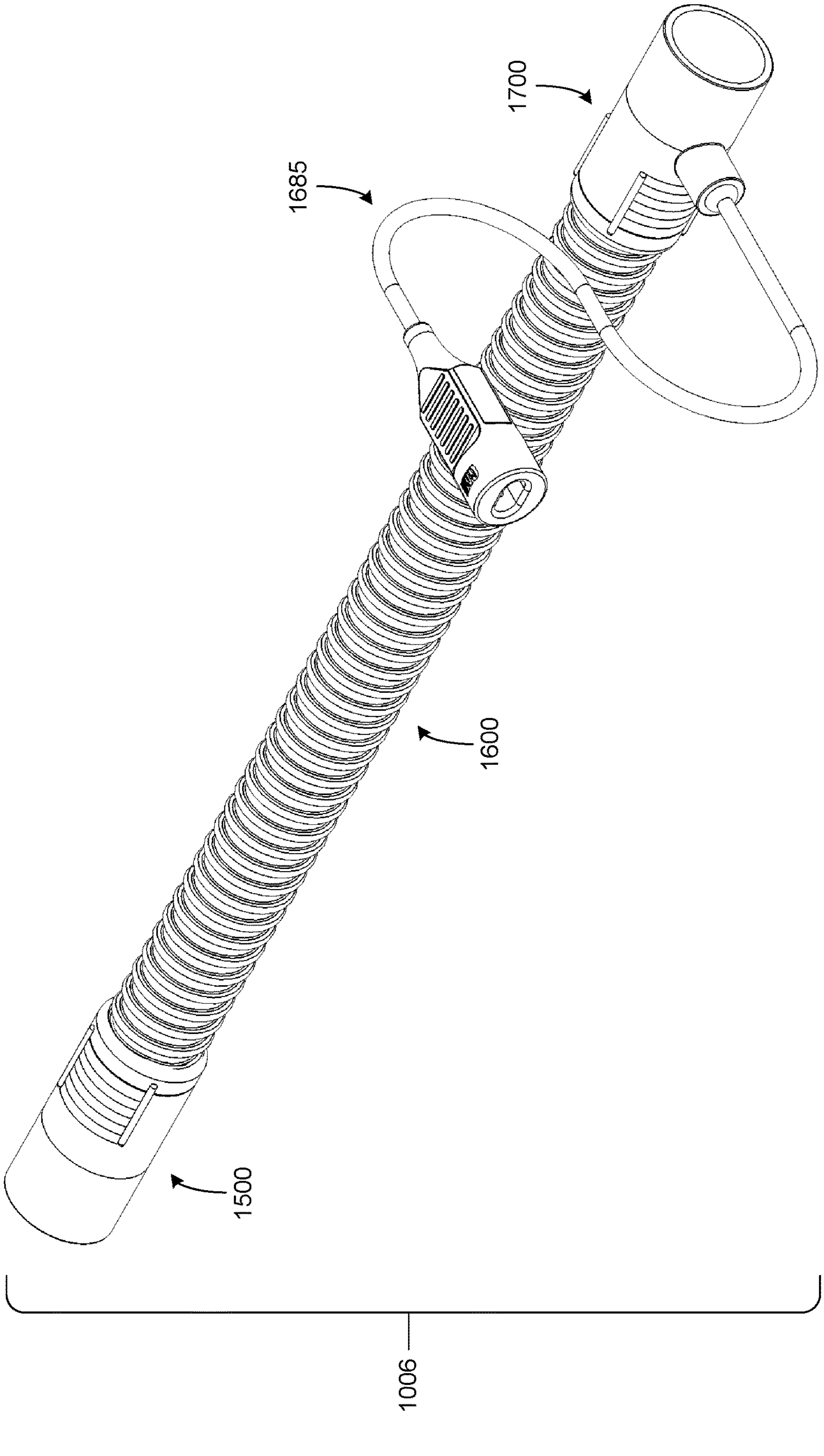
FIG. 3C is a perspective view of the inspiratory hose assembly of still another embodiment of a heated respiratory hose assembly.

Each of FIGS. 3A through 3C depict another possible embodiment of the heated respiratory hose assembly 1000 in which other possible different versions (or combinations of versions) of the inspiratory inlet fitting 1100 and the expiratory outlet fitting 1700 may be used. FIG. 3A provides an exploded perspective view of an alternate embodiment of the heated respiratory hose assembly 1000 in which the inspiratory inlet fitting 1100 and the expiratory outlet fitting 1700 are both T-fittings, instead of the 120-degree Y-fittings depicted in FIGS. 1A through 1E. FIG. 3B provides a perspective view of another alternate embodiment of the heated respiratory hose assembly 1000 in which the inspiratory inlet fitting 1100 and the expiratory outlet fitting 1700 are both through-fittings, and from each of which a pigtail 1285 and 1685 emerges by which the electrical connection to the heating wires of the hoses 1200 and 1600, respectively, are separately made. FIG. 3C provides a perspective view of the expiratory hose assembly 1006 of still another embodiment of the heated respiratory hose assembly 1000 in which at least the expiratory outlet fitting 1700 is a through-fitting from which the pigtail 1685 by which electrical connection is made to the heating wires of the expiratory hose 1600 emerges in a direction perpendicular to the direction from which the expiratory hose 1600 emerges. In contrast, the pigtails 1285 and/or 1685 depicted in the embodiment of FIG. 3B emerge from the hose respective fittings 1100 and/or 1700 in a direction that is parallel to (and alongside) the hoses 1200 and/or 1600, respectively.

It should be noted that, despite such depictions of particular alternate embodiments, still other alternate embodiments of the heated respiratory hose assembly 1000 are possible in which still other types of fittings are employed as one or both of the inspiratory inlet fitting 1100 and the expiratory outlet fitting 1700. Further, it should be noted that, despite the depictions of the inspiratory outlet fitting 1300 and of the expiratory inlet fitting 1500 being unchanged throughout these multiple depicts of differing embodiments of the heated respiratory hose assembly 1000, other embodiments are possible in which other types of fittings may be employed as one or both of the inspiratory outlet fitting 1300 and the expiratory inlet fitting 1500. Further, it should be noted that, despite the depictions of the inspiratory inlet fitting 1100 and the expiratory outlet fitting 1700 being of the same type, still other embodiments of the heated respiratory hose assembly 1000 are possible in which the inspiratory inlet fitting 1100 and the expiratory outlet fitting 1700 are of different types (e.g., one may be a Y-fitting and the other may be a T-fitting, or one may be a Y-fitting or T-fitting that carries a plug with an electrical connector and the other may be a through-fitting with a pigtail that carries another plug).

FIGS. 4A through 4G, taken together, depict various aspects of one embodiment of a process for making the inspiratory hose 1200 and/or the expiratory hose 1600, including aspects of forming the support helixes 1280 and/or 1680 thereof to include one or more electrical wires 1290 and/or 1690, respectively. It should be noted that, although, so far, the helixes 1280 and 1680 are depicted as each incorporating a pair of heating wires 1290 and 1690, respectively, other embodiments of the hoses 1200 and/or 1600 are possible in which different quantities of the electrical wires 1290 and/or 1690 (whether heating wires, other types of electrical wires, and/or wires used for other purposes) may be incorporated into the helixes 1280 and/or 1680, respectively, as well as other embodiments in which there may be multiple helixes that each carry one or more different sizes and/or types of electrical wires (again, whether heating wires, or not). It should also be noted that still other embodiments of the hoses 1200 and/or 1600 are possible in which different quantities of lumens 1289 and/or 1689 may be incorporated into the helixes 1280 and/or 1680, respectively, as well as other embodiments in which there may be multiple helixes that each carry one or more different sizes of lumens. It should further be noted that yet other embodiments of the hoses 1200 and/or 1600 are possible in which there may be any of a variety of combinations of lumens 1289 and/or 1689, and of wires 1290 and/or 1690.

Figure 4A:
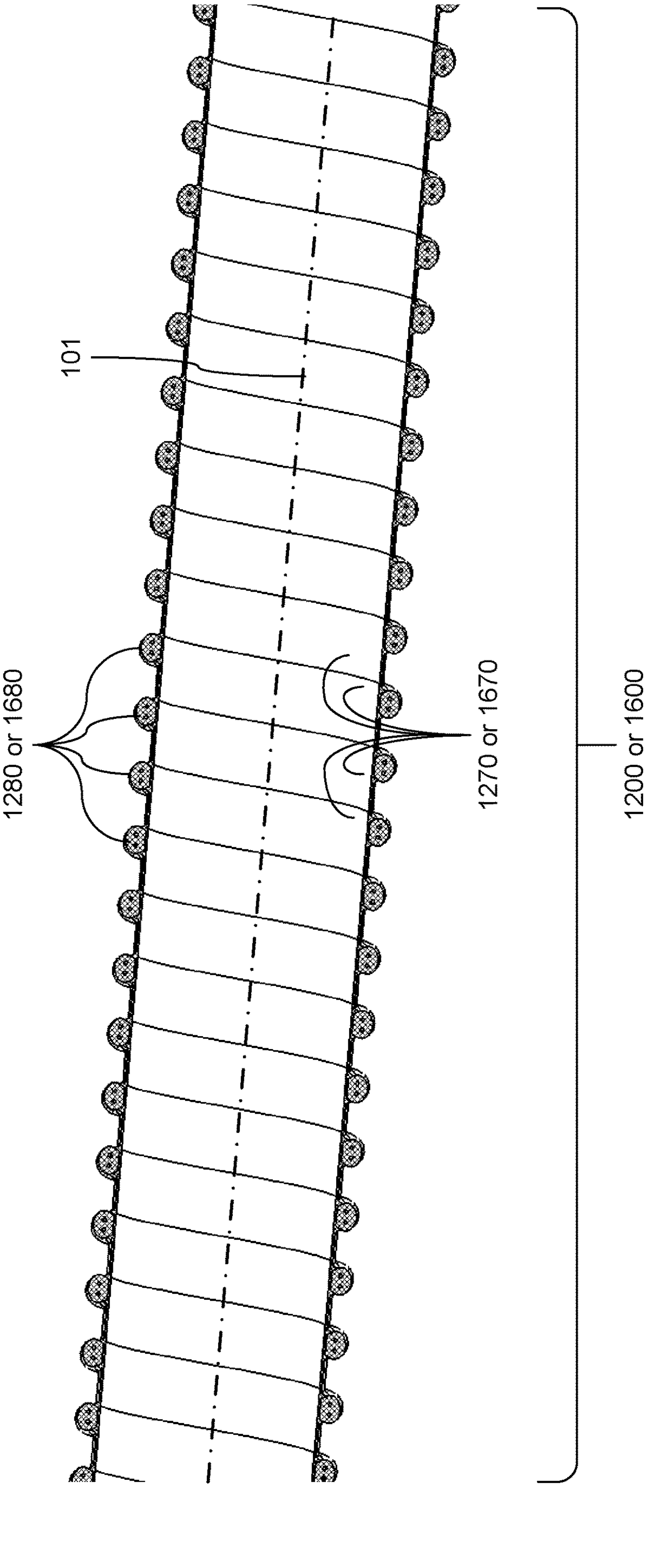
FIG. 4A is a cross-sectional view of a portion of one of the hoses of any of the embodiments of heated respiratory hose assembly of any of FIG. 1A, 3A, 3B or 3C showing details of the wall and support helix thereof.

As depicted most clearly in FIG. 4A, each of the hoses 1200 and 1600 may include a wall 1270 and 1670, respectively, that is physically supported by a corresponding one of the support helixes 1280 and 1680. As also depicted, the support helixes 1280 and 1680 may spirally wrap around the exterior of the walls 1270 and 1670, respectively, in a manner that leaves a continuous helical stretch of the walls 1270 and 1670 between adjacent coils of the support helixes 1280 and 1680 that enable the hoses 1200 and 1600, respectively, to be flexible enough to bend. Additionally, such spacing between adjacent coils of the support helixes 1280 and 1680 may be of a distance selected to allow fold(s), curve(s) and/or convolution(s) to be formed in the continuous helical stretch of the walls 1270 and 1670 therebetween to enable the hoses 1200 and 1600, respectively, to be axially stretched and compressed (i.e., lengthened or shortened along the depicted axis 101), as well as to bend.

Figure 4B:
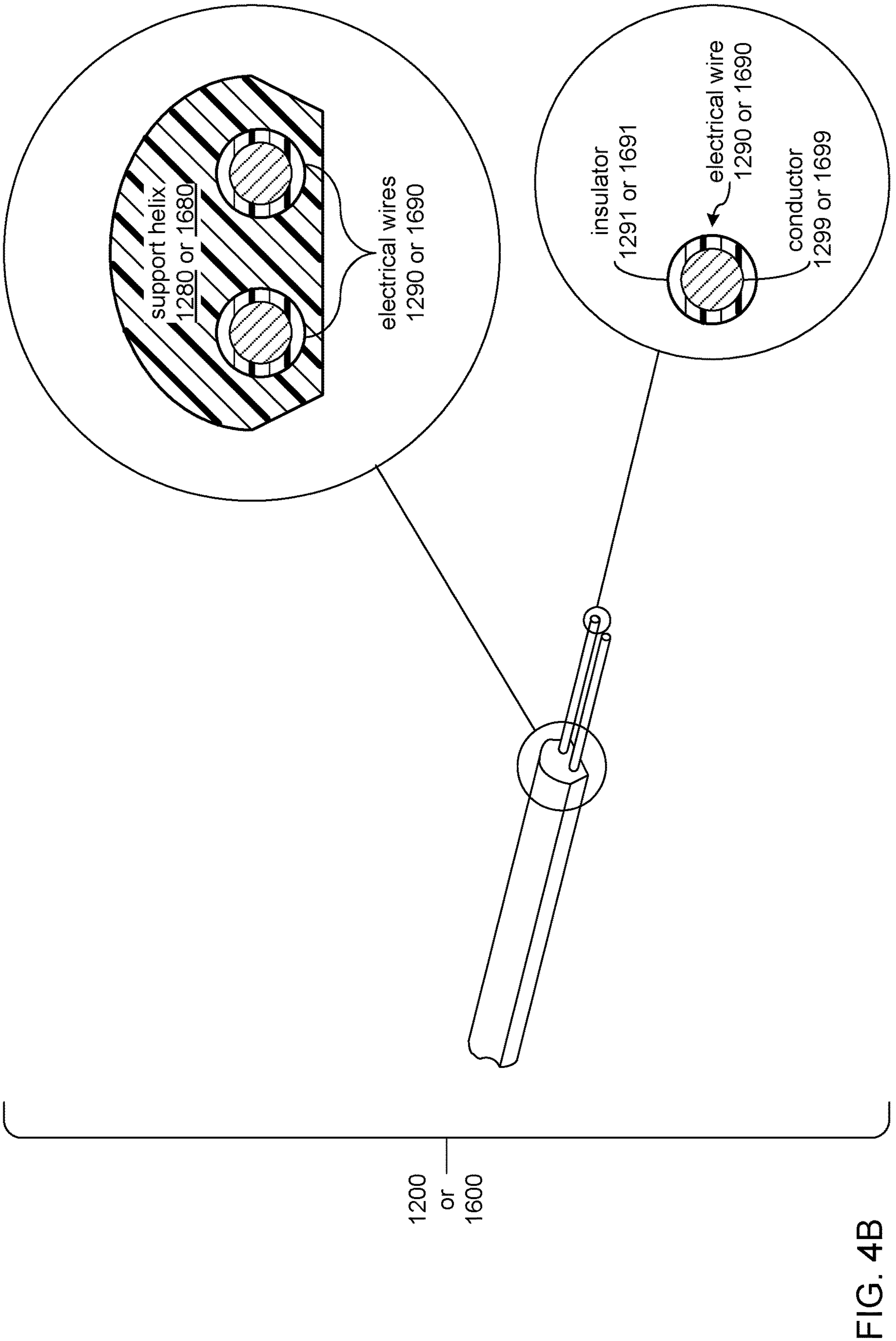
FIG. 4B is a combination of perspective and cross-sectional views of a portion of the support helix of the hose of FIG. 4A showing details of the electrical wires incorporated therein.

As depicted most clearly in FIG. 4B, the support helixes 1280 and/or 1680 may incorporate heating wires 1290 and/or 1690 that may be positioned within the flexible plastics material of the support helixes 1280 and/1680 to bring them closer to the interior of the hoses 1200 and/or 1600, respectively, than to the environment external thereto. In this way, much of the flexible plastics material that makes up the support helixes 1280 and/or 1680 may be used as insulation to tend to cause the heat generated by the heating wires 1290 and/or 1690 to be radiated into the interiors of the hoses 1200 and/or 1600, respectively, instead of being wasted by being radiated into the environment external to the hoses 1200 and/or 1600.

As also depicted most clearly in FIG. 4B, each individual heating wire 1290 or 1690 may incorporate a conductor 1291 or 1691, and an individual insulator 1292 or 1692 in addition to the insulation provided by the flexible plastics material of the support helix 1280 or 1680, respectively. In some embodiments, the heating wire 1290 or 1690 may be a variant of magnet wire or similar wire with a selected resistance where the insulator 1292 or 1692, respectively, may be one or more layers of polymer or other type of film. As will be recognized by those skilled in the art, such insulator(s) 1292 and/or 1692 may be selected to be capable of resisting temperatures expected to be encountered during heating of the hoses 1200 and/or 1600, respectively, but to not be capable resisting temperatures typically encountered during soldering such that electrical connections may be made to such wire(s) 1290 and/or 1690 using any of a variety of soldering techniques without requiring stripping of the insulation 1292 and/or 1692, respectively, in preparation therefor.

Figure 4C:
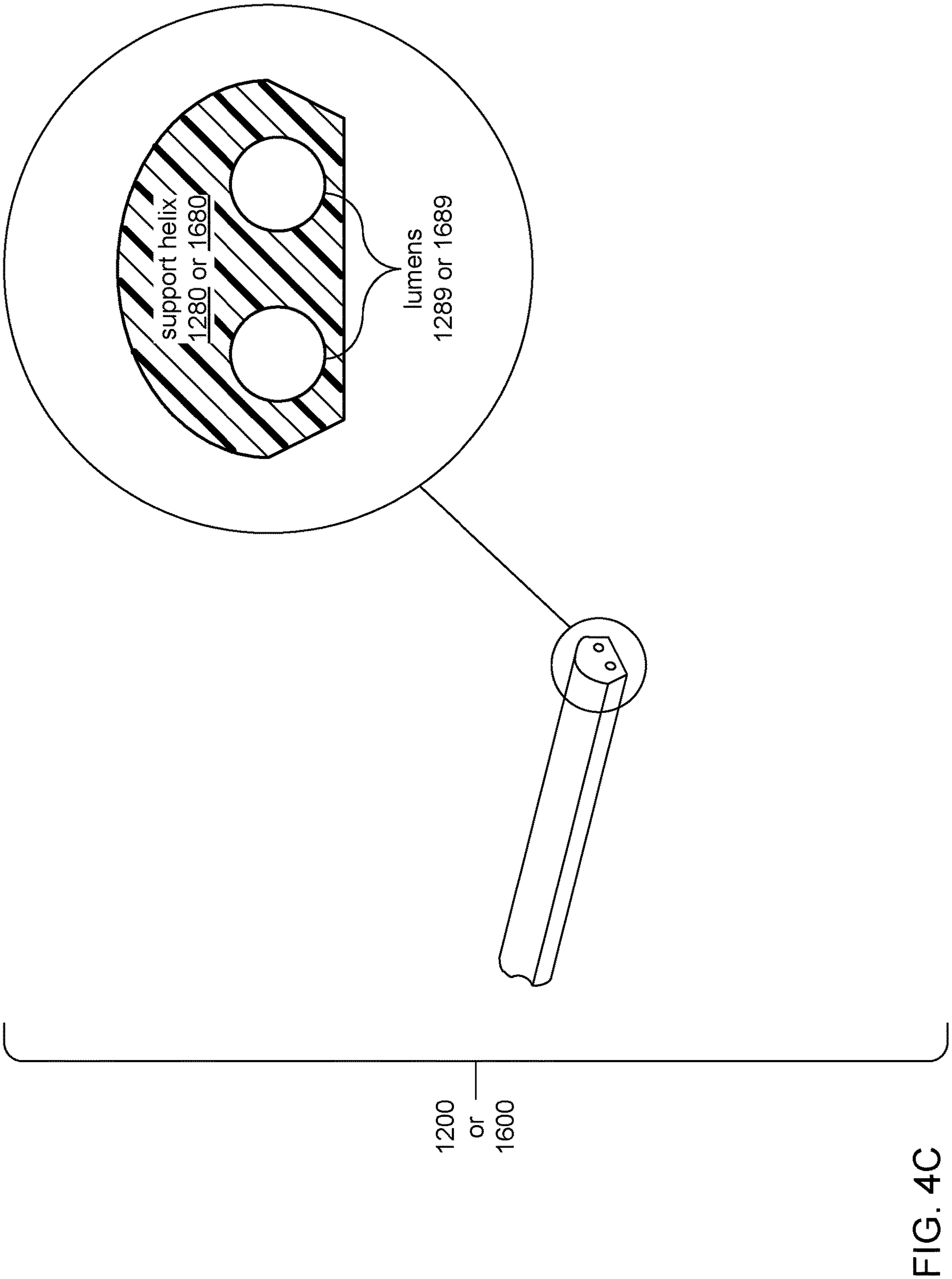
FIG. 4C is a combination of perspective and cross-sectional views of a portion of the support helix of an alternate variant of the hose of FIG. 4A showing details of lumens incorporated therein in lieu of electrical wires.

Alternatively, and as depicted most clearly in FIG. 4C, the support helixes 1280 and/or 1680 may incorporate lumens 1289 and/or 1689 that may be similarly positioned within the flexible plastics material of the support helixes 1280 and/1680 to bring them closer to the interior of the hoses 1200 and/or 1600, respectively, than to the environment external thereto. In this way, where the lumens 1289 and/or 1689 are used for purposes of heating, again, much of the flexible plastics material that makes up the support helixes 1280 and/or 1680 may be used as insulation to tend to cause more heat to be radiated into the interiors of the hoses 1200 and/or 1600 from the lumens 1289 and/or 1689, respectively, instead of being wasted by being radiated into the environment external to the hoses 1200 and/or 1600.

Figure 4D:
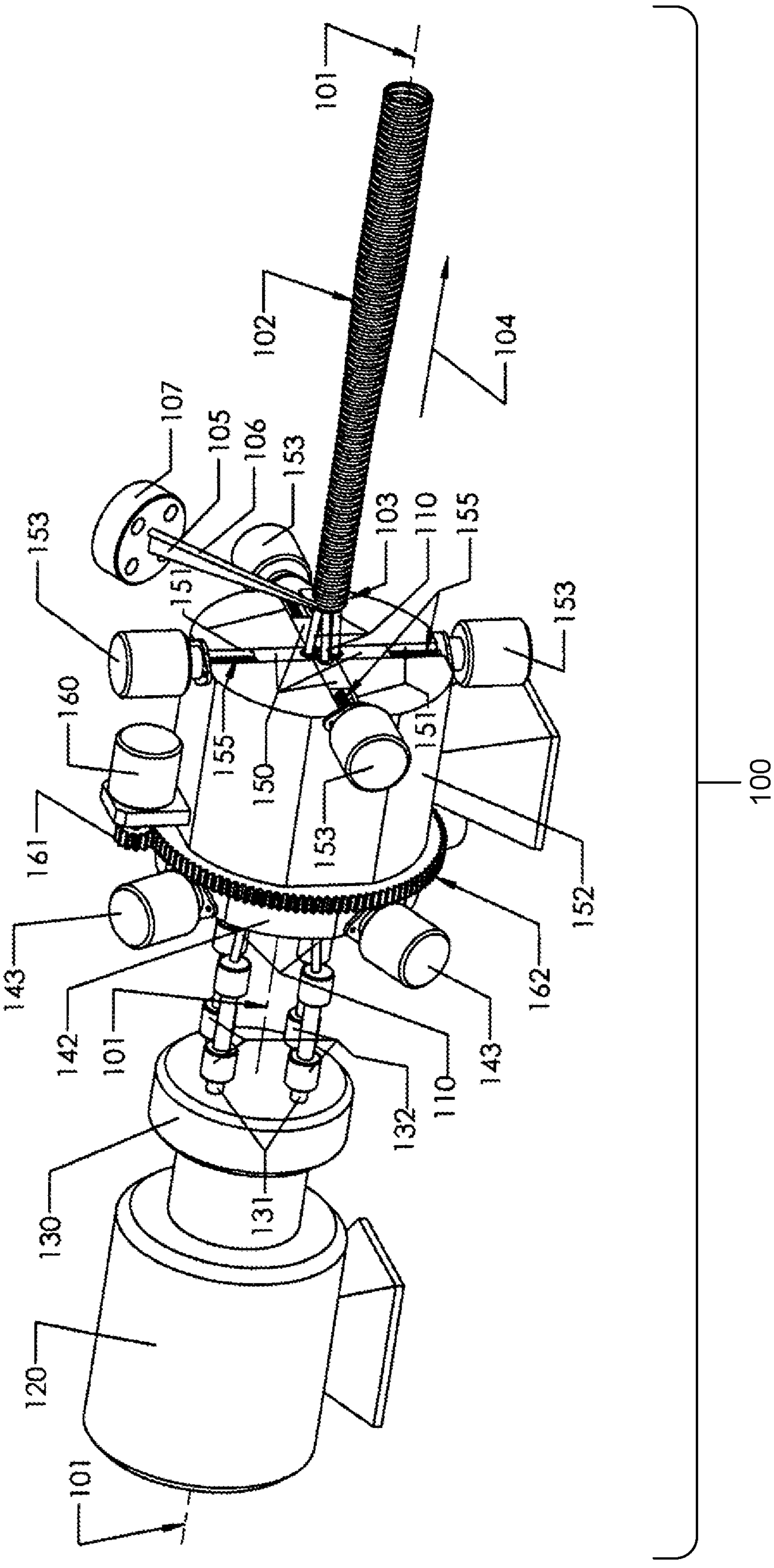
FIG. 4D is a perspective view of components of a hose making apparatus that may be adapted to make the hose of FIG. 4A.
Figure 4E:
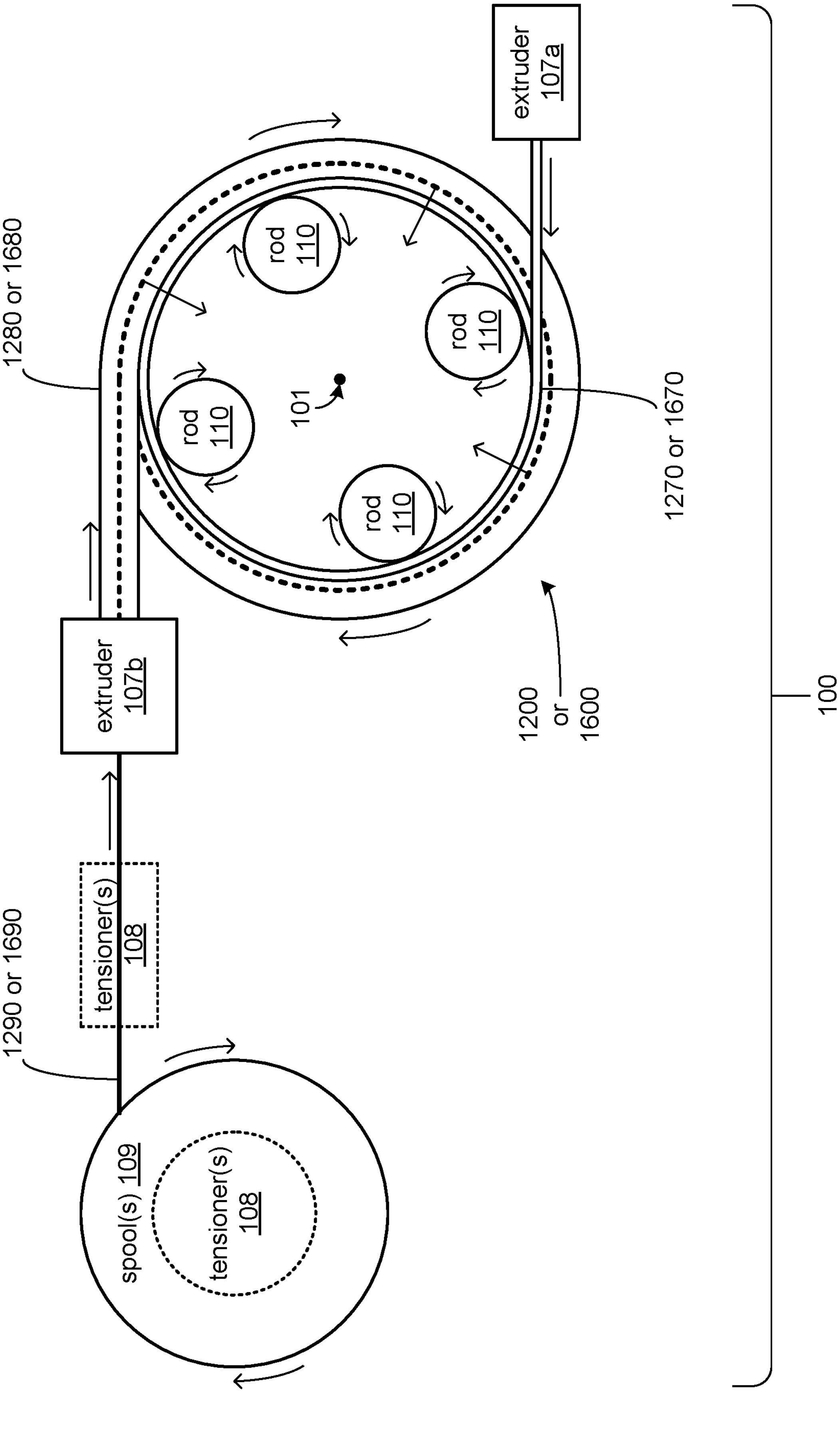
FIG. 4E is a block diagram of components of a hose making apparatus (e.g., the hose making apparatus of FIG. 4D) that has been adapted in accordance with one embodiment of adaptation to make the hose of FIG. 4A.

As depicted most clearly in FIGS. 4D and 4E, each of the hoses 1200 and/or 1600 may be formed using a modified variant of a typical hose manufacturing apparatus such as the depicted hose manufacturing apparatus 100. As will be familiar to those skilled in the art, such a hose manufacturing apparatus 100 may incorporate a set of rotating rollers 110 that may be canted in adjustable orientations relative to each other and relative to a central axis 101 to form a hose therearound from one or more spirally wound extruded lengths of plastics material. As will also be familiar to those skilled in the art, such hose forming typically entails wrapping at least one extruded length of webbing material for the wall of the hose and at least one extruded length of a support bead for at least one support helix of the hose. Alternatively, a single extrusion of material that combines the webbing and support bead may be used, as will also be familiar to those skilled in the art. An example of such hose manufacturing apparatus is disclosed in U.S. Pat. No. 9,505,164 issued Nov. 29, 2016 to Carl J. Garrett, which is incorporated herein by reference in its entirety, and from which FIG. 1 was copied to provide 4D of this present application. Additional aspects of hose making on which the making of the hoses 1200 and/or 1600 may also be based are disclosed in U.S. Pat. No. 9,308,698 issued Apr. 12, 2016 to Martin E. Forrester, and in U.S. Pat. No. 9,556,878 issued Jan. 31, 2017 to Carl J. Garrett, each of which is incorporated herein by reference in their entireties.

However, and turning to the subject of embodiments of the hoses 1200 and/or 1600 having support helixes 1280 and/or 1680 that include one or more wires 1290 and/or 1690, respectively, as part of enabling the forming of such hoses 1200 and/or 1600, such a typical hose making apparatus 100 may be modified to enable the extrusion of the flexible plastics material of the support helixes 1280 and/or 1680 around the heating wires 1290 and/or 1690, respectively, prior to the winding of the support helixes 1280 and/or 1680 onto the rollers 110.

Figure 4F:
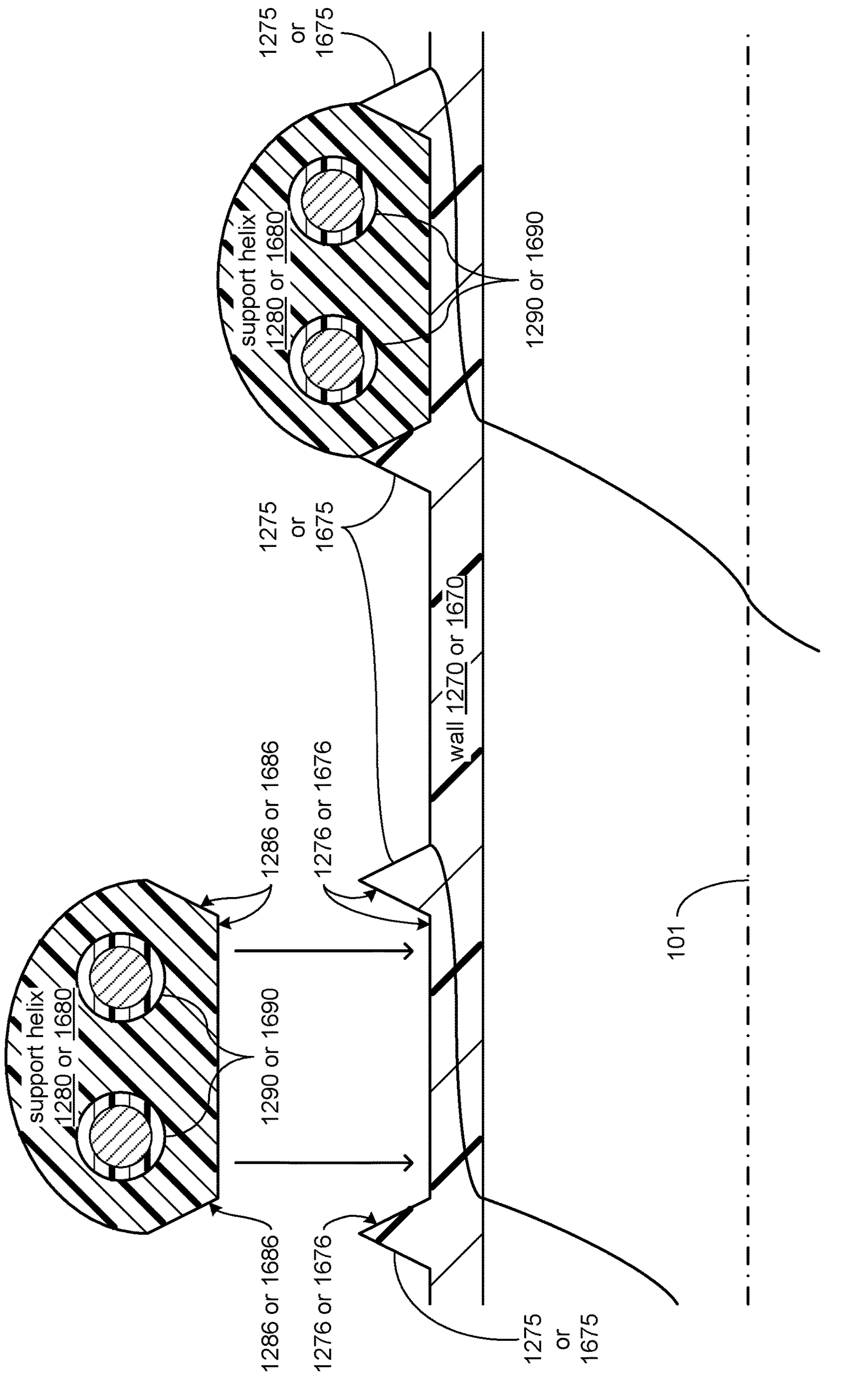
FIG. 4F is a cross-sectional view of a portion of the hose of FIG. 4A during the making thereof using the embodiment of adaptation of a hose making apparatus of FIG. 4E, showing details of combining the support helix and wall thereof.
Figure 4G:
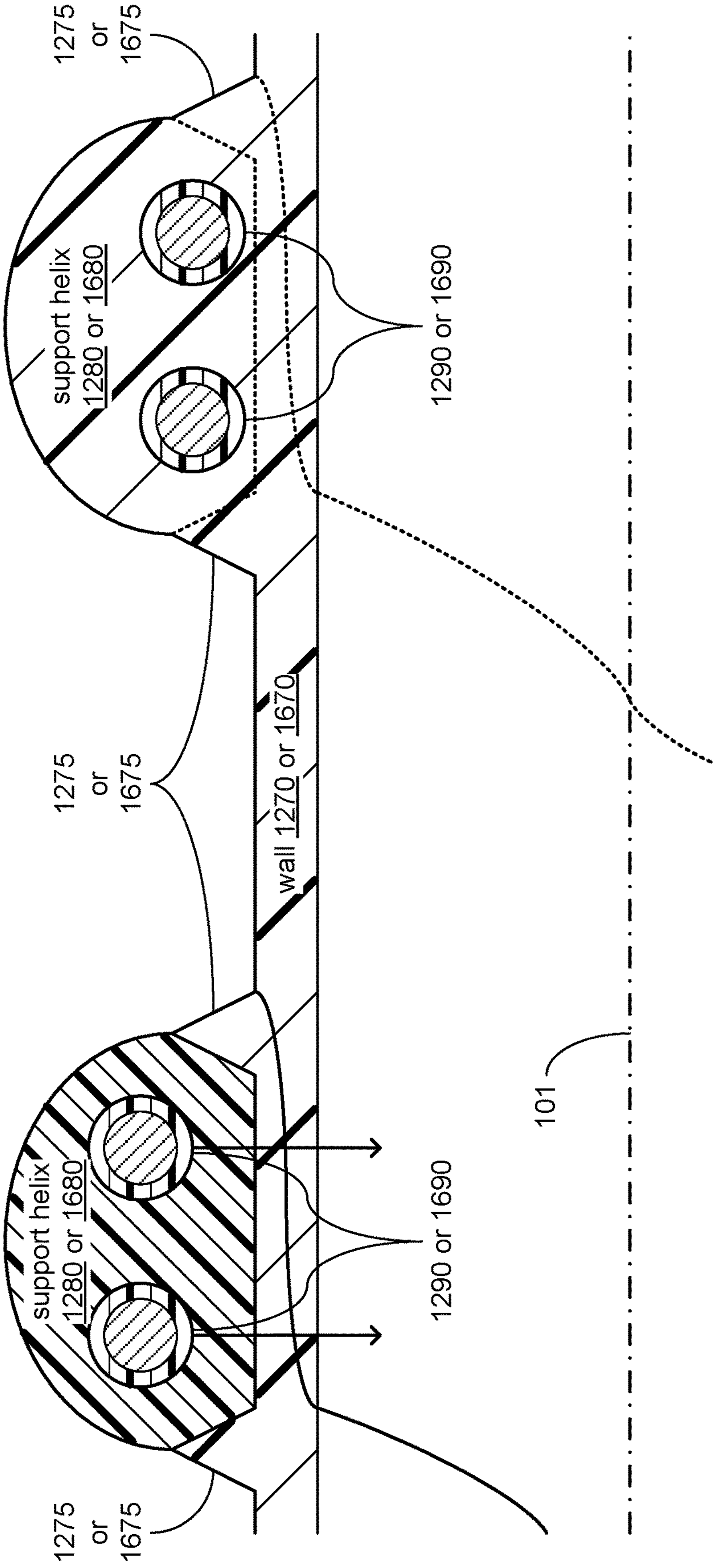
FIG. 4G is another cross-sectional view of the portion of the hose shown in FIG. 4F during the making thereof using the embodiment of adaptation of a hose making apparatus of FIG. 4E, showing details of the bonding of the support helix to the wall thereof and of the drawing of electrical wires thereof toward the interior of the hose.

As depicted most clearly in FIGS. 4E and 4G, as part of such modifications to the hose making apparatus 100, each of the heating wires 1290 or 1690 around which the plastics material of the support helix 1280 or 1680, respectively, is extruded may be tensioned, either by tensioner(s) 108 incorporated acting on the spool(s) 109 from which each of the heating wires 1290 or 1690 are unwound, or with tensioner(s) 108 acting on the heating wires 1290 or 1690 at location(s) interposed between the spool(s) 109 and the extruder 107*b*. This application of tension on the heating wires 1290 or 1680 ahead of the extruder 107*b* causes a "drawing down" of each of the heating wires 1290 or 1690 through portions of the material of the support helix 1280 or 1680, and closer towards the wall 1270 or 1670 as the hoses 1200 or 1600, respectively, are made. Stated differently, when the flexible material of each of the support helix 1280 or 1680 is extruded around the heating wires 1290 or 1690 that are to be embedded therein, the heating wires 1290 or 1690 may initially centered within the extruded plastics material. However, as the freshly extruded (and still somewhat molten and compliant) plastics material of the support helix 1280 or 1680 is wound about the set of rotating rods 110 of hose making apparatus 100, the tensioner(s) 108 may exert tension on the heating wires 1290 or 1690 to cause the heating wires 1290 or 1690 to be pulled radially inwardly toward the central axis 101 of the hose 1200 or 1600 being formed. This may cause the heating wires 1290 or 1690 to migrate within the flexible plastics material of the support helix 1280 or 1680 (again, while still somewhat molten and compliant) to a position within that plastics material that is closer to the interior of the hose 1200 or 1600, respectively, being formed than their initially centered position.

As depicted most clearly in FIGS. 4F and 4G, at least as part of enabling such use of tension to position the heating wires 1290 or 1690 as desired within the cross-section of the plastics material of the support helix 1280 or 1680, a particular portion of the external surface of the support helix

1280 or 1680 may be specifically selected to be designated as a bonding surface 1286 or 1686, respectively, that is to be put into contact with and bonded to a portion of the external surface of the wall 1270 or 1670 of the hose 1200 or 1600 that is designated as the corresponding bonding surface 1276 or 1676. Thus, as the support helix 1280 or 1680 is spirally wrapped around the external surface of the wall 1270 or 1670, it is these designated bonding surfaces 1286 and 1276, or 1686 and 1676, of each that are brought into contact with each other and bonded to each other.

Turning more specifically to FIG. 4F, as depicted, the portion of the external surface of the support helix 1280 or 1680 that is selected to be bonding surface 1286 or 1686, respectively, may be specifically shaped and/or otherwise specifically configured for being bonded to the corresponding bonding surface 1276 or 1676 of the hose 1270 or 1670, respectively. By way of example, and as specifically depicted, the bonding surface 1286 or 1686 may be formed to be a flat surface to accommodate the similarly flat configuration of the bonding support surface 1276 or 1676, respectively. Alternatively, and also by way of example (though not specifically depicted), the bonding surface 1286 or 1686 may be formed to define a surface of convex or concave configuration to accommodate a corresponding concave or convex, respectively, configuration of the bonding surface 1276 or 1676, respectively.

Alternatively or additionally, and as also depicted, the cross-section of the length of extruded material from which the wall 1270 or 1670 is formed may additionally include a pair of radially outwardly projecting guides 1275 or 1675, respectively, to aid in guiding the bonding surface 1286 or 1686 of the support helix 1280 or 1680 into contact with the corresponding bonding surface 1276 or 1676 of the wall 1270 or 1670, respectively. As also depicted, such guides 1275 or 1675 may define additional bonding surfaces 1276 or 1676, respectively, that are meant to come into contact with, and to become bonded to, corresponding additional bonding surfaces 1286 or 1686 formed on the exterior surface of the support helix 1280 or 1680, respectively. Thus, as the support helix 1280 or 1680 is spirally wrapped around the external surface of the wall 1270 or 1670, there may be multiple corresponding pairs of bonding surfaces 1276 and 1286, or 1676 and 1686, that are brought into contact with each other and bonded to each other.

Turning more specifically to FIG. 4G, and regardless of whether such guide projections are provided, following the laying down of the support helix 1280 or 1680 onto the external surface of the wall 1270 or 1670 such that the bonding surfaces 1276 and 1286, or 1676 and 1686 are put into contact with and bonded to each other, the aforedescribed tension causes inward migration of the heating wires 1290 or 1690 within the flexible (and still somewhat molten and compliant) plastics material of the support helix 1280 or 1680 toward the wall 1270 or 1670 (which may be less molten or no longer molten, and which may be used to stop the migration at the external surface of the wall 1270 or 1670), toward the interior of the hose 1200 or 1600, and toward the central axis 101 of the hose 1200 or 1600, respectively.

This technique of causing a radially inward draw down may be deemed preferable to attempting to position the heating wires 1290 or 1690 within the cross-sections of the extrusions of the helixes 1280 or 1680 at such locations during extrusion. This technique of causing a radially inward draw down may also provide the flexibility to allow variations in placement of the heating wires 1290 or 1690 further radially inward and/or further radially outward within the cross-sections of the helixes 1280 or 1680, respectively, as part of creating different variants of the hoses 1200 or 1600 that may have different heating characteristics (and/or other characteristics that may be influenced by placement of the heating wires 1290 or 1690 within the helixes 1280 or 1680, respectively).

FIGS. 5A through 5J, taken together, depict various aspects of at least one alternate embodiment of a process for making the inspiratory hose 1200 and/or the expiratory hose 1600, including aspects of forming the support helixes 1280 and/or 1680 thereof to include one or more electrical wires 1290 and/or 1690, respectively. As with FIGS. 4A-G, it should be noted that, although, so far, the helixes 1280 and 1680 are depicted as each incorporating a pair of heating wires 1290 and 1690, respectively, other embodiments of the hoses 1200 and/or 1600 are possible in which different quantities of electrical wires (whether heating wires, or other types of electrical wires, and/or wires used for other purposes) may be incorporated into the support helixes 1280 and/or 1680, respectively, as well as other embodiments in which there may be multiple helixes that each carry one or more different electrical wires (again, whether heating wires, or not). Again, it should also be noted that still other embodiments of the hoses 1200 and/or 1600 are possible in which different quantities of lumens 1289 and/or 1689 may be incorporated into the helixes 1280 and/or 1680, respectively, as well as other embodiments in which there may be multiple helixes that each carry one or more different sizes of lumens. And again, it should further be noted that yet other embodiments of the hoses 1200 and/or 1600 are possible in which there may be any of a variety of combinations of lumens 1289 and/or 1689, and of wires 1290 and/or 1690.

As in the embodiment of a hose making process of FIGS. 4A-G, in the various alternate embodiments of a hose making process of FIGS. 5A-J, each of the hoses 1200 and/or 1600 may be formed using a modified variant of a typical hose manufacturing apparatus such as the hose manufacturing apparatus 100 introduced above in connection with FIG. 4D. However, while the final position of one or more electrical wires 1290 or 1690 within the support helix 1280 or 1680 is set while the hose 1200 or 1600 is formed on a modified version of the hose manufacturing apparatus 100 in the process of FIGS. 4A-G, in the alternate embodiments of FIGS. 5A-J, the final position of one or more electrical wires 1290 or 1690 within the support helix 1280 or 1680 is set prior to the support helix 1280 or 1680 being introduced at a modified version of the hose manufacturing apparatus 100. Similarly, the various alternate embodiments of a hose making process of FIGS. 5A-J may be used to similarly set the final position of one or more lumens 1289 or 1689 within the support helix 1280 or 1680 prior to the support helix 1280 or 1680 being introduced at a modified version of the hose manufacturing apparatus 100. And also similarly, the various alternate embodiments of a hose making process of FIGS. 5A-J may be used to set the final positions of a combination of one or more wires 1290 or 1690, and one or more lumens 1289 or 1689 within the support helix 1280 or 1680 prior to the support helix 1280 or 1680 being introduced at a modified version of the hose manufacturing apparatus 100. The incorporation of one or more lumens 1289 or 1689 into a support helix 1280 or 1680 of a hose 1200 or 1600, either in addition to or in lieu of one or more wires 1290 or 1690, respectively, may advantageously serve a variety of purposes. For example, in response to increasing efforts to make plastic products more easily recyclable, it may be deemed desirable to entirely replace the use of electrical wires 1290 or 1690 within a hose 1280 or 1680 with one or more lumens 1289 or 1689 that are formed within one or more support helixes 1280 or 1680, respectively, thereof. Thus, the cross-section(s) of one or more support helixes 1280 or 1680 of a hose 1200 or 1600 may be shaped to define one or more lumens 1289 or 1689 therein that may be used, in lieu of wires 1290 or 1690, to carry gas or liquid that serve to heat or cool the hose 1200 or 1600, and/or that serve to convey control signals therethrough.

By way of a specific example, and as already discussed above, it is often necessary to heat a breathing gas that is conveyed from a medical device, through a hose and to a mask, cannula or stoma of a patient as an approach to preventing moisturizing water vapor that may be included therein from condensing out such a gas. As also already discussed above, this is often the impetus for incorporating heating wires into such a hose in at least some manner. However, it has been found that replacing wires with a flow of a heated liquid (e.g., heated water) that is conveyed through a separate passage along the length of such a hose can provide more consistent and/or even heating of the breathing gas, which may serve to prevent the development of locations along the length of such a hose where the temperature may drop to a level that enables condensing to occur.

By way of another specific example, it may be that, in lieu of incorporating one or more electrical wires 1290 or 1690 to convey control signals through the support helix 1280 or 1680 of a hose 1200 or 1600, respectively, one or more lumens 1289 or 1689 may be used to do so. Thus, it may be that a remotely located valve for regulating a flow of a gas or liquid, and/or for switching between different gases and/or liquids may be controlled pneumatically and/or hydraulically through one or more of such lumens 1289 or 1689. Specifically, a single lumen 1289 or 1689 may be used to alternately convey a higher or lower pressure of a gas to cause opening, closing and/or adjusting of a valve, or may be used to cause switching between, and/or cause a change in a ratio of mixing of, different gases and/or liquids. Alternatively, it may be that a differential of pressures conveyed through a pair of lumens 1289 or 1689 are used. Additionally, it may be that still another lumen 1289 or 1689 is used to convey a varying amount of pressure or flow of a gas or liquid to provide confirmation of a current state of such a valve.

Also for example, under some circumstances, it may be deemed desirable to incorporate a sensor that requires access to a gas or liquid that is conveyed by a hose 1280 or 1680 into a component or device that is connected to by an end of the hose 1280 or 1680, instead of incorporating that sensor into the hose 1280 or 1680, itself (or otherwise positioning that sensor along the length of the of the hose 1280 or 1680). Again, this may be due to a desire to make the hose 1280 or 1680 more easily recyclable when it is discarded. To enable this, one or more lumens 1289 or 1689 may be incorporated into one or more support helixes 1280 or 1680 of a hose 1200 or 1600 to bring a sampling of the gas or liquid that is conveyed by the 1200 or 1600, respectively, to the location of that sensor.

By way of a specific example, and as already discussed above, a temperature, humidity and/or pressure sensor may be positioned along the length of a hose, or at a distant end of a hose, and then wires 1290 or 1690 may be incorporated into the helix 1280 or 1680 thereof to convey signals indicative of what is detected thereby. As an alternative, it may be that such a sensor is incorporated into a device to which the hose is 1200 or 1600 is connected, and then a lumen 1289 or 1689 is used to bring, to that sensor, a sample of the gas or liquid that is conveyed through the passage defined by the wall 1270 or 1670 of the hose 1200 or 1600. Thus, in this way, instead of locating a sensor in the vicinity of the mask, cannula or stoma of a patient, a lumen 1289 or 1689 incorporated into the support helix 1280 or 1680 of the hose 1200 or 1600 that is connected to that mask, cannula or stoma may be used to bring a sample of the breathing gas that is collected at that location back to the medical device(s) serving as the source of that breathing gas.

Additionally for example, it may be deemed desirable to augment the conveyance of a main flow of gas or liquid through the passage that is defined by the wall 1270 or 1670 of a hose 1200 or 1600 with one or more additional passages provided by one or more lumens 1289 or 1689 provided within the support helix 1280 or 1680 of that hose 1200 or 1600, respectively. By way of a specific example, it may be deemed desirable to convey one or more additional gases and/or liquids through such lumen(s) 1289 or 1689 to enable a mixing of multiple gases and/or liquids at a device or component at a particular location. Thus, it may be that multiple breathing, humidification and/or medicinal gases and/or liquids may be conveyed to the face mask, cannula or stoma of a patient, where mixing thereof may take place just before the resulting mixture enters the patient's body.

By way of another specific example, it may be deemed desirable to augment the main flow of a gas or liquid through the passage defined by the wall 1270 or 1670 of a hose 1200 or 1600 in one direction with a return flow path by which a portion of that same gas or liquid that is so conveyed is conveyed in the opposite direction. This may be deemed desirable where there the main flow of gas or liquid within the wall 1270 or 1670 of such a hose 1200 or 1600 is not a continuous flow such that there are periods of time during which that gas or liquid is caused to remain motionless therein. It may be that allowing a gas or liquid to remain stationary within a hose presents the risk of allowing components of the gas or liquid that were mixed together to separate (e.g., via precipitation, development of condensation, etc.). The provision of such a return flow path may provide a mechanism by which a constant circulation of the gas or liquid is always maintained such that there is always at least a predefined minimum degree of flow through of the gas or liquid through the passage defined by the wall 1270 or 1670.

Regardless of whether a support helix 1280 or 1680 for a hose incorporates one or more wires 1290 or 1690, or incorporates one or more lumens 1289 or 1689, or incorporates a combination of both, where there a hose 1280 or 1680 includes more than one support helix 1280 or 1680, it may be that different ones of such multiple support helixes 1280 or 1680 are marked or otherwise provided with differing colors. Such differing colors may serve as a color code of a particular gas or liquid that is conveyed in a lumen 1289 or 1689 therethrough, and/or may serve as a color code of a particular function performed by or signal carried by a wire 1290 or 1690 therethrough.

Figure 5A:
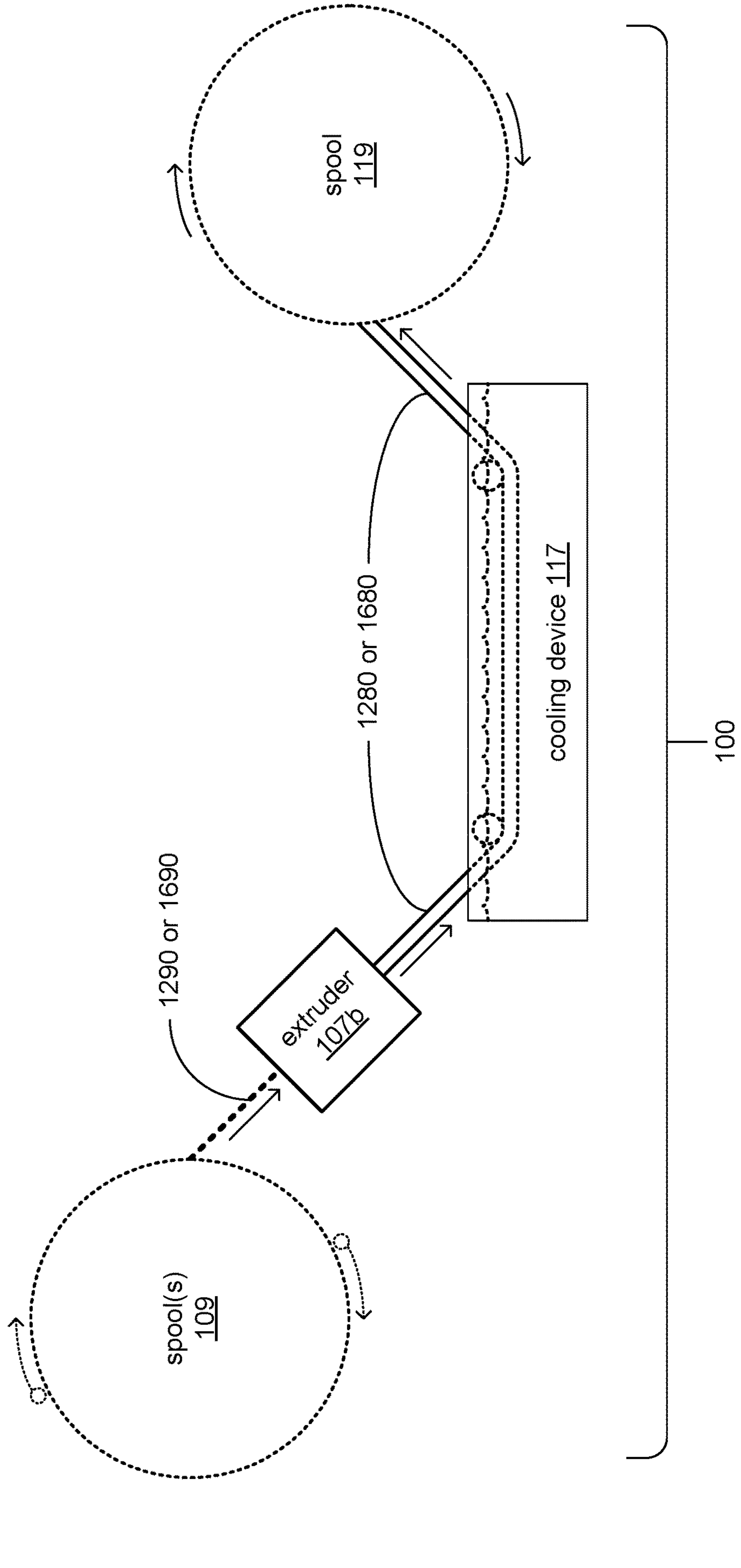
FIGS. 5A and 5B, together, provide a block diagram of components of a hose making apparatus (e.g., the hose making apparatus of FIG. 4C) that has been adapted in accordance with an alternate embodiment of adaptation to make the hose of FIG. 4A (or the variant thereof of FIG. 4C).

Turning to FIG. 5A, a bead of plastics material may be extruded by the extruder 107*b* to become the support helix 1280 or 1680 of a hose 1200 or 1600, respectively. Where such a support helix 1280 or 1680 is to include one or more electrical wires 1290 or 1690, one or more spools 109 of the electrical wires 1290 or 1690 may be fed into the extruder 107*b* to enable the bead of plastics material to be extruded therearound as the electrical wires 1290 or 1690, respectively, are fed therethrough. Alternatively or additionally, where such a support helix 1280 or 1680 is to include one or more lumens 1289 or 1689, the extruder 107*b* may be configured to impart a cross-section to the bead of plastics material that includes one or more hollow regions (or bores) in the cross-section, where each hollow region serves to define the cross-sectional shape and size of one of the lumens 1289 or 1689, respectively.

Regardless of whether the newly formed bead of support helix 1280 or 1680 is to include any electrical wires 1290 or 1690, and regardless of whether the newly bead of support helix 1280 or 1680 is to include any lumens 1289 or 1689, the newly formed bead of support helix 1280 or 1680 may then be fed through a cooling device 117 to be cooled sufficiently to cause the plastics material thereof to be hardened enough to prevent any electrical wires 1290 or 1690 from migrating within the plastics material of the support helix 1280 or 1680, respectively, and/or to prevent any lumens 1289 or 1689 from becoming misshapen and/or reduced in size.

In some embodiments, the cooling device 117 may be a trough or other elongate container of water or other liquid through which the newly formed bead of support helix 1280 or 1680 is routed. In some of such embodiments, the water or other liquid may be maintained by exposure to the surrounding environment at an ambient room temperature that is far below the temperature at which the newly formed bead of support helix 1280 or 1680 emerges from the extruder 107*b*, where such an ambient room temperature is sufficiently cool as to cause sufficient hardening of the plastics material. However, in others of such embodiments, the water or other liquid may be actively cooled to a still lower temperature where such a lower temperature is deemed necessary to cause sufficient hardening of the plastics material. The temperature of the water or other liquid may be based, at least in part, on the rate at which the newly formed bead of support helix 1280 or 1680 is routed through the cooling device 117 so as to ensure that sufficient cooling is able to take place, while at the same time, avoiding excessive cooling such that the plastics material is caused to respond by hardening and/or contracting in size sufficiently quickly as to cause cracking or other undesirable changes thereto.

Following such cooling of the newly formed bead (and with the positions of any wires 1290 or 1690 thereby set therein, and/or with the shape and/or size of any lumens 1289 or 1689 thereby set therein), the newly formed bead of support helix 1280 or 1680 may either be immediately used in making a hose 1200 or 1600, respectively, or may be temporarily stored in preparation for making a hose 1200 or 1600 at a later time. More specifically, and as depicted, the newly formed bead of support helix 1280 or 1680 may be wound about another spool 119 in preparation for storage.

It may be deemed desirable to store multiple rolls of differing types of support helix 1280 or 1680, whether on spools 119 or in some other manner of storage, so as to have a selection of differing types of support helix 1280 or 1680 available to enable a form of just-in-time manufacturing of a hose 1200 or 1600 with a dynamically selected type of support helix 1280 or 1680. This may obviate the need to, instead, store a variety of types of hose 1200 or 1600 that may be differentiated solely by the type of support helix 1280 or 1680 that is incorporated therein. When the need arises to make a particular type hose 1200 or 1600 that includes a particular type of support helix 1280 or 1680, respectively, a roll of that particular type of support helix 1280 or 1680 may then be retrieved and brought to a modified variant of the hose manufacturing apparatus 100 to be used in making the needed hose 1200 or 1600.

Figure 5B:
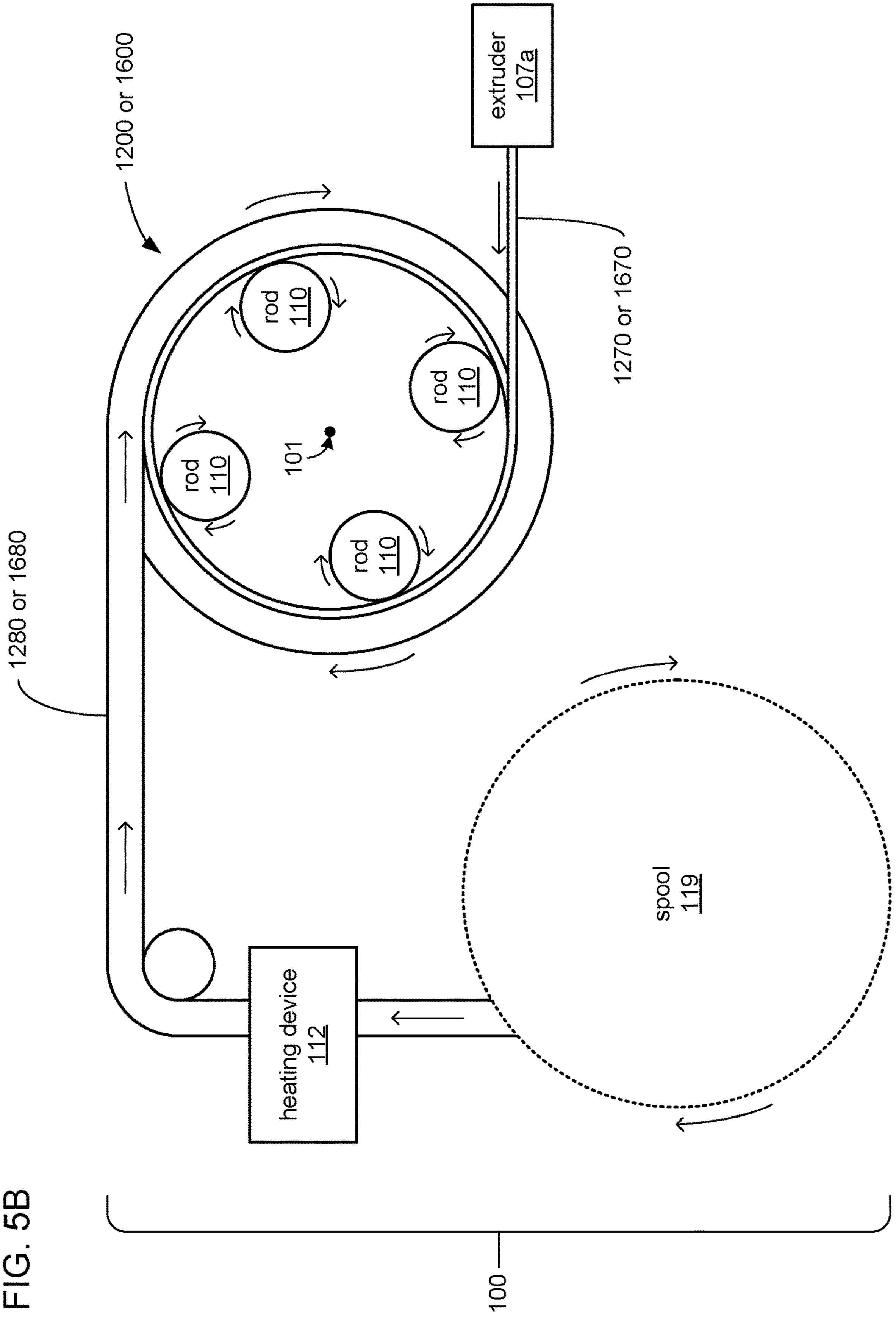

Turning to FIG. 5B, such modifications that may be made to the hose manufacturing apparatus 100 may include the addition of a heating device 112 to re-heat a support helix 1280 or 1680 as it is supplied to the hose manufacturing apparatus 100 as part of manufacturing a hose 1200 or 1600, respectively. As the bead of support helix 1280 or 1680 is fed through the heating device 112, it is re-heated to a controlled degree that causes outer surface portions of the plastics material thereof (e.g., the bonding surface 1286 or 1686) to become slightly molten such that those outer surface portions are softened and become tacky. The degree of re-heating may be controlled to avoid overheating to such an extent that inner portions of the plastics material of the bead of support helix 1280 or 1680 in the vicinity of any electrical wires 1290 or 1690 becomes molten such that they are able to migrate to new positions within that plastics material, and/or to avoid overheating to such an extent that inner portions of the plastics material of the bead of support helix in the vicinity of any lumens 1289 or 1689 becomes molten such that the shape and/or size thereof are caused to change.

By making outer surface portions of the plastics material of the bead of support helix 1280 or 1680 tacky (e.g., the bonding surface 1286 or 1686), the now re-heated bead is caused to readily bond to the exterior of the wall 1270 or 1670 of the hose 1200 or 1600 that is being formed from the web of plastics material freshly extruded by the extruder 107*a* (e.g., the bonding surfaces 1276 and 1286, or 1676 and 1686, are caused to readily bond). Such softening of outer surface portions of the bead of support helix 1280 or 1680 also serves to make the bead less resistant to being wrapped around the exterior of the wall 1270 or 1670 of the hose 1200 or 1600, respectively, that is being formed with the hose manufacturing apparatus 100. More specifically, such softening of outer surface portions serves to make the bead of support helix 1280 or 1680 less resistant to being bent into the particular radius of curve needed for it to be wrapped around the exterior of the wall 1270 or 1670 of the hose 1200 or 1600, respectively, that is being so formed. In this way, the separately formed bead of support helix 1280 or 1680 becomes the support helix 1280 or 1680 of the hose 1200 or 1600, as depicted in FIG. 5D, thereby completing the formation thereof.

Figure 5C:
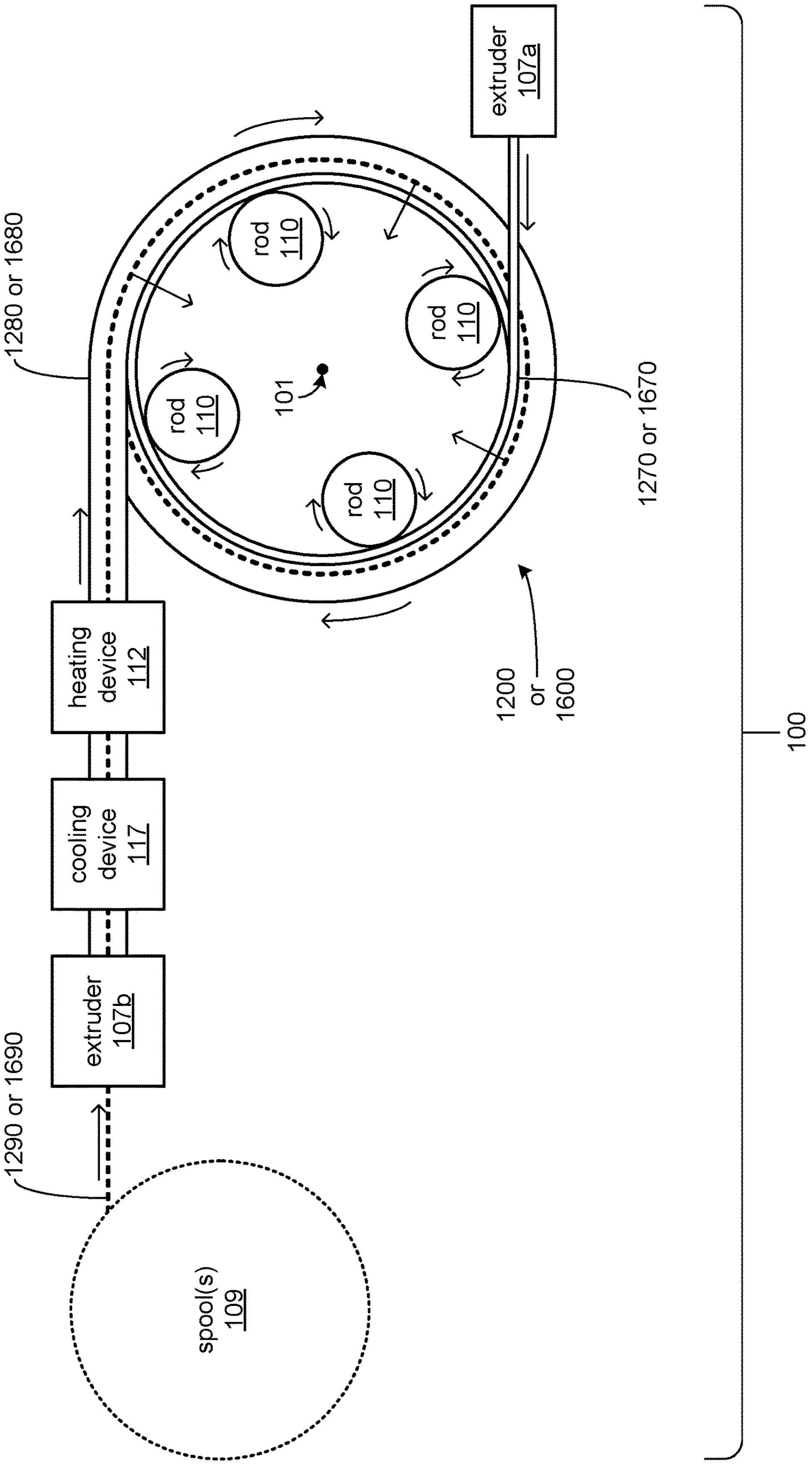
FIG. 5C is a block diagram of components of a hose making apparatus (e.g., the hose making apparatus of FIG. 4C) that has been adapted in accordance with another alternate embodiment of adaptation to make the hose of FIG. 4A (or the variant thereof of FIG. 4C).
Figure 5D:
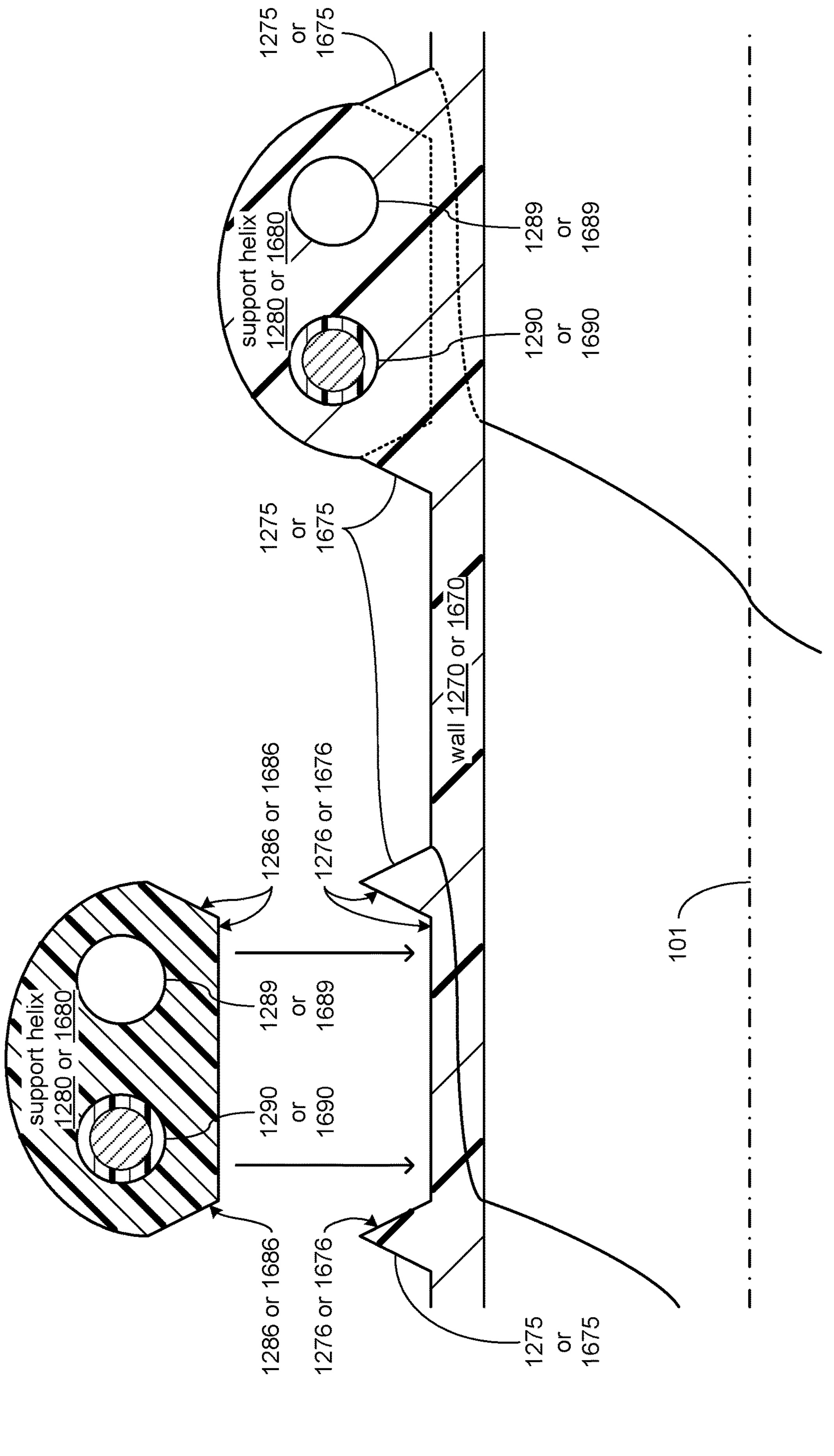
FIG. 5D is a cross-sectional view of a portion of the hose of FIG. 4A during the making thereof using the embodiment of adaptation of a hose making apparatus of FIGS. 5A-B or of FIG. 5C, showing details of combining the support helix and wall thereof.

Turning to FIG. 5C, as an alternative to storing the bead of support helix 1280 or 1680 after it has been formed using the extruder 107*b* and then cooled by the cooling device 117, the newly formed bead of support helix 1280 or 1680 may be immediately and directly fed to the heating device 112 to have exterior portions of the plastics material thereof (e.g., the bonding surface 1286 or 1686) re-heated as has just been described. In this case, the winding of the newly formed and cooled bead of support helix 1280 or 1680 onto the depicted spool 119 (as depicted in FIG. 5A), and the subsequent unwinding therefrom (as depicted in FIG. 5B), may be entirely obviated. Instead, the extruder 107*b* and the cooling device 117 may be located in the vicinity of the hose manufacturing apparatus 100, along with the heating device 112. And, in this way, the bead of support helix 1280 or 1680 becomes the support helix 1280 or 1680 of the hose 1200 or 1600, as depicted in FIG. 5D.

Figure 5E:
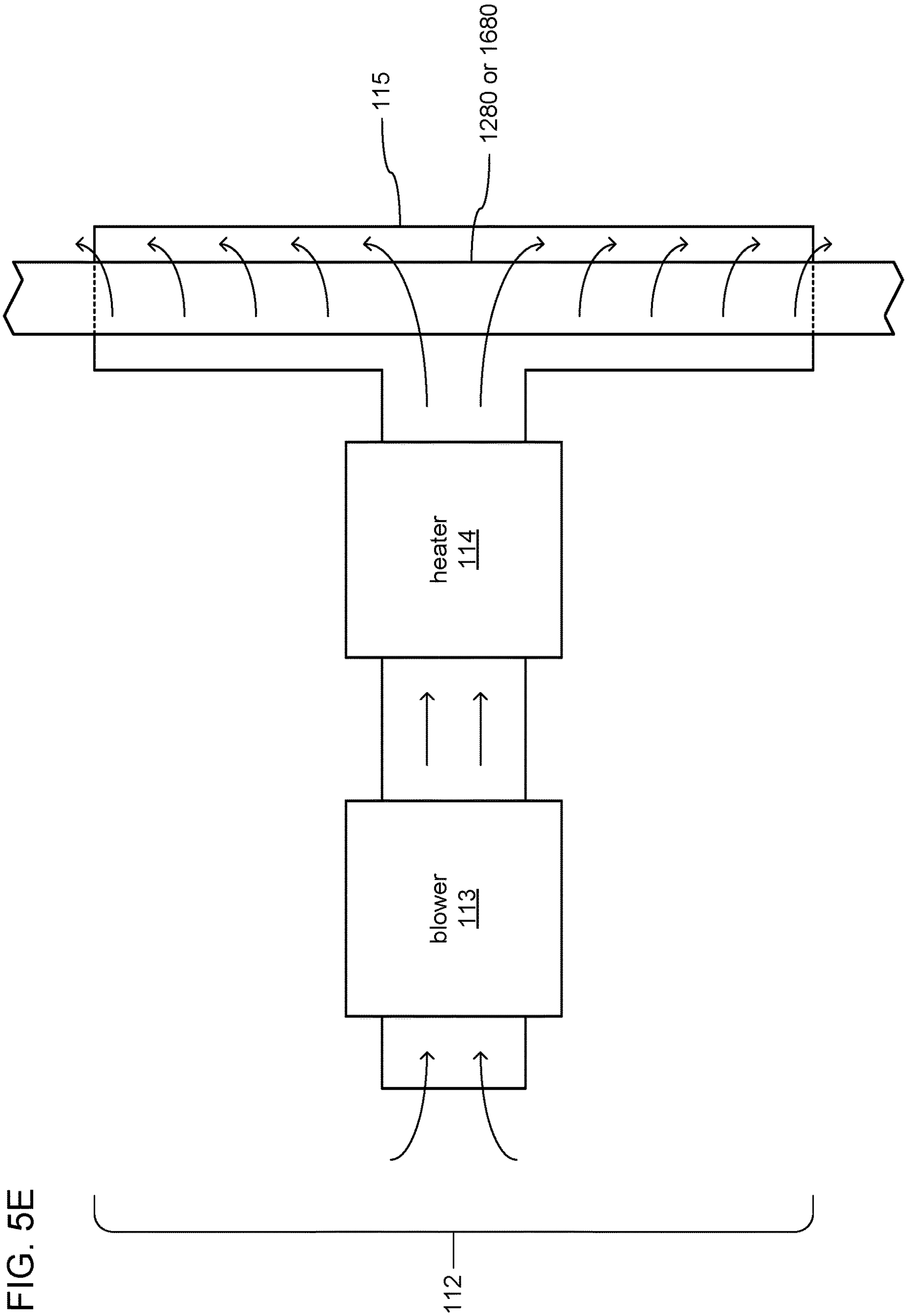
FIG. 5E is a block diagram of components of a heating device that may be incorporated into the embodiment of adaptation of the hose making apparatus of FIGS. 5A-B or of FIG. 5C.

Turning to FIG. 5E, regardless of whether the bead of support helix 1280 or 1680 formed as depicted in FIG. 5A is used immediately in forming a hose 1200 or 1600 (as depicted in FIG. 5C), or is stored for later use in forming a hose 1200 or 1600 at a later time (as depicted in FIGS. 5A-B), in some embodiments, the heating device 112 may employ air that has been heated to a controlled degree in re-heating the bead of the support helix 1280 or 1680 at whatever time it is brought to the hose manufacturing apparatus 100 to form a hose 1200 or 1600, respectively. More specifically, the heating device 112 may include a heating tube 115 through which the bead of support helix 1280 or 1680 is fed on the way to being provided to the hose manufacturing apparatus 100, and into which the hot air is blown to heat the support helix 1280 or 1680 as it passes therethrough. The heating device 112 may include a blower 113 to pull in surrounding ambient air, and may include a heater 114 to heat that ambient air as it is blown through the heater 114 and into the heating tube 115 by the blower 113.

The temperature and/or volume of the hot air blown into the heating tube 115 may be adjusted to control the degree to which outer surface portions of the bead of support helix 1280 or 1680 are caused to become molten. Such parameters as the inner diameter and/or length of the heating tube 115, and/or the temperature and/or volume of the hot air blown into the heating tube 115 may be based on such factors as the cross-section of the bead of support helix 1280 or 1680, and/or the speed at which the bead is fed through the heating tube. The speed at which the bead of support helix 1280 or 1680 is fed through the heating tube 115 may be entirely controlled by the speed at which bead is to be fed to the hose manufacturing apparatus 100 to form a hose 1200 or 1600, respectively.

Figure 5G:
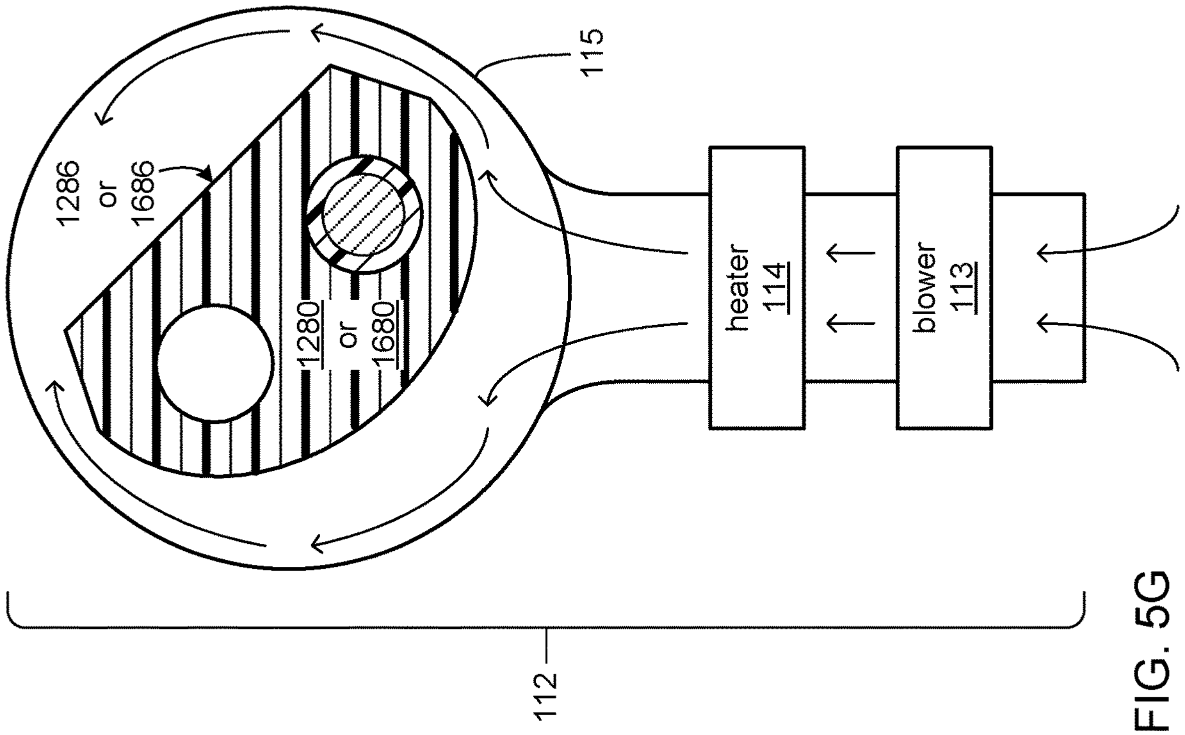
FIG. 5G is still another block diagram of the heating device of FIG. 5E.
Figure 5F:
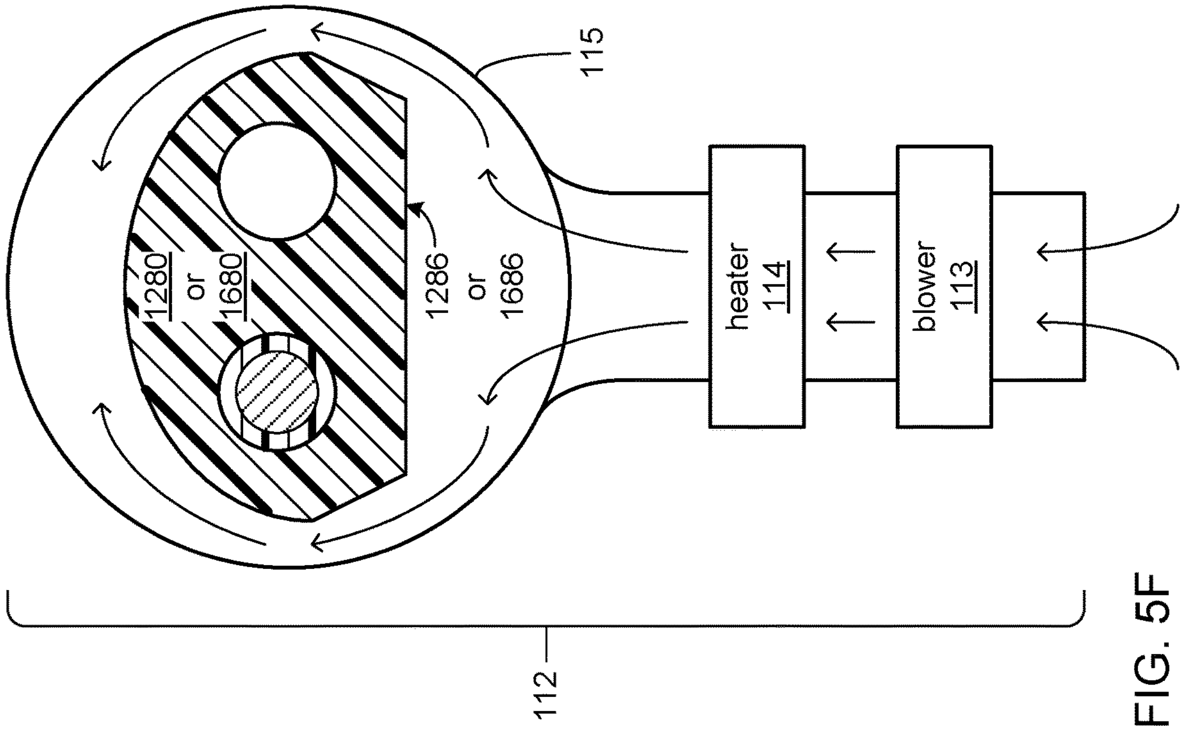
FIG. 5F is another block diagram of the heating device of FIG. 5E.

Turning to FIG. 5F, it has been found that the shape of the cross-section of the heating tube 115 need not match the shape of the cross-section of the particular bead of support helix 1280 or 1680 that is fed therethrough. It has also been found that the inner diameter of the heating tube 115 need not be selected to closely surround the outer surface portions of the bead of support helix 1280 or 1680 that is fed therethrough. This enables the use of a heating tube 115 that has a relatively simple, generally round cross-section with an inner diameter that may be large enough to accommodate a relatively wide variety of beads of support helix 1280 or 1680 of a wide variety of cross-sectional shapes and sizes.

To aid in providing relatively even re-heating of outer surface portions of a bead of support helix 1280 or 1680 fed through the heating tube 115, the heating tube 115 may be shaped and/or sized, and/or the location within the heating tube 115 at which the hot air enters may be shaped and/or sized, to cause one or more spiraling vortices of hot air to be formed within the heating tube 115 that may serve to urge the support helix 1280 or 1680 to tend to remain centered within the heating tube 115 as it passes therethrough to better enable exposure of the entirety of the outer surface thereof to the hot air.

The lack of need to employ differing heating tubes 115 of differing cross-sectional shapes and/or differing diameters to accommodate a wide variety of types of support helix 1280 or 1680 may enable a single hose manufacturing apparatus 100 that has been modified with at least the addition of the heating device 112 to be more easily used in making a wide variety of different types of the hoses 1200 or 1600 employing a wide variety of different types of the support helixes 1280 or 1680. Specifically, the heating device 112 and/or the heating tube 115 becomes a component thereof that need not be physically swapped or otherwise physically altered when transitioning from making one type of hose 1200 or 1600 with a support helix 1280 or 1680 having one cross-section to making another type of hose 1200 or 1600 with another support helix 1280 or 1680 having a different cross-section, beyond possibly needing to reposition the heating device 112 to accommodate such other differences as differences in the diameters of the two types of hose 1200 or 1600, respectively.

Turning to FIG. 5G, the lack of need to in some way match a particular shape and/or diameter of the heating tube 115 with a particular shape and/or diameter of cross-section of a support helix 1280 or 1680, along with the ability to provide relatively even re-heating of outer surface portions of a support helix 1280 or 1680, also obviates the need to in some way align the orientation of the heating tube 115 and/or the direction from which hot air enters the heating tube 115 in some particular way to the orientation of the cross-section of a support helix 1280 or 1680. Stated differently, the direction in which a bonding surface 1286 or 1686 of a support helix 1280 or 1680 is facing as it passes through the heating tube 115 can be entirely ignored such that heating tube 115 need not be rotated to cause the direction from which hot air enters the heating tube 115 to be oriented in a particular manner relative to the direction in which the that bonding surface 1286 or 1686 faces. This may obviate the need to in any way reposition the heating tube 115 relative to other components of the manufacturing apparatus 100, except possibly where there is a change in the diameter of the hose 1200 or 1600 to be made.

Thus, it is not necessary to orient a support helix 1280 or 1680 as it is routed through the heating tube 115 to cause a bonding surface 1286 or 1686 thereof to directly face the oncoming flow of hot air entering the heating tube 115, or to cause the bonding surface 1286 or 1686, respectively, to face in any other particular direction relative to that hot air flow. And therefore, the support helix 1280 or 1680 may be oriented in any direction within the heating tube 115, or to face 180 degrees away from that hot air flow, or to face in any other particular direction relatively to that hot air flow (as depicted in FIG. 5G).

Still further, the same lack of need to in some way match a particular shape and/or diameter of the heating tube 115 with a particular shape and/or diameter of cross-section of a support helix 1280 or 1680, along with the ability to provide relatively even re-heating of outer surface portions of a support helix 1280 or 1680, also serves to enable the re-heating of types of support helix 1280 or 1680 that may not have a specific portion of the exterior thereof that is designated to serve as a bonding surface 1286 or 1686, respectively. Such a circumstance may arise, for example, where a support helix 1280 or 1680 is used that has a circular cross-section or other cross-section that does not define a distinct portion of its exterior that may be shaped to in some particular way correspond to the shape of a particular portion of the exterior of the wall 1270 or 1670 of a hose 1200 or 1600, respectively. Such a circumstance may also arise, for example, where a support helix 1280 or 1680 is used that has an irregularly-shaped cross-section and/or a cross-section that frequently changes along its length.

However, in embodiments in which a support helix 1280 or 1680 is used that has a cross-section that does define a distinct bonding surface 1286 or 1686, respectively, it may be deemed desirable to use a different embodiment of the heating device 112 that is configured to avoid re-heating the entirety of the exterior of the support helix 1280 or 1680. More specifically, it may be deemed desirable to limit the re-heating of a support helix 1280 or 1680 to just the bonding surface 1286 or 1686 to the extent needed to cause the bonding surface 1286 or 1686 to become molten, while avoiding (at least to the extent possible) re-heating other portions of the exterior of the support helix 1280 or 1680 (e.g., avoiding heating at least a portion of the exterior that is on a side of the exterior that is opposite the side that includes the bonding surface 1286 or 1686).

Figure 5I:
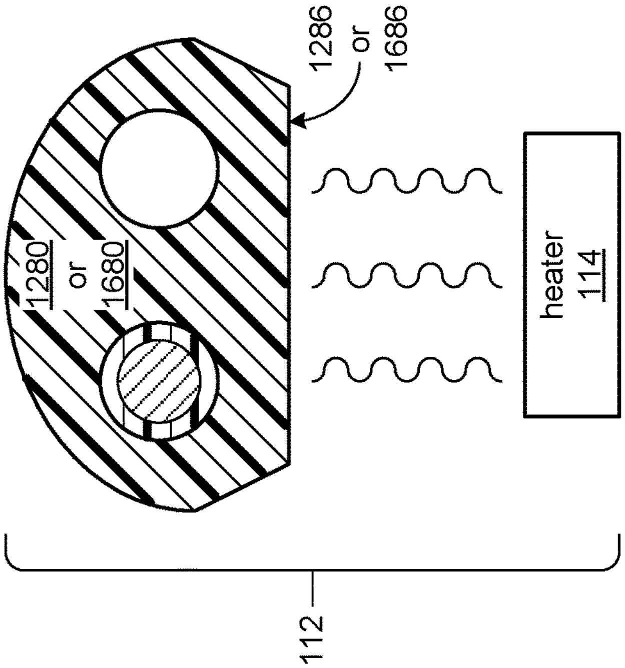
FIG. 5I is a block diagram of another alternate heating device that may be incorporated into the embodiment of adaptation of the hose making apparatus of FIGS. 5A-B or of FIG. 5C.
Figure 5H:
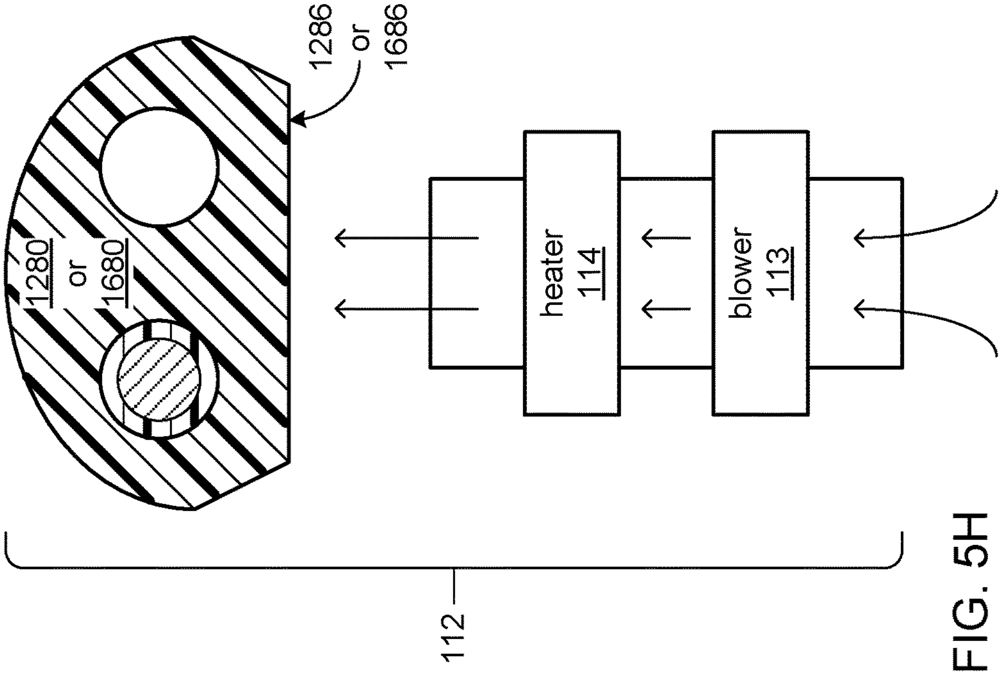
FIG. 5H is a block diagram of an alternate heating device that may be incorporated into the embodiment of adaptation of the hose making apparatus of FIGS. 5A-B or of FIG. 5C.

FIG. 5H provides a block diagram of an alternate embodiment of the heating device 112 (along with a cross-section of an example support helix 1280 or 1680, similar to what is depicted in FIGS. 5F-G) that enables such selective heating of the bonding surface 1286 or 1686 of a support helix 1280 or 1680. As depicted, such an alternate embodiment of the heating device 112 may be similar to the embodiment of FIGS. 5E-G, but with the substantial difference of not including the heating tube 115. Thus, unlike the embodiment of the heating device 112 of FIGS. 5E-G, in the alternate embodiment of FIG. 5H, there may be no component thereof that serves to in any way direct the flow of hot air that is produced by the combination of the blower 113 and the heater 114 fully around the cross-section of a support helix 1280 or 1680. Thus, also unlike the embodiment of the heating device 112 of FIGS. 5E-G, in the alternate embodiment of FIG. 5H, the support helix 1280 or 1680 must be routed past this alternate embodiment of the heating device 112 in a position and orientation relative thereto that causes the bonding surface 1286 and 1686 to face into the output hot air flow so as to enable such selective re-heating of the bonding surface 1286 or 1686.

The temperature and/or volume of the hot air output by the alternate embodiment of the heating device 112 of FIG. 5H may be adjusted to control the degree to which the bonding surface 1286 or 1686 is caused to become molten. Such parameters as the temperature and/or volume of the hot air may be based on such factors as the shape and/or size of the cross-section of the bead of support helix 1280 or 1680, the shape and/or size of the bonding surface 1286 or 1686, the quantity and/or size of any wires 1290 or 1690 within the support helix 1280 or 1680, the quantity and/or size of any lumens 1289 or 1689 within the support helix 1280 or 1680 (for example, a support helix 1280 or 1680 that incorporates large and/or multiple lumen(s) 1289 or 1689 may have significantly less mass than a support helix 1280 or 1680 that does not), and/or the speed at which the bead is fed past the heating device 112. The speed at which the bead of the support helix 1280 or 1680 is fed past the heating device 112 of FIG. 5H may be entirely controlled by the speed at which bead is to be fed to the hose manufacturing apparatus 100 to form a hose 1200 or 1600, respectively.

FIG. 5I provides a block diagram of another alternate embodiment of the heating device 112 (also along with a cross-section of an example support helix 1280 or 1680, similar to FIGS. 5F-H) that enables such selective heating of the bonding surface 1286 or 1686 of a support helix 1280 or 1680. As depicted, this other alternate embodiment of the heating device 112 may be similar to the embodiment of FIG. 5H, but with the substantial difference of not including the blower 113 to create an air flow, and instead, relying upon solely the heater 114 to output radiant heat toward the bonding surface 1286 or 1686 of a support helix 1280 or 1680. Thus, like the alternate embodiment of the heating device 112 of FIG. 5H, in this other alternate embodiment of FIG. 5I, the support helix 1280 or 1680 must also be routed past this other alternate embodiment of the heating device 112 in at least a particular orientation to enable the bonding surface 1286 or 1686 to be re-heated.

The temperature and/or level of energy of the radiant heat output by the other alternate embodiment of the heating device 112 of FIG. 5I may be adjusted to control the degree to which the bonding surface 1286 or 1686 is caused to become molten. Such parameters as the temperature and/or level of energy of the radiant heat output may be based on such factors as the shape and/or size of the cross-section of the bead of support helix 1280 or 1680, the shape and/or size of the bonding surface 1286 or 1686, the quantity and/or size of any wires within the support helix 1280 or 1680, the quantity and/or size of any lumens 1289 or 1689 within the support helix 1280 or 1680, the speed at which the bead is fed past the heating device 112, and/or the distance from the heating device 112 at which the bead is fed past the heating device 112. The speed at which the bead of the support helix 1280 or 1680 is fed past the heating device 112 of FIG. 5I may be entirely controlled by the speed at which bead is to be fed to the hose manufacturing apparatus 100 to form a hose 1200 or 1600, respectively.

Referring to both of the alternate embodiments of the heating device 112 of FIGS. 5H and 5I, as the bead of support helix 1280 or 1680 is fed past either of these alternate embodiments of the heating device 112, the bonding surface 1286 or 1686 is re-heated to a controlled degree that causes the plastics material thereof to become slightly molten such that the bonding surface 1286 or 1686, respectively, is softened and becomes tacky. Again, the degree of re-heating may be controlled to avoid overheating to such an extent that inner portions of the plastics material of the bead of support helix 1280 or 1680 in the vicinity of the electrical wires 1290 or 1690 becomes molten such that they are able to migrate to new positions within that plastics material, and/or to avoid overheating to such an extent that inner portions of the plastics material of the bead of support helix in the vicinity of any lumens 1289 or 1689 becomes molten such that the shape and/or size thereof are caused to change. The degree of re-heating may be controlled to avoid overheating to such an extent that inner portions of the plastics material of the bead of support helix 1280 or 1680 in the vicinity of any electrical wires 1290 or 1690 becomes molten such that they are able to migrate to new positions within that plastics material, and/or to avoid overheating to such an extent that inner portions of the plastics material of the bead of support helix in the vicinity of any lumens 1289 or 1689 becomes molten such that the shape and/or size thereof are caused to change. By making the plastics material of the bonding surface 1286 or 1686 tacky, the now re-heated bonding surface 1286 or 1686 is caused to readily bond to the exterior of the wall 1270 or 1670 of the hose 1200 or 1600 that is being formed from the web of plastics material freshly extruded by the extruder **107*a* (e.g., the bonding surfaces 1276 and 1286, or 1676 and 1686**, are caused to readily bond).

Figure 5J:
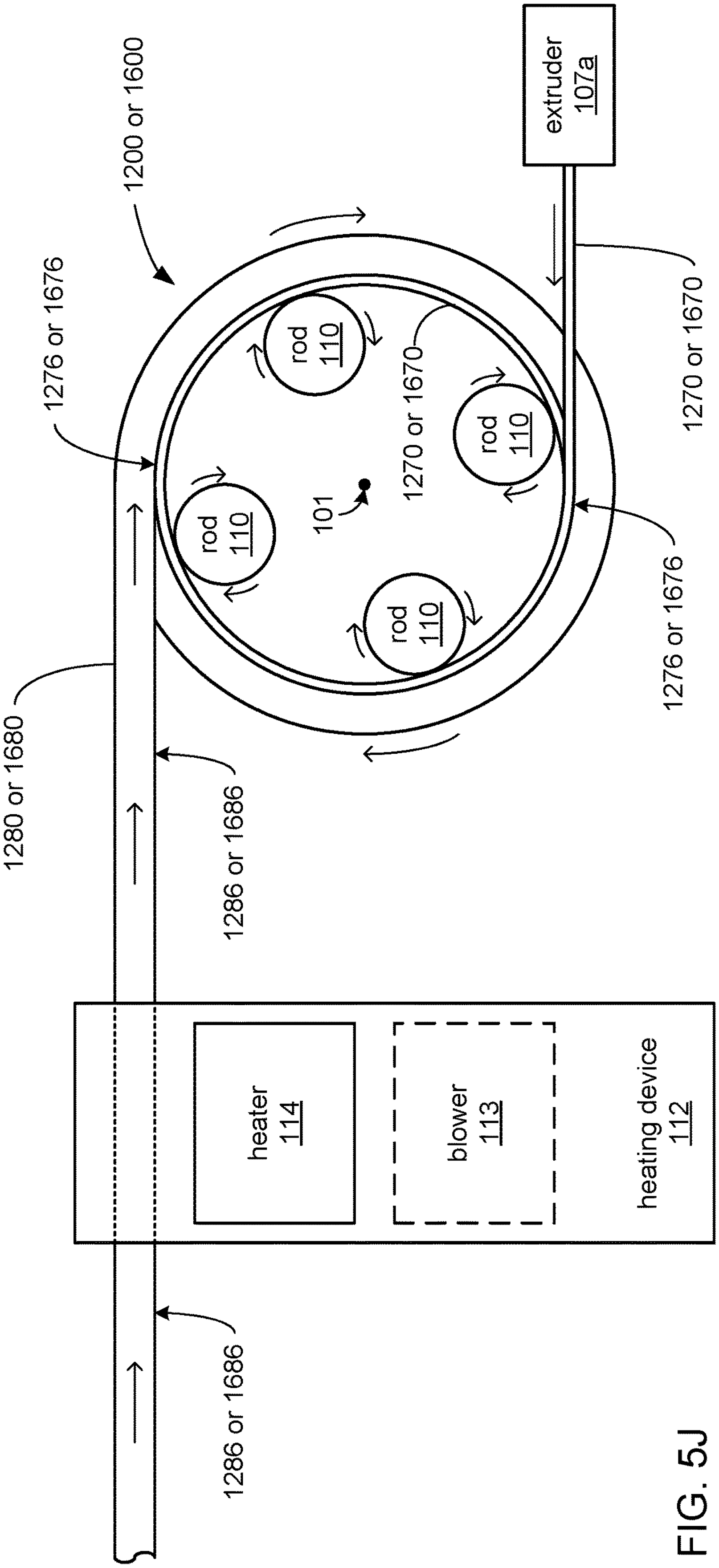
FIG. 5J provides another block diagram of components of a hose making apparatus that has been adapted in accordance with still another alternate embodiment of adaptation to make the hose of FIG. 4A (or the variant thereof of FIG. 4C) to incorporate the alternate heating device of either FIG. 5H or FIG. 5I.

Turning to FIG. 5J, an advantage that may be afforded by limiting (to the extent possible) the re-heating of the exterior of a support helix 1280 or 1680 to the bonding surface 1286 or 1686 may be that the plastics material that forms the bonding surface 1286 or 1686 (and extending into the plastics material of the support helix 1280 or 1680 to a relatively limited depth from the bonding surface 1286 or 1686 that is not deep enough to extend to any wires or lumens positioned therein) may become molten to an extent that enables the plastics material within the side of the support helix 1280 or 1680 that includes the bonding surface 1286 or 1686 to be more easily compressed as part of becoming more easily bendable so as to be more pliable for following the curvature of the exterior of the wall 1270 or 1670 of a hose 1200 and 1600 as the bonding surface 1286 or 1686 is put into contact with the exterior of the wall 1270 or 1670, respectively. By allowing at least the portion of the exterior of the support helix 1280 or 1680 that is on the side thereof that is opposite of the bonding surface 1286 or 1686 to remain in an un-molten state, at least that portion on that side may serve to resist allowing the support helix 1280 or 1680 to become distorted in its dimensions in other ways, such as being flattened against the wall 1270 or 1670 such that the ability of the support helix 1280 or 1680 to serve its function as a physical support of the hose 1270 or 1670 is compromised.

Alternatively or additionally, an advantage that may be afforded by limiting (to the extent possible) the re-heating of the exterior of a support helix 1280 or 1680 to the bonding surface 1286 or 1686 may be that the portion of the exterior of the support helix 1280 or 1680 that is caused to become tacky as a result of becoming molten may be largely or entirely limited to the bonding surface 1286 or 1686. In this way other portions of the exterior of the support helix 1280 or 1680 are allowed to remain in an un-molten state such that they do not become tacky, which may make handling the support helix 1280 or 1680 (especially where it is being unwound from a spool 119 as depicted in FIG. 5B) considerably easier.

Figure 6A:
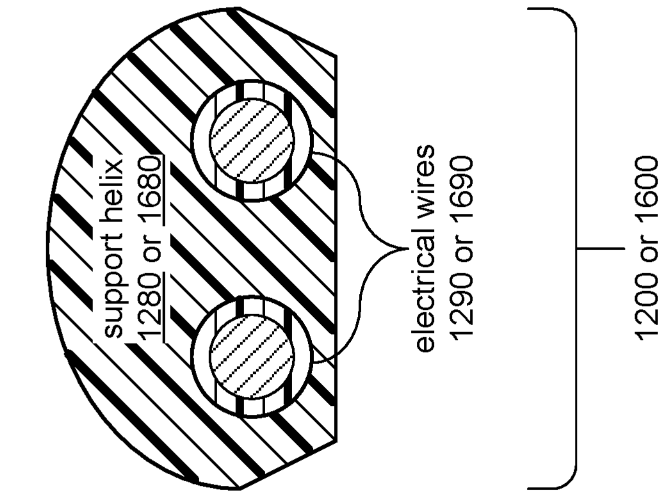
FIGS. 6A, 6B, 6C and 6D, together, provide cross-sectional views of a variety of embodiments of support helix (including of the support helix of FIGS. 4A-C and 4F-G) having a "bread slice" cross-section.
Figure 6B:
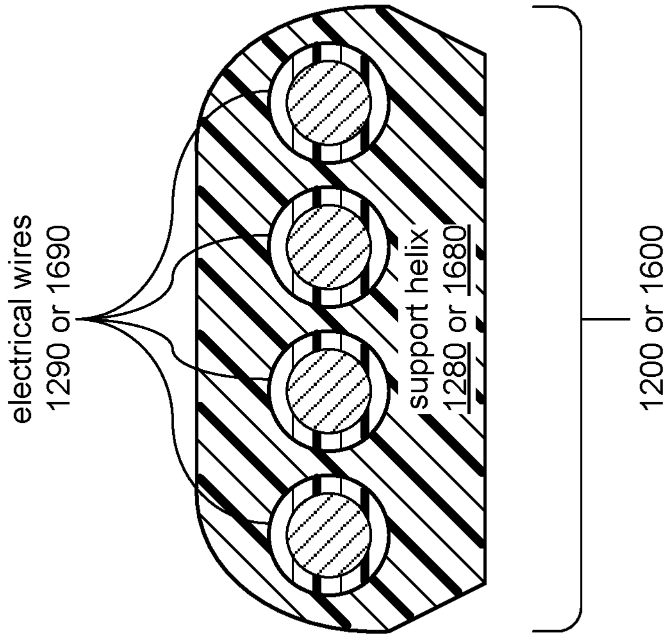
Figure 6C:
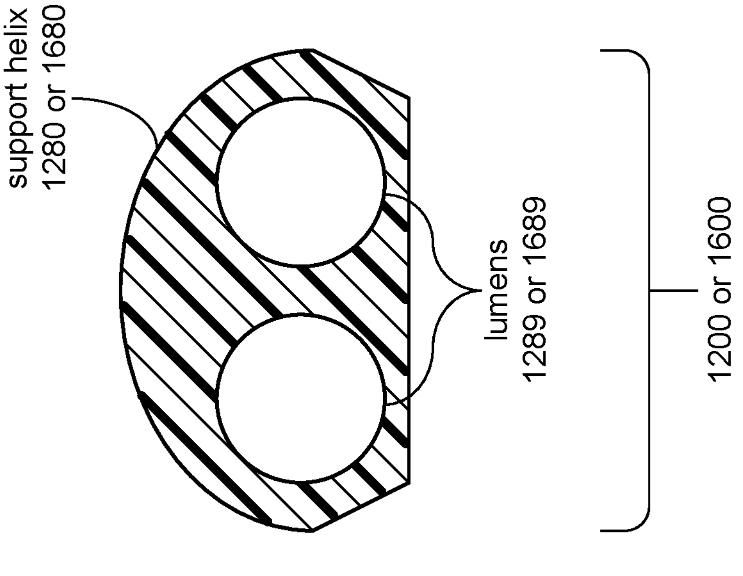
Figure 6D:
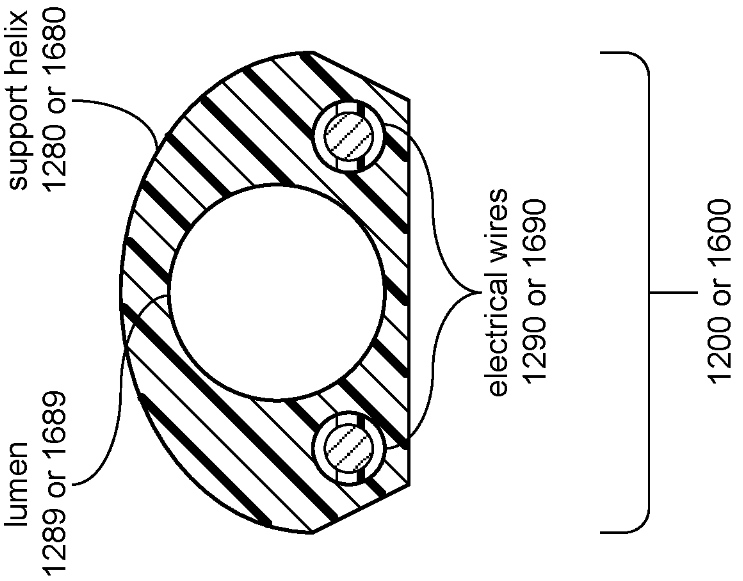
Figure 6F:
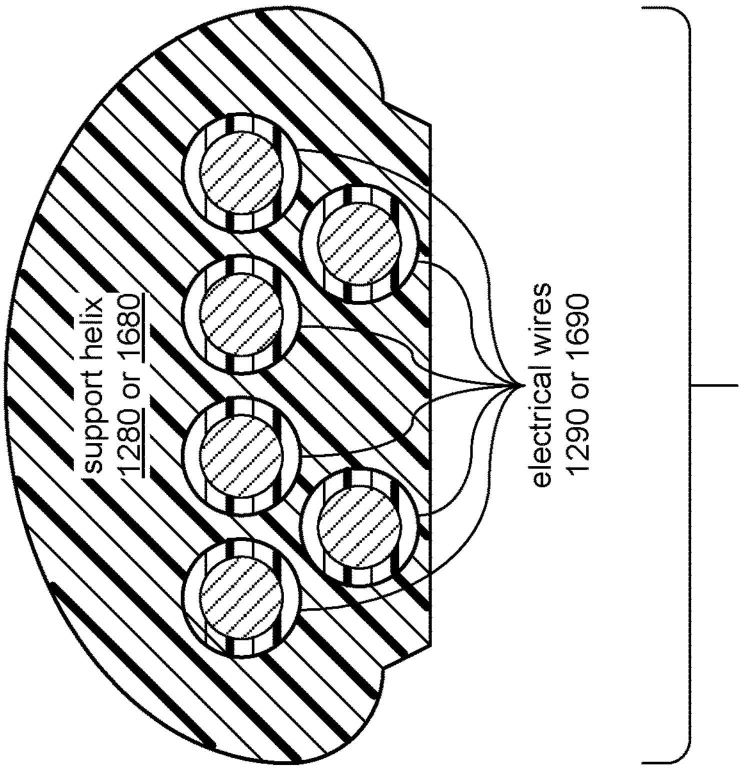
FIGS. 6E, 6F, 6G, 6H, 6I and 6J, together, provide cross-sectional views of a variety of embodiments of support helix having a "mushroom" cross-section.
Figure 6E:
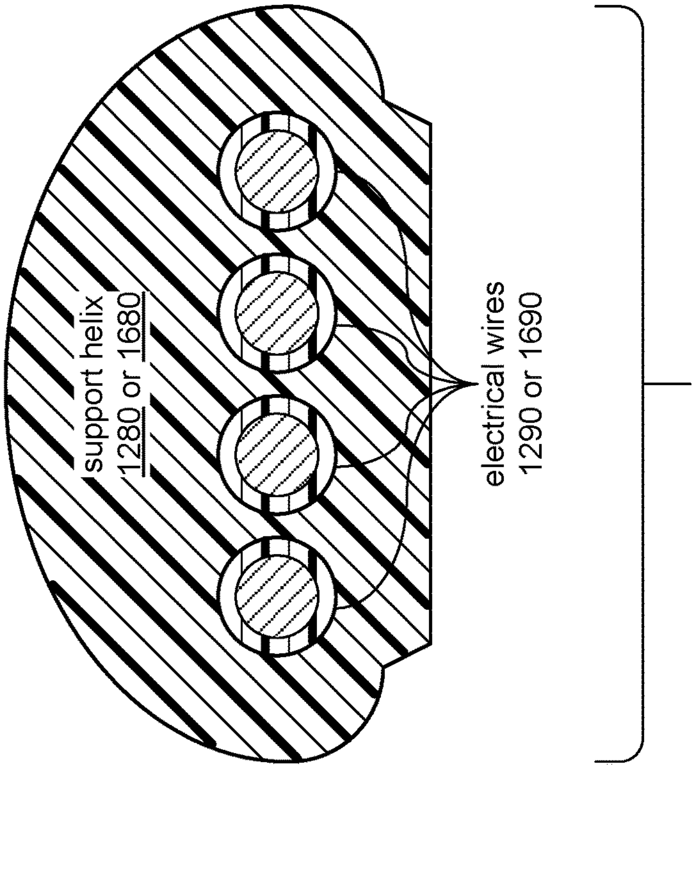
Figure 6H:
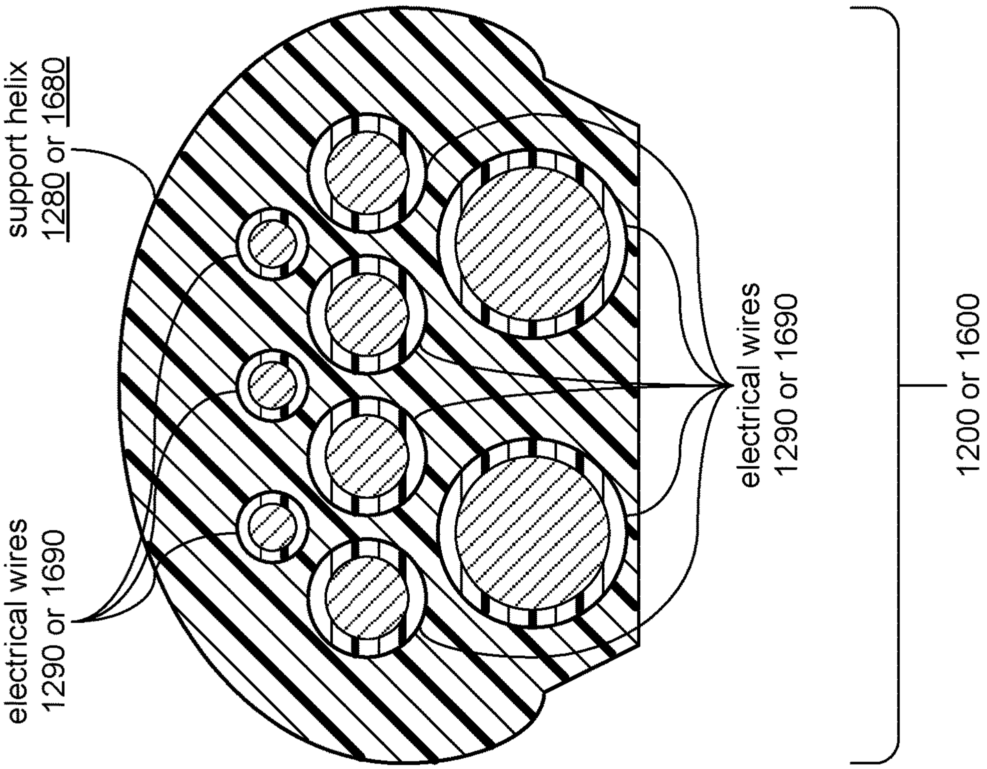
Figure 6G:
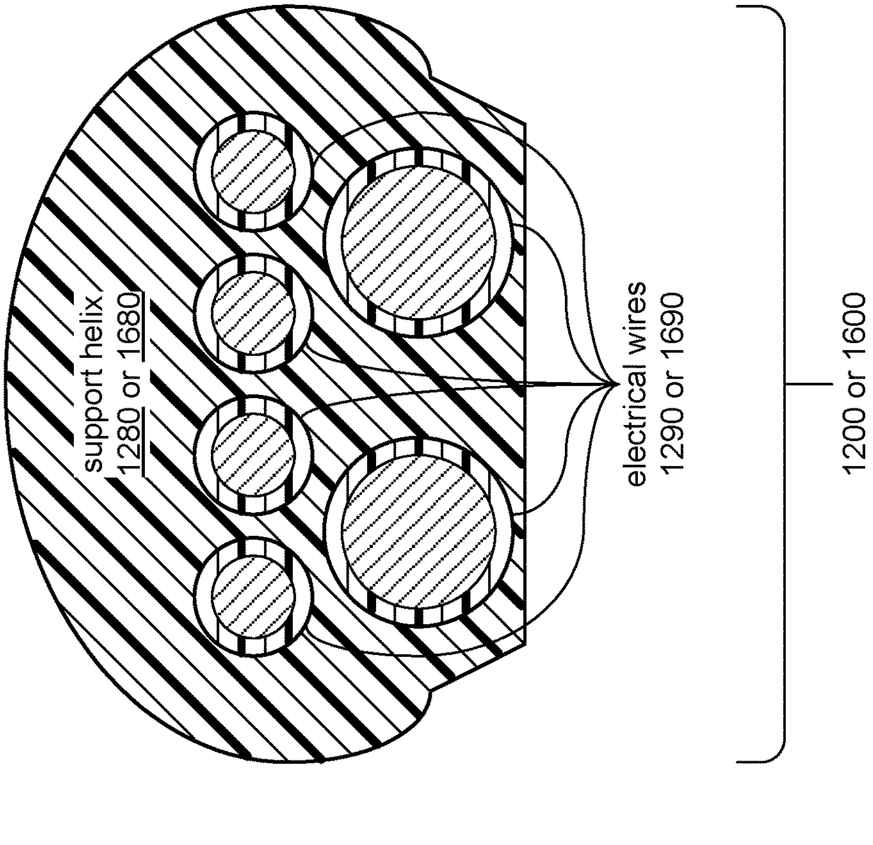
Figure 6I:
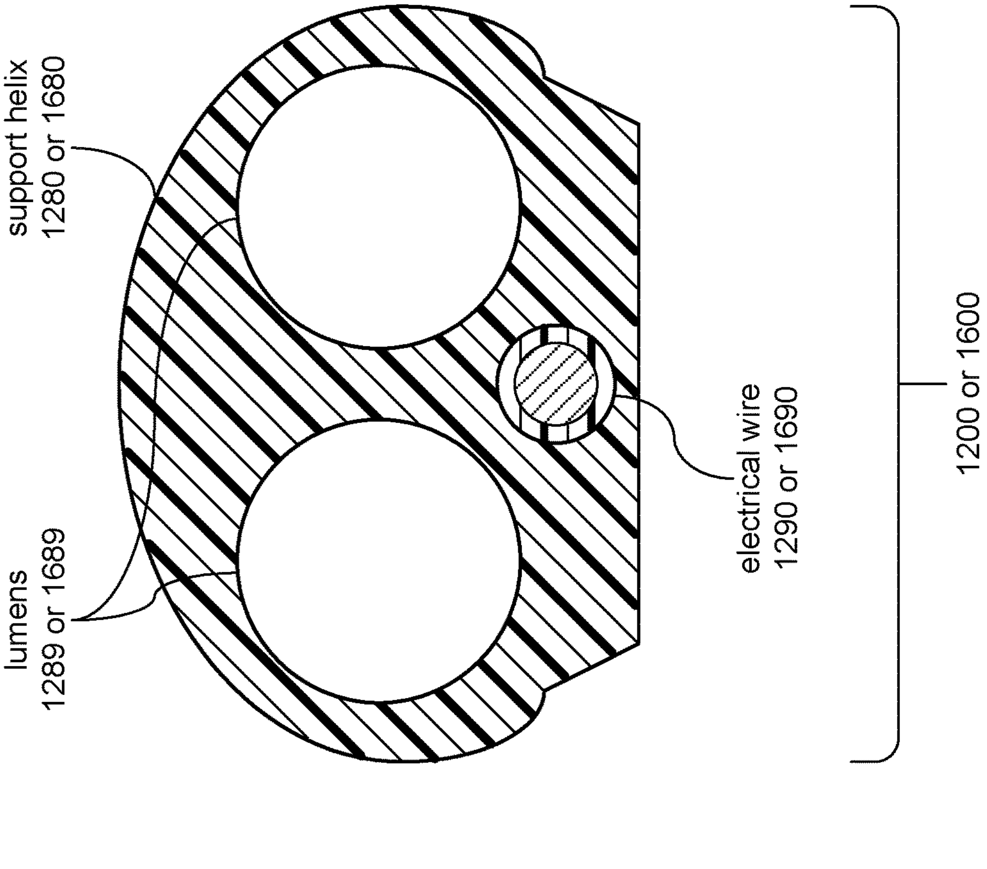
Figure 6J:
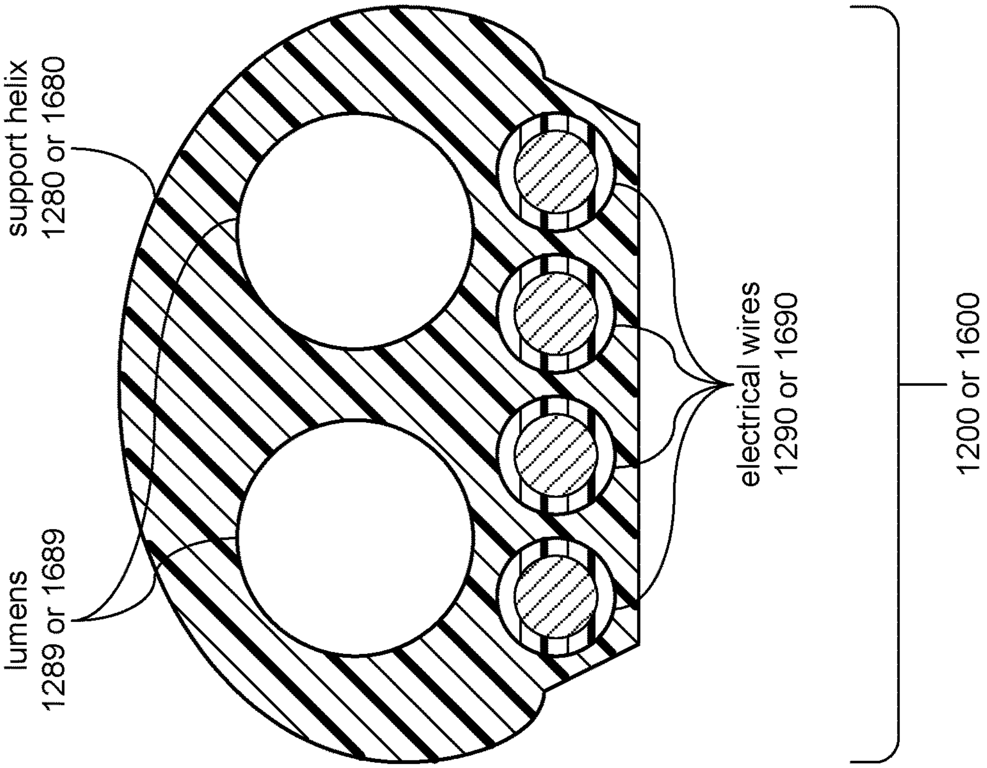
Figure 6K:
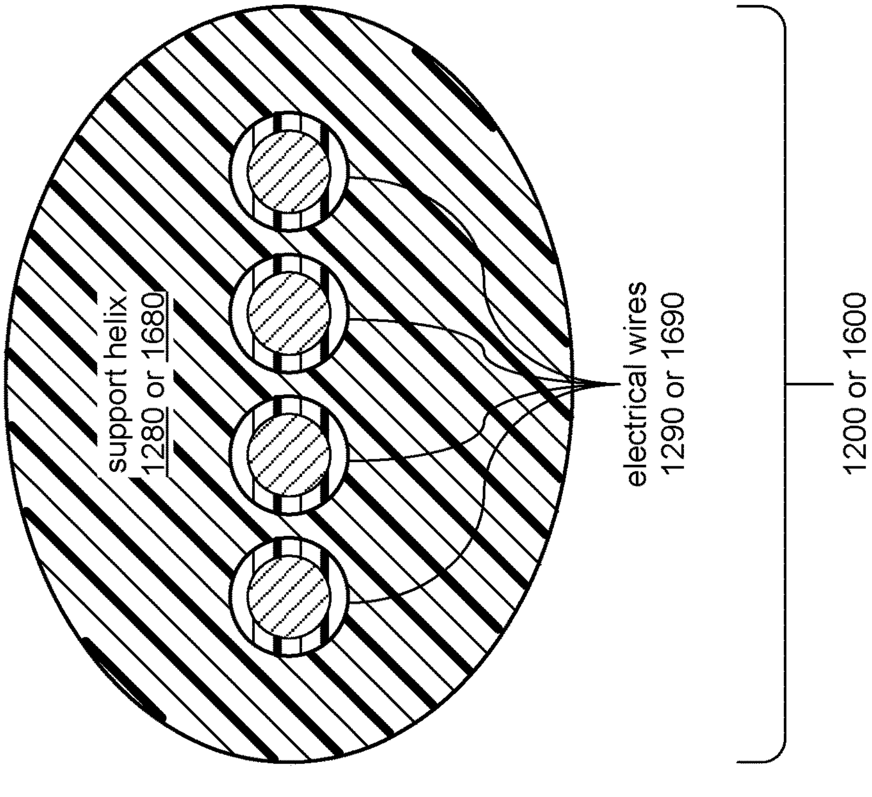
FIGS. 6K, 6L, 6M and 6N, together, provide cross-sectional views of a variety of embodiments of support helix having a generally elliptical cross-section.
Figure 6L:
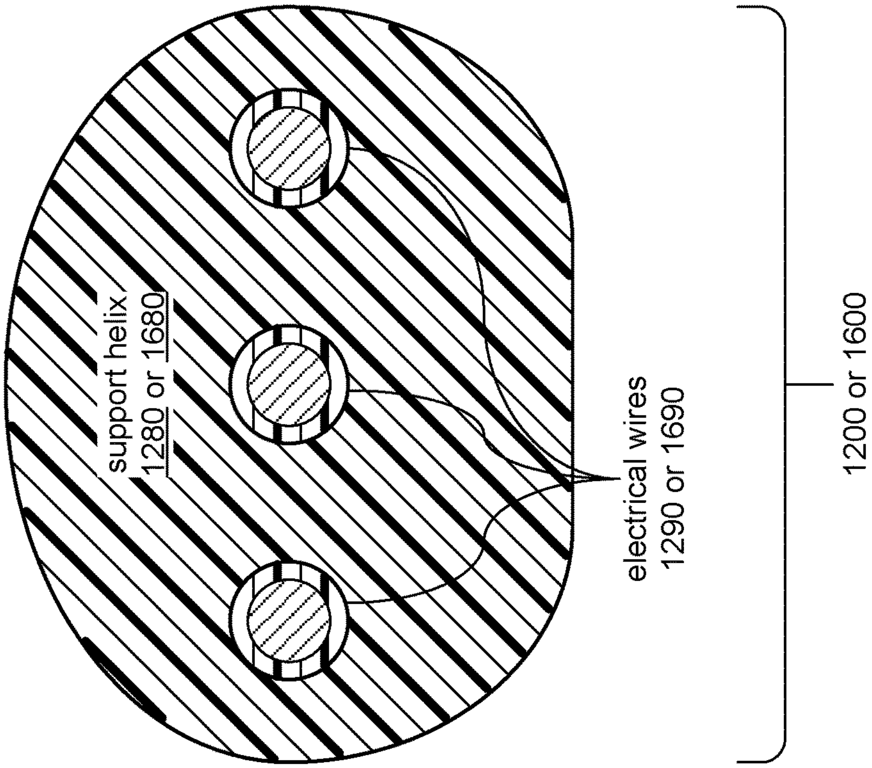
Figure 6N:
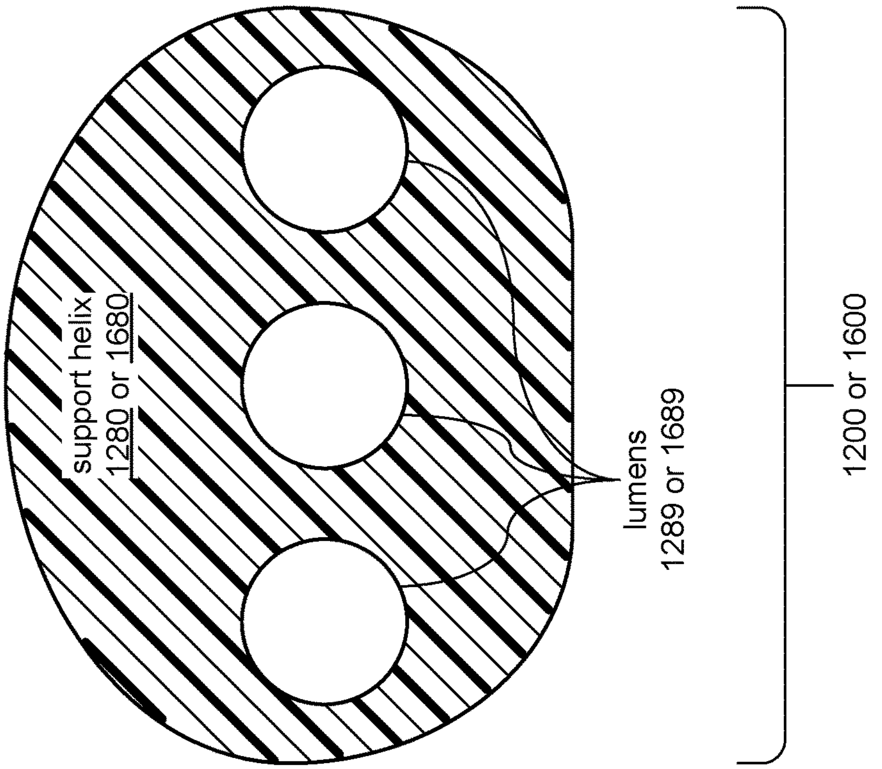
Figure 6M:
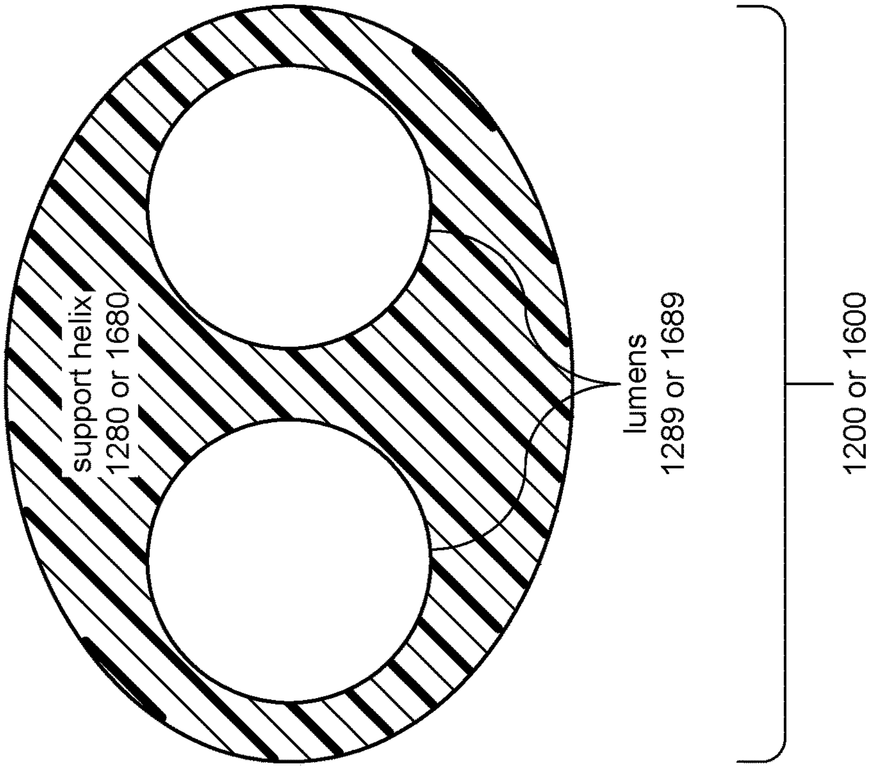
Figure 6O:
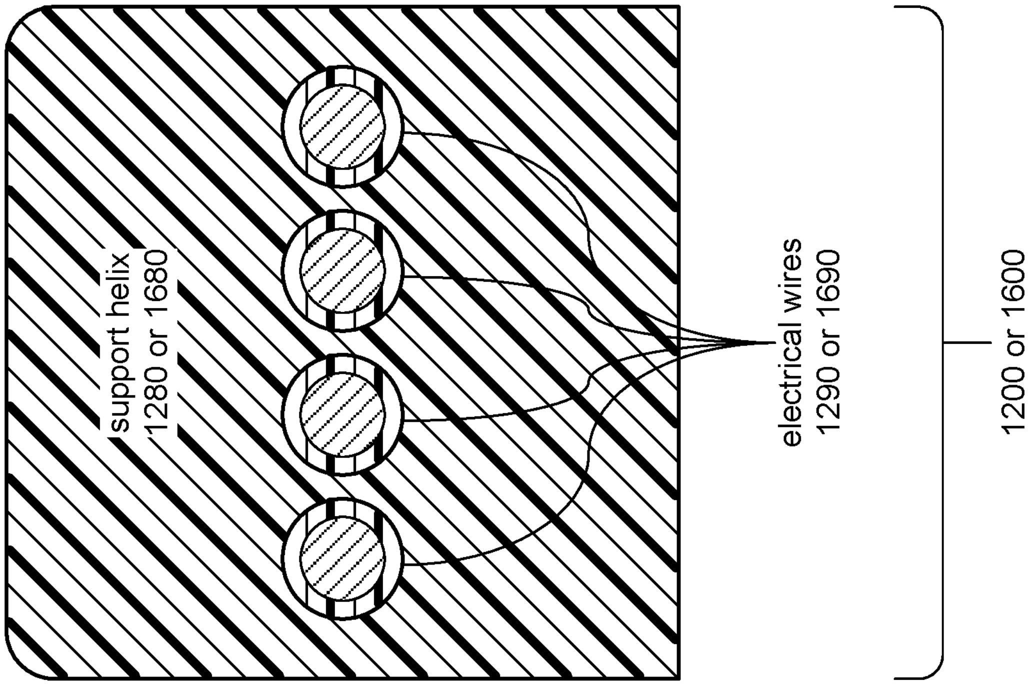
Figure 6P:
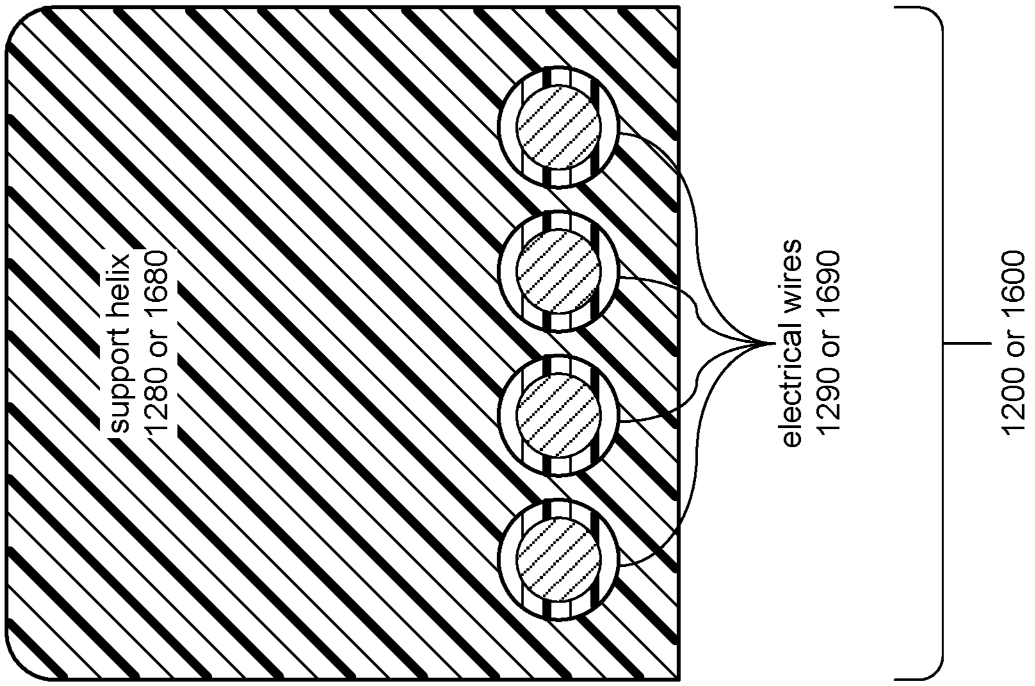
Figure 6R:
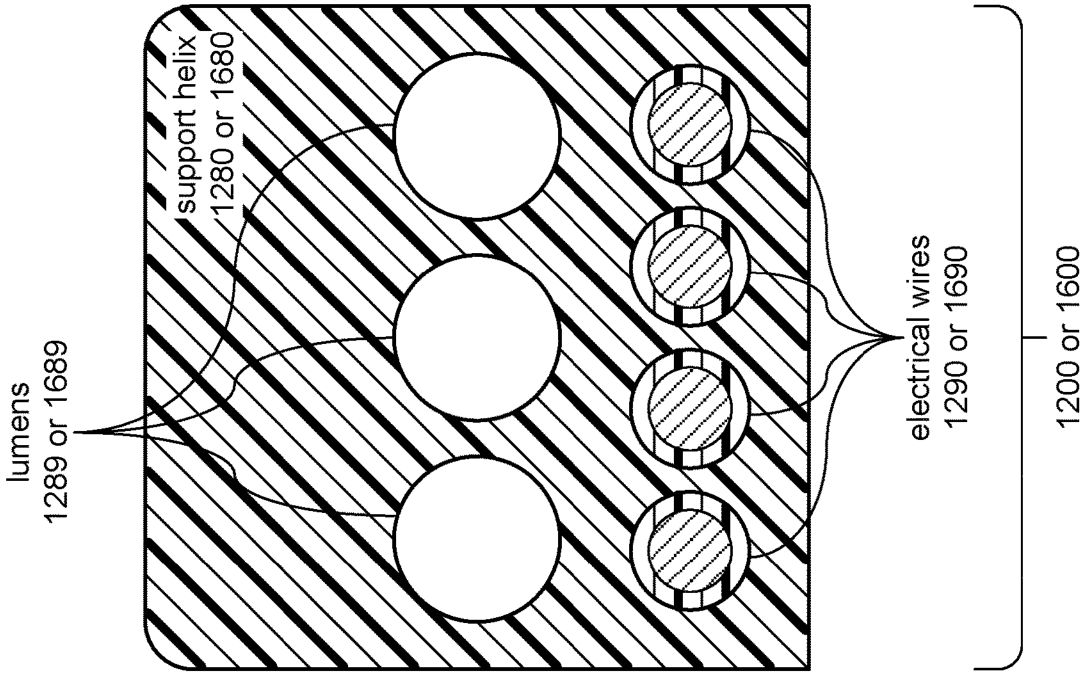
Figure 6Q:
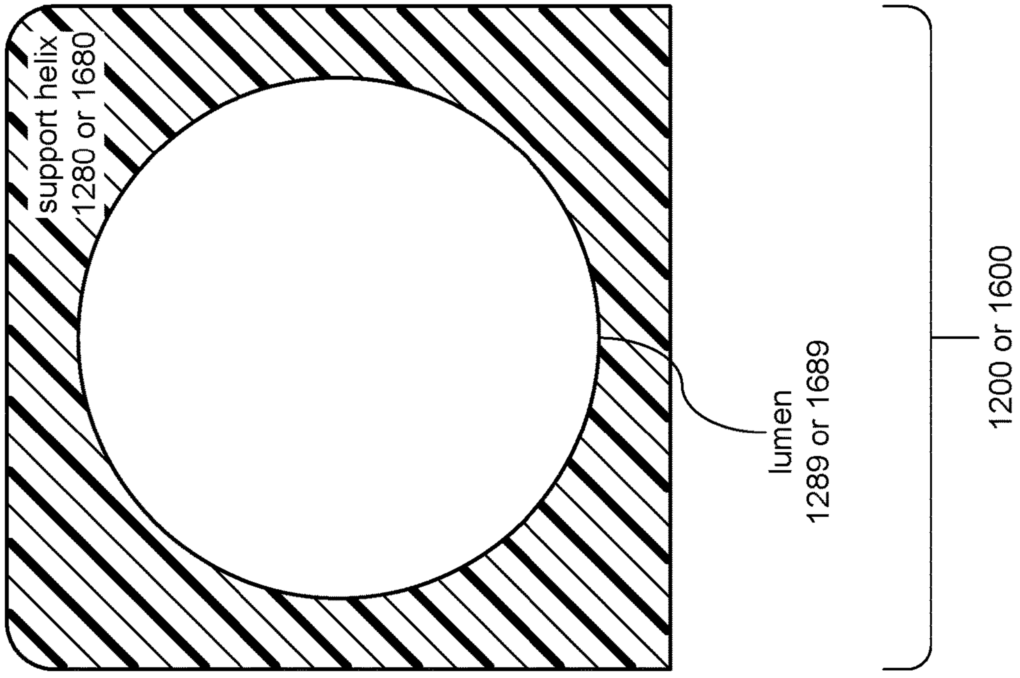
Figure 6T:
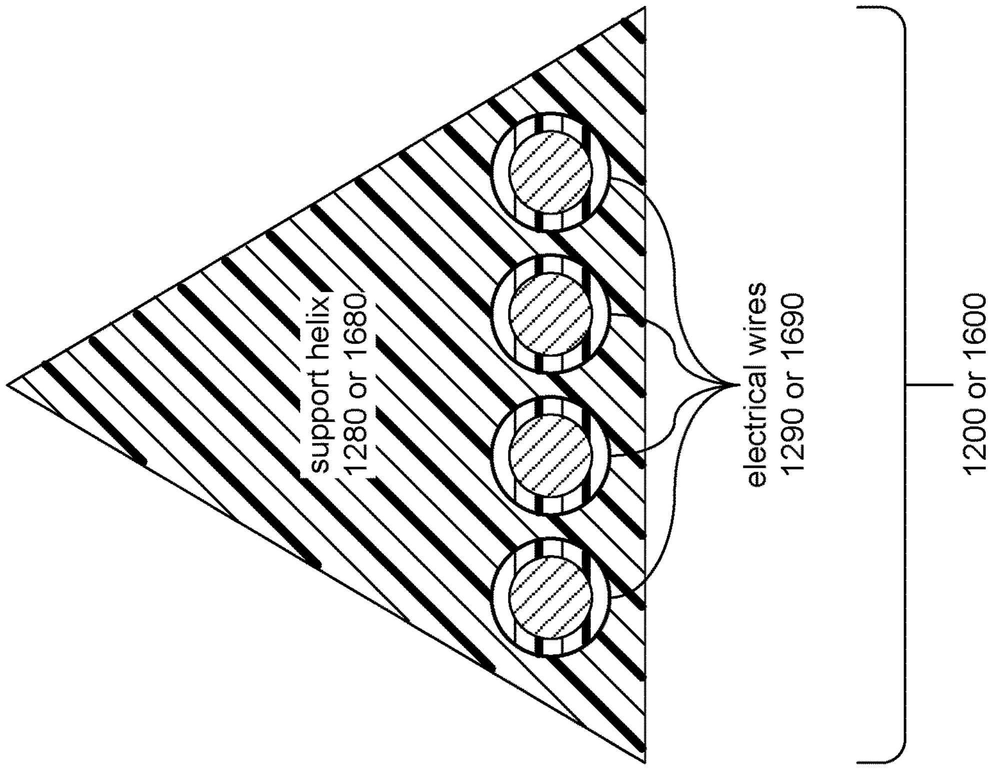
FIG. 6T provides a cross-sectional view of an embodiment of support helix having a generally triangular cross-section.
Figure 6S:
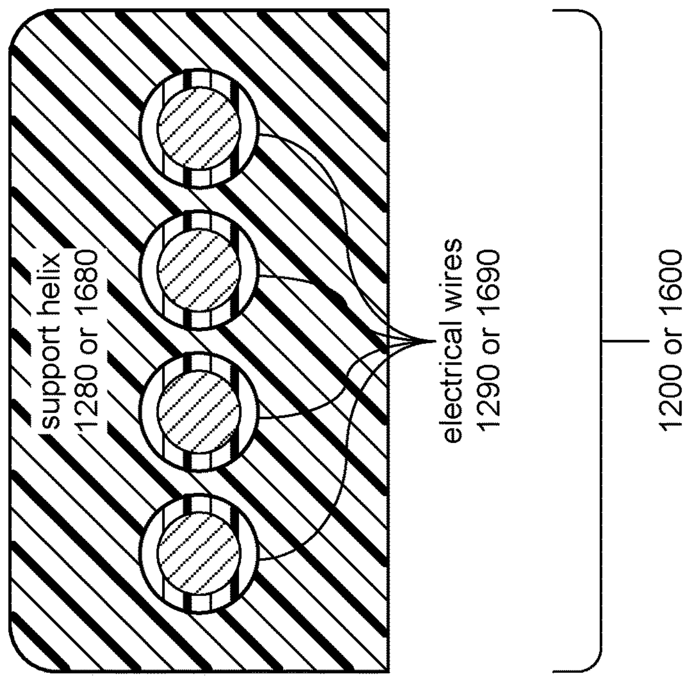

FIGS. 6A through 6T depict cross-sections of an example assortment of types of support helix 1280 or 1680 that may be dynamically selected for use in making a hose 1200 or 1600, respectively. As so depicted, these widely differing types of support helix 1280 or 1680 may differ in shape and/or size of the cross-section of their plastics material, as well as in the quantity, size, and/or arrangement of electrical wires 1290 or 1690 therein, and/or of lumens 1289 or 1689 therein.

FIGS. 6A, 6B, 6C and 6D depict the cross-sections of four example embodiments of support helix 1280 or 1680 that have a similar cross-section of plastics material that may be said to resemble a slice of a loaf of bread. As depicted in FIGS. 6A-B, the quantities of electrical wires 1290 or 1690 incorporated therein may differ. As depicted in FIGS. 6C-D, the quantities and/or sizes of the lumens 1289 or 1689 incorporated therein may differ, as well as either being accompanied by electrical wire(s) 1290 or 1690, or not.

FIGS. 6E, 6F, 6G, 6H, 6I and 6J depict the cross-sections of six example embodiments of support helix 1280 or 1680 that have a similar "mushroom" cross-section of plastics material. As depicted in FIGS. 6E-F, differing quantities of electrical wires 1290 or 1690 may be incorporated into the same shape and/or size of cross-section of the plastics material in different ones of these example embodiments, and in differing arrangements therein. As depicted in FIGS. 6G-H, electrical wires 1290 or 1690 of differing size (e.g., differing gauges) may be incorporated into the same shape and/or size of cross-section of the plastics material in different ones of these example embodiments. As depicted in FIGS. 6I-J, lumens 1289 or 1689 of differing size may be incorporated into the same shape and/or size of cross-section of the plastics material in different ones of these example embodiments, as well as either being accompanied by electrical wire(s) 1290 or 1690, or not.

FIGS. 6K, 6L, 6M and 6N depict the cross-sections of four example embodiments of support helix 1280 or 1680 that have generally similar elliptical cross-sections of plastics material. As depicted, such cross-sections of plastics material may differ slightly in such details as the elliptical cross-sections depicted in FIGS. 6L and 6N having a flattened portion of its outer surface (which may enhance bonding to the outer surface of the wall 1270 or 1670), whereas the cross-sections depicted in FIGS. 6K and 6M do not. As depicted in FIGS. 6K-L, the quantities of electrical wires 1290 or 1690 incorporated therein may differ. As depicted in FIGS. 6M-N, the quantities and/or sizes of lumens 1289 or 1689 incorporated into such support helixes 1280 or 1680 may also differ.

FIGS. 60, 6P, 6Q, 6R and 6S depict the cross-sections of five example embodiments of support helix 1280 or 1680 that have generally similar rectangular cross-sections of plastics material. As depicted, such cross-sections of plastics material may differ slightly in their dimensions and/or in their ratios between height and width. As depicted in FIGS. 60-P and 6R-S, even though different ones of such embodiments may all incorporate the same quantity and/or size of electrical wires 1290 or 1690, they may differ in the placement of those electrical wires 1290 or 1690 within their cross-sections, and they may differ in whether such electrical wires 1290 or 1690 are accompanied by one or more lumens 1289 or 1689. Alternatively, and as depicted in FIG. 6Q, such cross-sections of plastics material may incorporate just one or more lumens 1289 or 1689, including the depicted single relatively large lumen 1289 or 1689 that may occupy the majority of the such a cross-section.

FIG. 6T depicts a cross-section of an example embodiment of support helix 1280 or 1680 that has a generally triangular cross-section of plastics material. As depicted, such a cross-section of plastics material may incorporate one or more wires 1290 or 1690. However, other embodiments are possible of such a cross-section of plastics material that include one or more lumens 1289 or 1689, either in addition to, or in lieu of, incorporating one or more wires 1290 or 1690.

FIGS. 7A through 7E, taken together, depict various aspects of coupling the expiratory inlet fitting 1500 to an undermold coupling 1800, and thereby, to one end of the expiratory hose 1600. Stated differently, and as earlier depicted in the exploded perspective views in each of FIGS. 1D, 1E and 3A, the expiratory inlet fitting 1500 may be coupled to one end of the expiratory hose 1600 via the depicted undermold coupling 1800 interposed between a portion of the outer surface of that end of the expiratory hose 1600 and a portion of the inner surface of a hose interface 1580 of the expiratory inlet fitting 1500.

The undermold coupling 1800 may include a tubular portion 1881 having a cylindrical tubular shape that defines a passage therethrough. At one end of the tubular shape of the tubular portion 1881 may be a ring 1883 that extends radially outward from the cylindrical tubular shape of the tubular portion 1881. Extending from the ring 1883 (or form another portion of the external surface of the tubular portion 1881) may be one or more gratings 1885 that may be defined by one or more parallel elongate portions of the flexible plastics material of the undermold coupling 1800 that define one or more parallel slots 1886. Each of the elongate portions of the material that define one of the one or more gratings 1885 may be curved to allow each to extend in a manner that follows the curve of the cylindrical shape of the tubular portion 1881.

Each grating 1885 may be supported by, and attached to, the rest of the structure of the undermold coupling 1800 (e.g., connected to the ring portion 1883, as depicted) by a pair of grating supports 1884 that may cooperate with the grating 1885 to create what may visually resemble a ladder. The grating supports may tend to support the one or more gratings 1885 at a location and in an orientation that causes each grating 1885 to extend alongside and in parallel with a portion of the external surface of the tubular portion 1881. While each grating 1885 is so positioned by one or more of the grating supports 1884, inwardly facing surfaces 1888 of each of the one or more curved elongate portions of flexible plastics material that defines each of the gratings 1885 may tend to be positioned in contact with the portion of the external surface of the tubular portion 1881 that its corresponding grating 1885 overlies. Being formed of the flexible plastics material of the undermold coupling 1800, the grating supports 1884 may each be flexible enough to allow each of the gratings 1885 to be pulled away from its position extending alongside and parallel with a portion of the external surface of the tubular portion 1881 (thereby pulling the inwardly facing surfaces thereof out of contact with the external surface of the tubular portion 1881.

The hose interface of the expiratory inlet fitting 1500 may incorporate one or more gratings 1586 that are meant to correspond to the one or more gratings 1885 carried by the undermold coupling 1800. Each of the one or more gratings 1586 may be defined by one or more parallel elongate portions of the rigid plastics material of the expiratory inlet fitting 1500 that define one or more parallel slots 1585 that may have the appearance of a set of one or more vent slots formed through the wall of the expiratory inlet fitting 1500. Each of the elongate portions of the material that define one of the one or more gratings 1586 may be curved to allow each to extend in a manner that parallels the curve of the cylindrical shape of the tubular portion 1881. Additionally, the one or more parallel elongate portions of the material of the expiratory fitting 1500 that define one of the one or more gratings 1586, and the one or more slots 1585 defined thereby, may be intersected by one or more troughs 1584 formed in the cylindrical external surface of the expiratory inlet fitting 1500 to receive a corresponding one or more of the grating supports 1884.

As depicted most clearly in FIGS. 7A, 7B, 7D and 7E, the undermold coupling 1800 may include threads 1882 formed on the inner surface of the tubular portion 1881 to receive and surround the external surface of one end of the expiratory hose 1600 in a manner that engages the wall 1670 and the support helix 1680 thereof as if the wall 1670 and helix 1680, together, formed matching threads as a mechanism by which the undermold coupling 1800 may grip that end of expiratory hose 1600 within the tubular portion 1881. In some embodiments, the tubular portion 1881 of the undermold coupling 1800 may be threaded onto an end of the expiratory hose 1600.

Figure 7A:
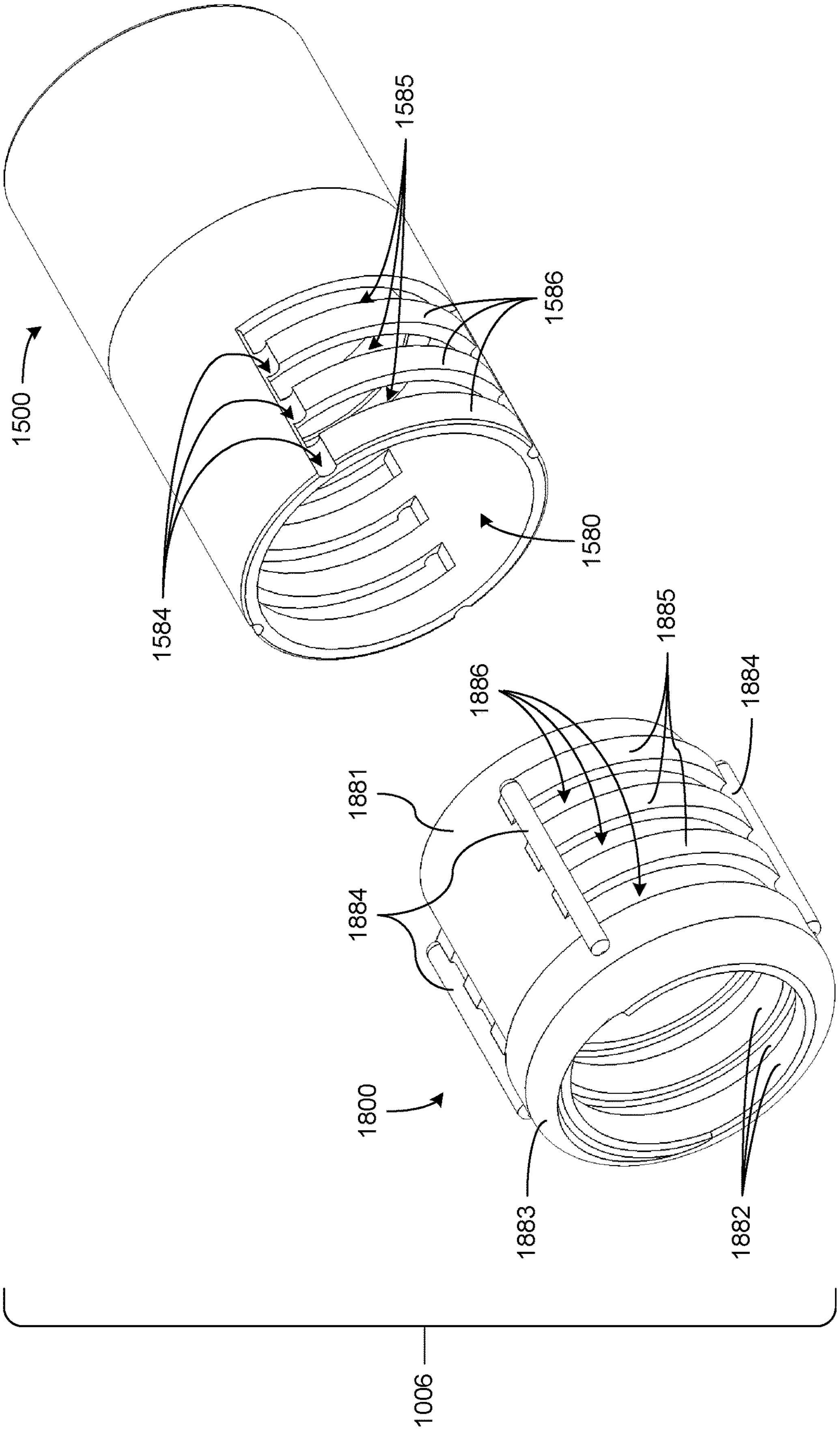
FIG. 7A is a perspective view a hose fitting and corresponding undermold coupling of any of the embodiments of heated respiratory hose assembly of any of FIG. 1A, 3A, 3B or 3C showing details of the features of one of the hose fittings and corresponding undermold coupling that are used to couple each to the other, and that are used to couple the undermold coupling to an end of one of the hoses.
Figure 7B:
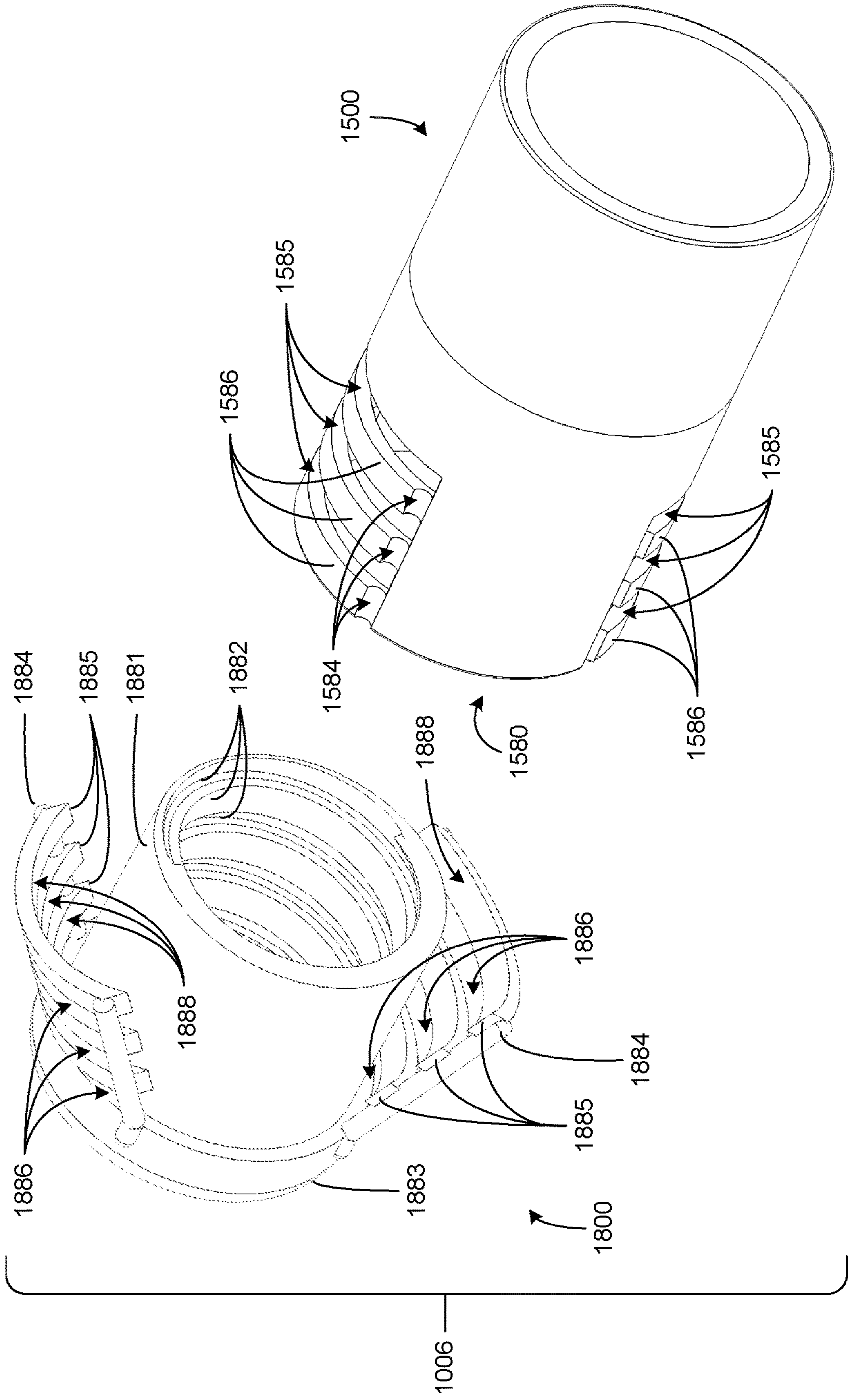
FIG. 7B is another perspective view of the hose fitting and corresponding undermold coupling of FIG. 7A showing details of the manner in which features of each are used to coupled each to the other.
Figure 7C:
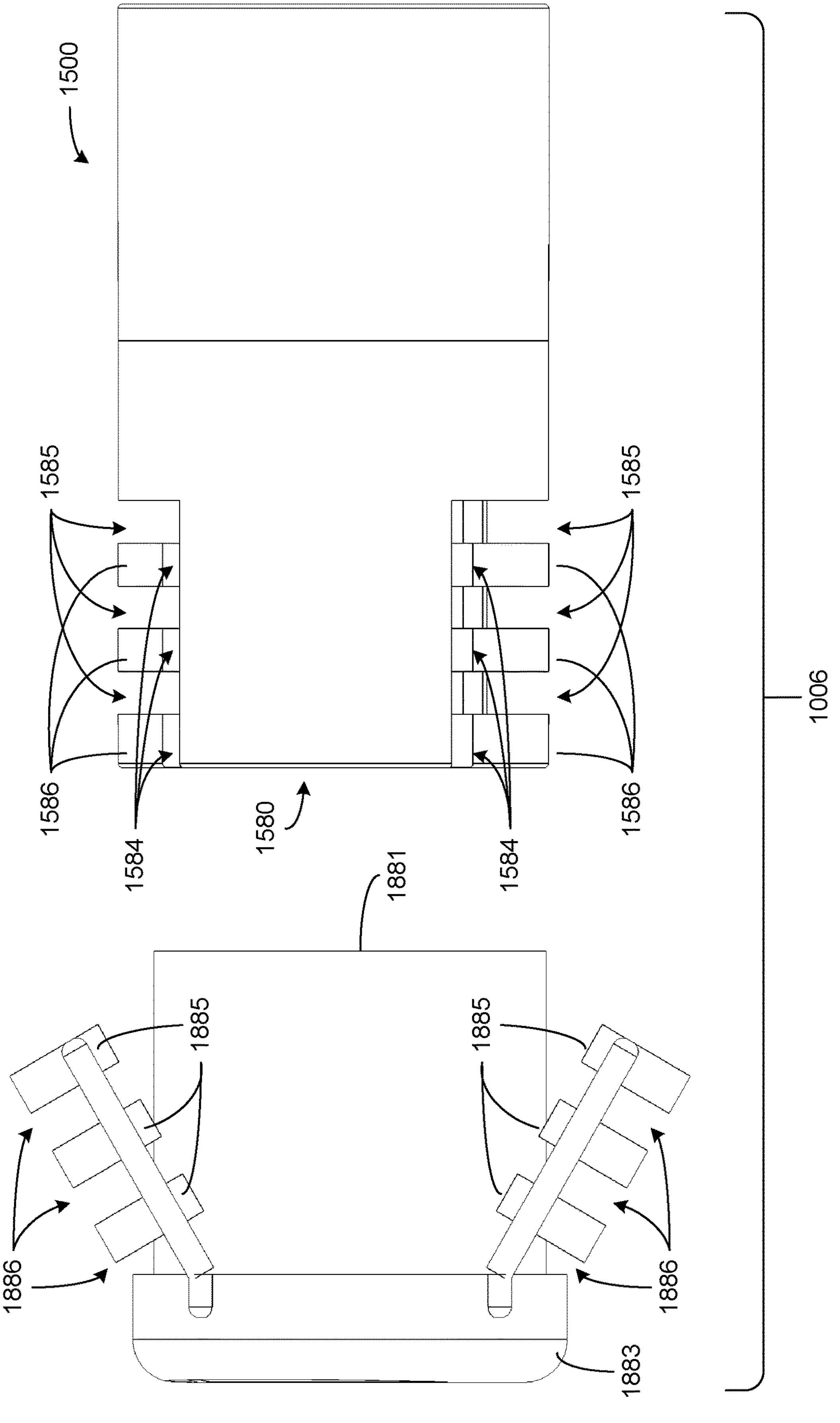
FIG. 7C is an elevational view of the hose fitting and corresponding undermold coupling of FIG. 7A prior to the coupling of each to the other.

Turning more specifically to FIGS. 7B and 7C, with the undermold coupling 1800 so threaded onto an end of the expiratory hose 1600, that end of the expiratory hose 1600 may be inserted into the hose interface 1580 of the expiratory inlet fitting 1500. As a result, the tubular portion 1881 of undermold coupling 1800 is inserted into the hose interface 1580 and becomes interposed between the external surface of that end of the expiratory hose 1600 and the internal surface of the hose interface 1580 of the expiratory inlet fitting 1500. As depicted in most clearly in FIGS. 7B and 7C, as such insertion occurs, each grating 1885 of the undermold coupling 1800 may be pulled away from the tubular portion 1881 (relying on the flexibility of the grating supports 1884 to act somewhat like hinges) and caused to extend over exterior portions of the expiration inlet fitting 1500 in the vicinity of the hose interface 1580. With each grating 1885 so positioned over its corresponding grating 1586, the grating 1885 may then be allowed to return to a position alongside and parallel to the external surface of the tubular portion 1881 of the undermold coupling 1800.

Figure 7D:
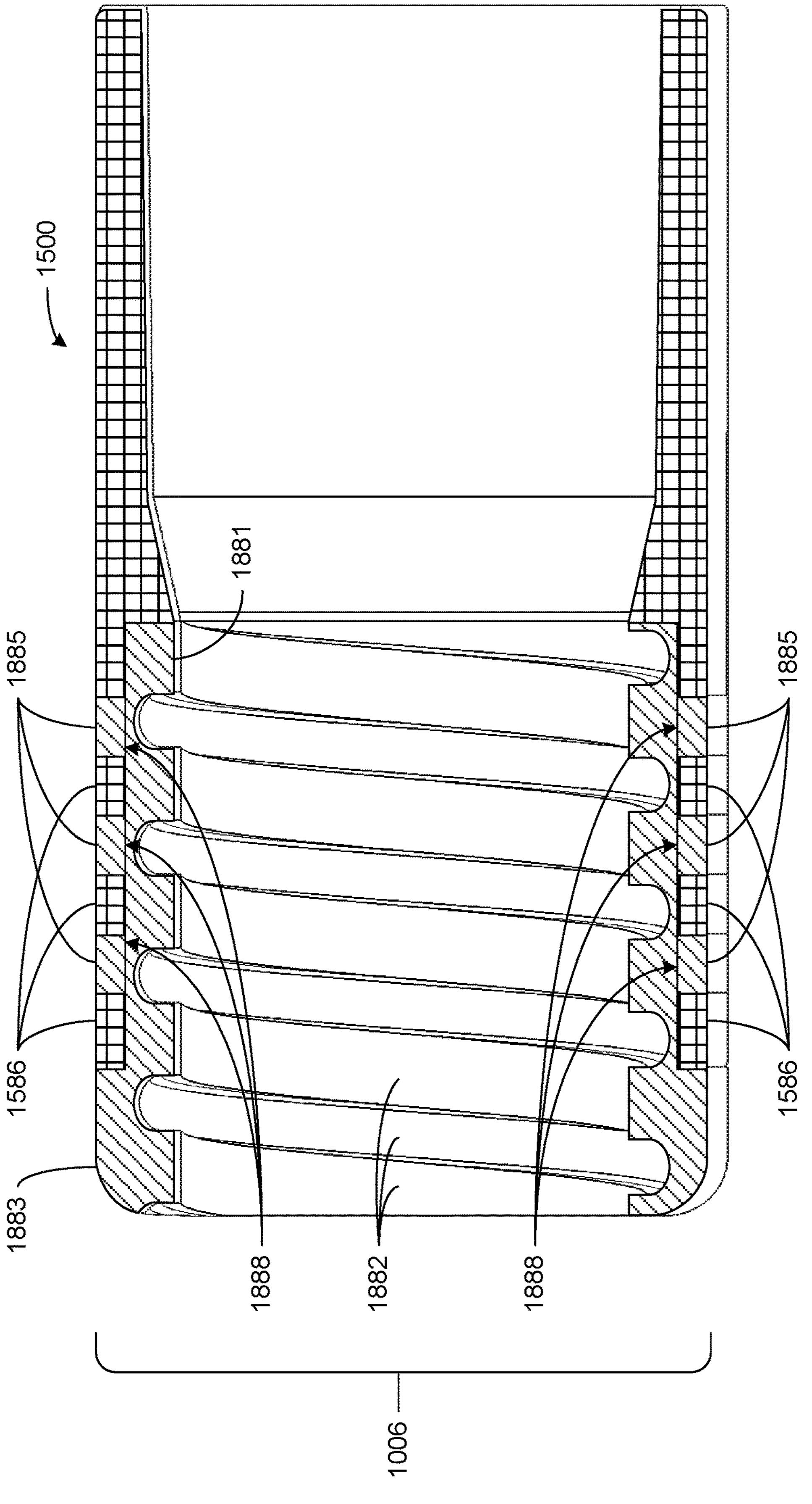
FIG. 7D is a cross-sectional view of the hose fitting and corresponding undermold coupling of FIG. 7A during the coupling of one to the other.
Figure 7E:
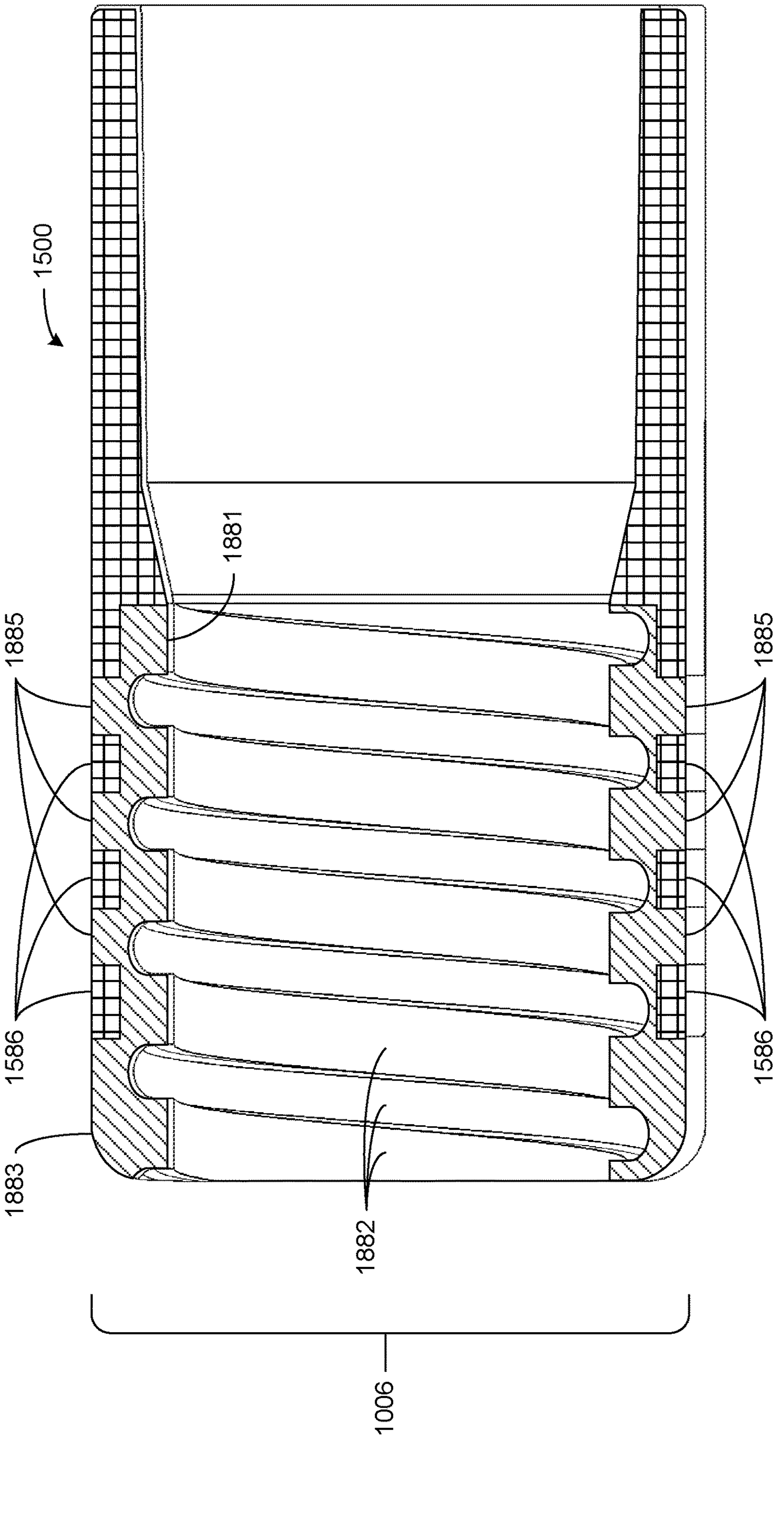
FIG. 7E is another cross-sectional view, similar to FIG. 5D, of the hose fitting and corresponding undermold coupling of FIG. 5A during the coupling of one to the other.

As depicted most clearly in FIG. 7D, with the each of the gratings 1885 allowed to return to a position alongside and parallel to the external surface of the tubular portion 1881 while each of the gratings 1885 is positioned over its corresponding grating 1586, the corresponding ones of the one or more gratings 1885 and 1586 are caused to intermesh in a manner that mechanically locks the undermold coupling 1800 within the hose interface 1580. More specifically, in each such interlock between a corresponding pair of gratings 1885 and 1586, each of the elongate portions of a grating 1885 of the undermold coupling 1800 extends into a corresponding slot 1585 defined by the corresponding grating 1586 of the expiratory inlet fitting 1500, and each of the elongate portions of that corresponding grating 1586 extends into a corresponding slot 1886 defined by the grating 1885.

As a result, the inwardly facing surfaces 1888 of each of the one or more curved elongate portions of the flexible plastics material of the undermold coupling that define each of the gratings 1885 is allowed to be brought back into contact with a portion of the external surface of the tubular portion 1881, as most clearly depicted in FIG. 7D. With such surface contacts once again made, while the one or more corresponding pairs of the gratings 1885 and 1586 are so intermeshed, heat may be applied to soften at least the undermold coupling 1800 to cause the inwardly facing surfaces 1888 of those portions of the one or more gratings 1885 that are once again in contact with the external surface of the tubular portion 1881 to become bonded to the exterior of the tubular portion 1881, as most clearly depicted in FIG. 7E. Such heating may also more broadly bond the materials of the thread-like exterior of the end of the expiratory hose 1600 (onto which the undermold coupling 1800 is threaded) to surfaces of the threads 1882 formed within the undermold coupling 1800, and such heating may also more broadly bond the material of the exterior surface of the tubular portion 1881 of the undermold coupling 1800 to the interior surface of the expiration inlet fitting 1500 into which the undermold coupling 1800 is inserted. As a result, gas-tight seals may be formed among these components.

In other embodiments, an end of the expiratory hose 1600 may be inserted into the hose interface 1580 of the expiratory inlet fitting 1500 without an undermold coupling 1800 threaded thereon. After such insertion, the flexible material of the undermold coupling 1800, in molten form, may be injected into one or more of the slots 1585 of one or more gratings 1586 of the hose interface 1580 to fill the space between the thread-like external surface of that end of the expiratory hose 1600 and the interior surface of the hose interface 1580 to form the undermold coupling 1800 in place therebetween, as well as to fill each of the slots 1585. Alternatively, the flexible material of the undermold coupling 1800, in molten form, may be injected therein between the expiratory hose 1600 and the edge of the interior surface of the hose interface 1580, where the expiratory hose 1600 enters into the hose interface 1580, to form the undermold coupling 1800 in place, as well as to fill each of the slots 1585 from within the interior of the hose interface 1580. Regardless of the exact manner in which the molten form of the material of the undermold coupling 1800 is injected to form the undermold coupling 1800 in place, in so forming the undermold coupling 1800 in place, the molten form of the undermold coupling 1800 may bond to the materials of thread-like external surface at the end of the expiratory hose 1600 and the interior surface of the hose interface 1580 to form a gas-tight seal therebetween.

It should be noted that although FIGS. 7A through 7E depict these features in a manner that is focused on the connection of an end of the expiratory hose 1600 to the expiratory inlet fitting 1500, the very same coupling arrangement just described may be employed to couple the other end of the expiratory hose 1600 to the expiratory outlet fitting 1700, and/or one or both ends of the inspiratory hose

1200 to one or both of the inspiratory inlet fitting 1100 and the inspiratory outlet fitting 1300. Stated differently, and as depicted most clearly in each of FIGS. 1D, 1E and 3A, multiple ones of the undermold coupling 1800 may be employed to couple each of the fittings 1100 and 1300 to opposite ends of the inspiratory hose 1200, and to couple each of the fittings 1500 and 1700 to opposite ends of the expiratory hose 1600.

FIGS. 8A through 8G, taken together, depict various aspects of incorporating the plug 1180 or 1780 incorporating the electrical connector 1190 or 1790 into one of the three connections provided by the inspiratory inlet fitting 1100 or the expiratory outlet fitting 1700, respectively. Also depicted are various aspects of the direct electrical coupling of the heating wires 1290 or 1690 to the electrical connector 1190 or 1790, respectively.

Figure 8A:
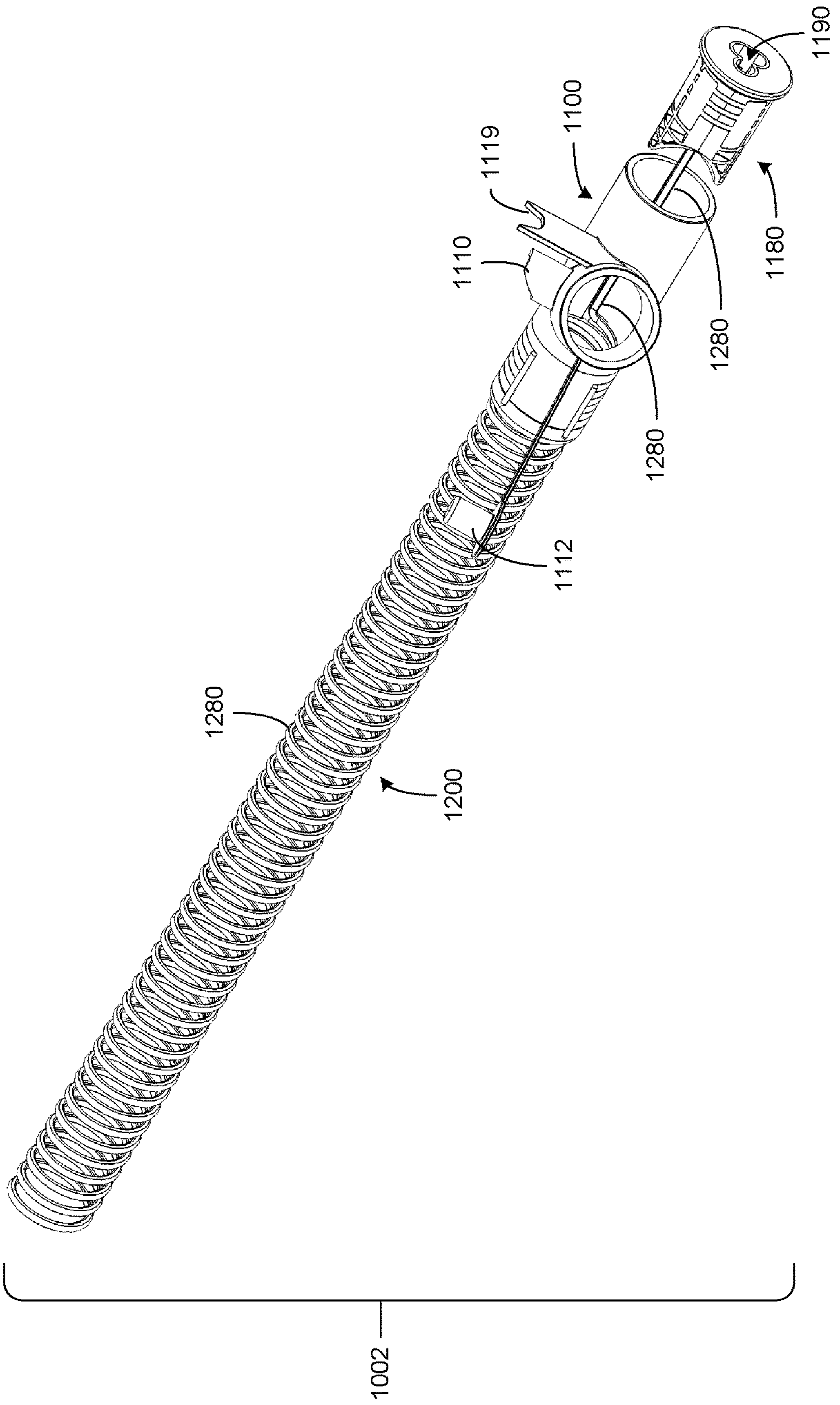
FIG. 8A is a partial perspective view of the inspiratory hose assembly of the heated respiratory hose assembly of FIG. 1A showing details of the electrical connection of an unwound end of the support helix of the hose thereof to an electrical connector carried within a plug within a hose fitting thereof.
Figure 8B:
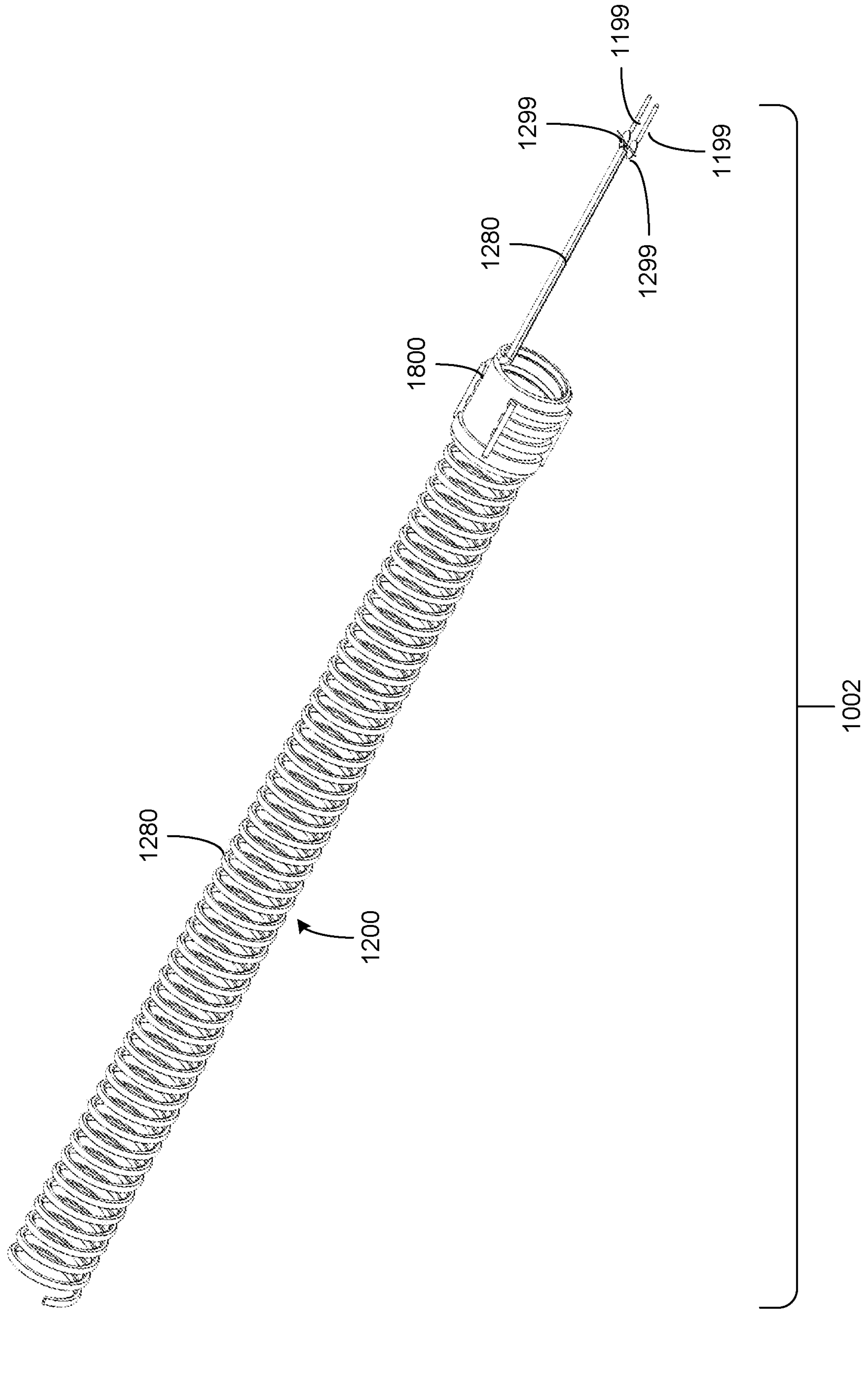
FIG. 8B is another partial perspective view of the inspiratory hose assembly of FIG. 8A showing further details of the electrical connection of the unwound end of the support helix to the electrical connector.

Each of FIGS. 8A and 8B depicts a subset of the components of the inspiratory hose assembly 1002 toward the end thereof that is to be connected to the medical device 990. More precisely, FIGS. 8A and 8B each depict the path followed by the support helix 1280 within the inspiratory hose 1200 and where an end of the inspiratory hose 1200 is coupled to the inspiratory inlet fitting 1100. The wall 1270 of the inspiratory hose 1200 has been omitted in both of these views for purposes of visual clarity. Additionally, in FIG. 8B, both the plug 1180 and the insulating shroud portion of the electrical connector 1190 have been omitted, also for purposes of visual clarity. As depicted, where an end of a portion of the inspiratory hose 1200 is inserted into a portion of the inspiratory inlet fitting 1100, a relatively short portion of the support helix 1280 is unwound from its helical path within the inspiratory hose 1200 and is employed as an electrical cable to bring the heating wires 1290 therein to the electrical connector 1190 within the plug 1180.

More specifically, a relatively short portion of the support helix 1280 is pulled out of the end of the inspiratory hose 1200 (i.e., unwound therefrom) where that end is inserted into the inspiratory inlet fitting 1100, and straightened to at least some degree for use as an electrical cable to bring the heating wires 1290 therein directly to the electrical connector 1190. This unwinding of the relatively short portion of the support helix 1280 may be performed prior to the threading of the depicted undermold coupling 1800 onto the end of the inspiratory hose 1200 that is to be inserted into the inspiratory inlet fitting 1100. As a result, the relatively short unwound portion of the support helix 1280 extends beyond the end of the inspiratory hose 1200 onto which the undermold coupling 1800 is threaded, thereby emerging from within the undermold coupling 1800 and extending further into the interior of the inspiratory inlet fitting 1100 than the end of the inspiratory hose 1200 onto which the undermold coupling 1800 is threaded.

The end of the relatively short portion of the support helix 1280 that extends toward the electrical connector 1190 may be partly stripped away to remove at least enough of the flexible plastics material of the support helix 1280 to expose enough of the heating wires 1290 therein to enable forming an electrical connection with the contacts 1199 of the electrical connector 1190. More precisely, the plastics material of the support helix 1280 may be stripped away in a manner that may be akin to procedures often used in preparing conventional multi-conductor cables for the connection of the individual wires therein to contacts of an electrical connector or other electrical device. Thus, typical wire stripping techniques may be employed to gain access to each of the heating wires 1290, and then the conductor 1299 (see FIG. 4B) within each of the heating wires 1290 may be soldered to a soldering tab of one of the electrical contacts 1199 of the electrical connector 1190. Additionally, if the relatively short unwound portion of the support helix 1280 is additionally covered in a sheath (e.g., heatshrink tubing that may be sleeved over the relatively short unwound portion of the support helix 1280), then part of that sheath may also be similarly stripped away using typical wire stripping techniques. As previously discussed, the conductor 1299 of each of the heating wires 1290 may be sheathed within an individual insulator 1291 that is selected to be thermally resistant to the temperatures expected to be encountered during heating of the inspiratory hose 1200, but not to the temperatures expected to be encountered during soldering, thereby eliminating the need to strip each of the conductors 1299 of their individual insulators 1291 prior to soldering each of the conductors 1299 to a soldering tab of one of the electrical contacts 1199.

In separating the relatively short portion of the support helix 1280 from the inspiratory hose 1200, portions of the wall 1270 (again, not shown for purposes of visual clarity) that extend between adjacent coils of the support helix 1280 that are included in the relatively short portion thereof may be trimmed away. After being so separated, the relatively short unwound portion of the support helix 1280 may be heated to soften the flexible plastics material thereof (i.e., to relax the molecules of the flexible plastics material thereof) to aid in straightening it out from its original helical path within the inspiratory hose 1200 (i.e., causing the molecules of the flexible plastics material of the relatively short portion of the support helix 1280 to adopt a straightened path as a new resting state).

The actual length of the relatively short portion of the support helix 1280 that emerges from the undermold coupling 1800 and extends further into the interior of the inspiration inlet fitting 1100 may be based, at least in part, on the dimensions of the inspiration inlet fitting 1100. More specifically, the length may be selected based on the length needed to extend from the undermold coupling 1800 and to the electrical connector 1190, and may include a predetermined additional length needed to allow manufacturing personnel sufficient physical access to solder the conductors 1299 of the heating wires 1290 to the soldering tabs of the electrical contacts 1199, as earlier described.

Figure 8C:
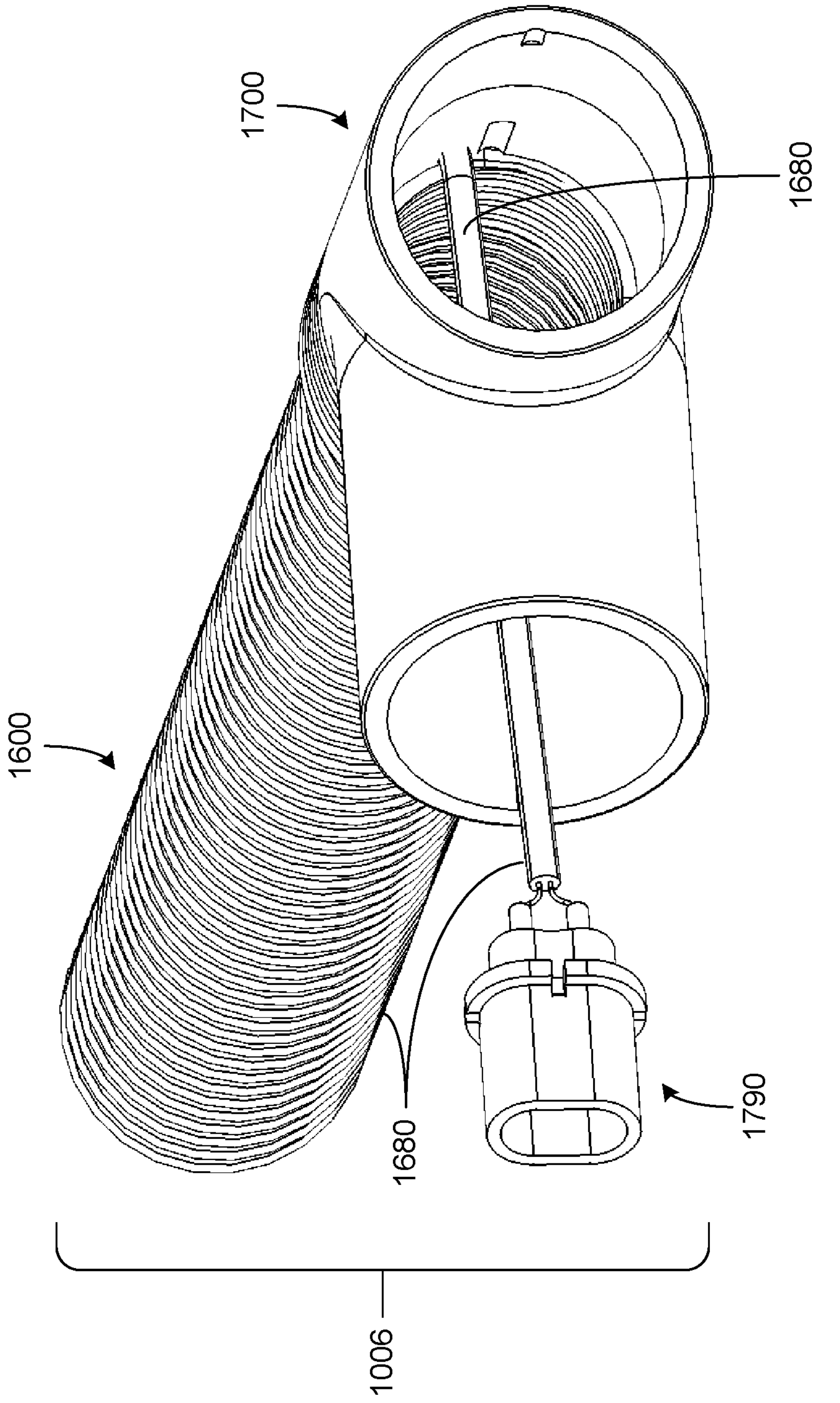
FIG. 8C is a partial perspective view of the expiratory hose assembly of the heated respiratory hose assembly of FIG. 1A showing details of the electrical connection of an unwound end of the support helix of the hose thereof to an electrical connector carried within a plug within a hose fitting thereof.

In a manner somewhat similar to FIGS. 8A and 8B, FIG. 8C depicts a subset of the components of the expiratory hose assembly 1006 toward the end thereof that is to be connected to the medical device 990. More precisely, FIG. 8C depicts the path followed by the support helix 1680 within the expiratory hose 1600 and where an end of the expiratory hose 1600 is coupled to the expiratory outlet fitting 1600. The wall 1670 of the expiratory hose 1600, the plug 1780 and the insulating shroud portion of the electrical connector 1790 have all been omitted for purposes of visual clarity. As depicted, where an end of a portion of the expiratory hose 1600 is inserted into a portion of the expiratory outlet fitting 1700, a relatively short portion of the support helix 1680 is unwound from its helical path within the expiratory hose 1600 and is employed as an electrical cable to bring the heating wires 1690 therein to the electrical connector 1790 within the plug 1780 (again, not shown).

More specifically, a relatively short portion of the support helix 1680 is pulled out of the end of the expiratory hose 1600 (i.e., unwound therefrom) where that end is inserted into the expiratory outlet fitting 1700, and straightened to at least some degree for use as an electrical cable to bring the heating wires 1690 therein directly to the electrical connector 1790. In a manner similar to what was discussed above concerning the support helix 1280, this unwinding of the relatively short portion of the support helix 1680 may be performed prior to the threading of another of the undermold couplings 1800 onto the end of the expiratory hose 1600 that is to be inserted into the expiratory outlet fitting 1700. As a result, the relatively short portion of the support helix 1680 extends beyond the end of the expiratory hose 1600 onto which the undermold coupling 1800 is threaded, thereby emerging from within the undermold coupling 1800 and extending further into the interior of the expiratory outlet fitting 1700 than the end of the expiratory hose 1600 onto which the undermold coupling 1800 is threaded.

As with the earlier discussed relatively short portion of the support helix 1280 employed as an electrical cable, the end of the relatively short unwound portion of the support helix 1680 that extends toward the electrical connector 1790 may also be partly stripped away to remove at least enough of the flexible plastics material of the support helix 1680 to expose enough of the heating wires 1690 therein to enable forming an electrical connection with the contacts 1199 of the electrical connector 1190. Again, this may also be done using typical wire stripping techniques, and again, if the stripped-away part of the unwound portion of the support helix 1680 is additionally covered in a sheath (e.g., heat-shrink tubing), part of that sheath may also be similarly stripped away using typical wire stripping techniques. Also again, in separating the relatively short portion of the support helix 1680 from the expiratory hose 1600, portions of the wall 1670 (again, not shown for purposes of visual clarity) that extend between adjacent coils of the support helix 1680 that are included in the relatively short portion thereof may be trimmed away. And again, after being so separated, the relatively short portion of the support helix 1680 may be heated to soften the flexible plastics material thereof to aid in straightening it out from its original helical path within the expiratory hose 1600.

As with the earlier discussed relatively short portion of the support helix 1280 employed as an electrical cable, the actual length of the relatively short portion of the support helix 1680 that emerges from the undermold coupling 1800 and extends further into the interior of the expiration outlet fitting 1700 may be based, at least in part, on the dimensions of the expiration outlet fitting 1700. More specifically, the length may be selected based on the length needed to extend from the undermold coupling 1800 and to the electrical connector 1790, and may include a predetermined additional length needed to allow manufacturing personnel sufficient physical access to solder the conductors 1699 of the heating wires 1690 to the soldering tabs of the electrical contacts 1799.

Such use of a portion of the support helixes 1280 and/or 1680, as if each were a conventional two-conductor electric cable, advantageously avoids the creation of electrical terminations where a transition is made between the heating wires 1290 and/or 1690 of the support helixes 1280 and/or 1680 to non-heating wires that travel a relatively short distance within the fittings 1100 and/or 1300 to electrically couple the heating wires 1290 and/or 1690 to the electrical connectors 1190 and/or 1790, respectively. Experience has shown that such electrical terminations to transition between heating and non-heating wires can be a source of potentially dangerous electrical failures. Poorly implemented electrical terminations of this type can actually have a higher resistance than the heating wires 1290, themselves, such that the terminations can become hotter than either the heating wires 1290 or 1690. This may lead to such hazards as burning through the plastics material of the inspiratory inlet fitting 1100 and/or otherwise generating toxic smokes/gases within the inspiratory inlet fitting 1100 that may be inhaled by the patient. It has been discovered through testing that such a transition between heating and non-heating wires is unnecessary, and that portions of the support helixes 1280 and 1680 can be used as multi-conductor cables, as has been described.

Figure 8D:
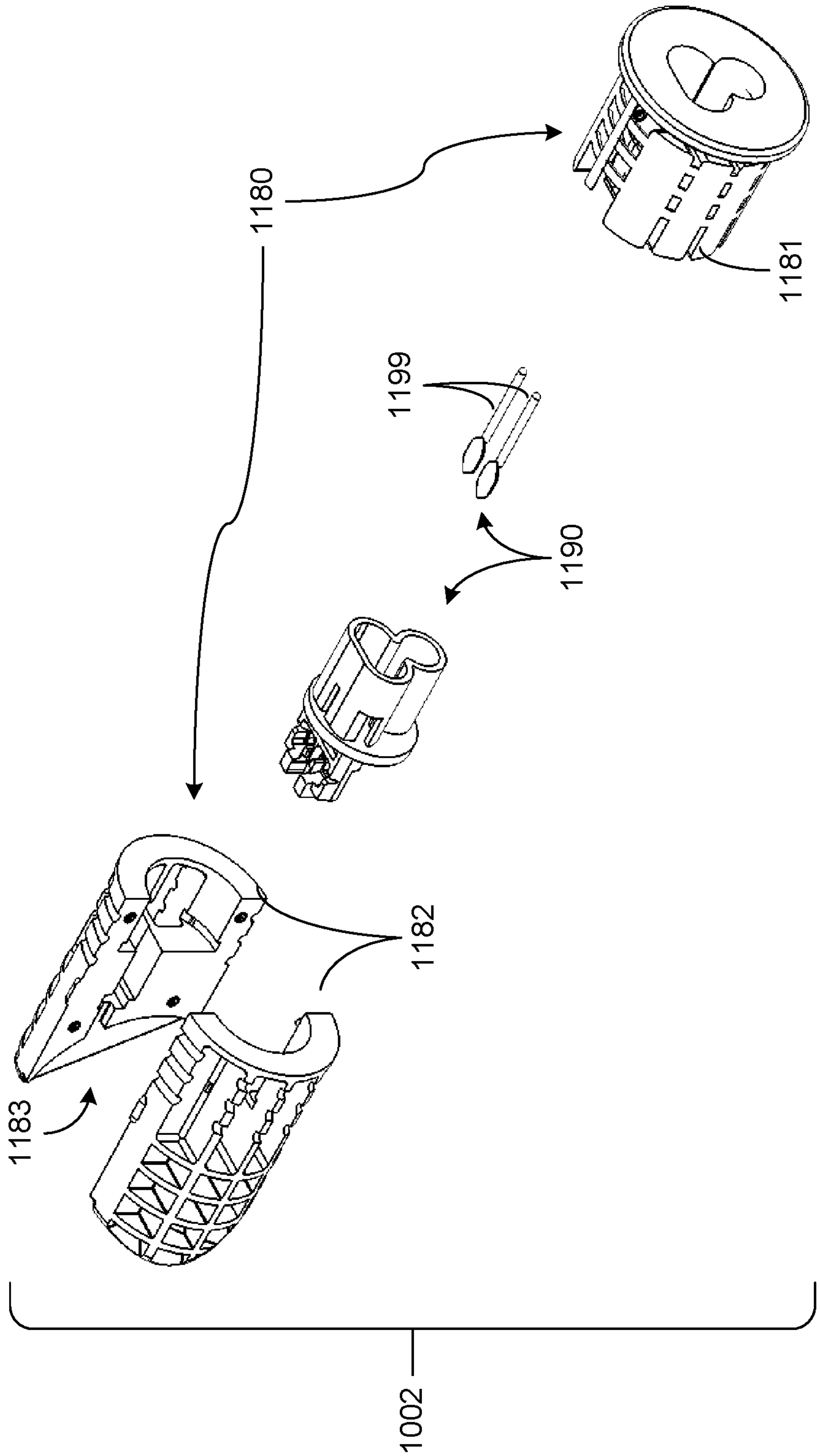
FIG. 8D is an exploded perspective view of the combination of the plug and electrical connector of the inspiratory hose assembly of FIGS. 8A and 8B showing details of the manner in which the plug may be assembled from multiple pieces around the electrical connector.
Figure 8E:
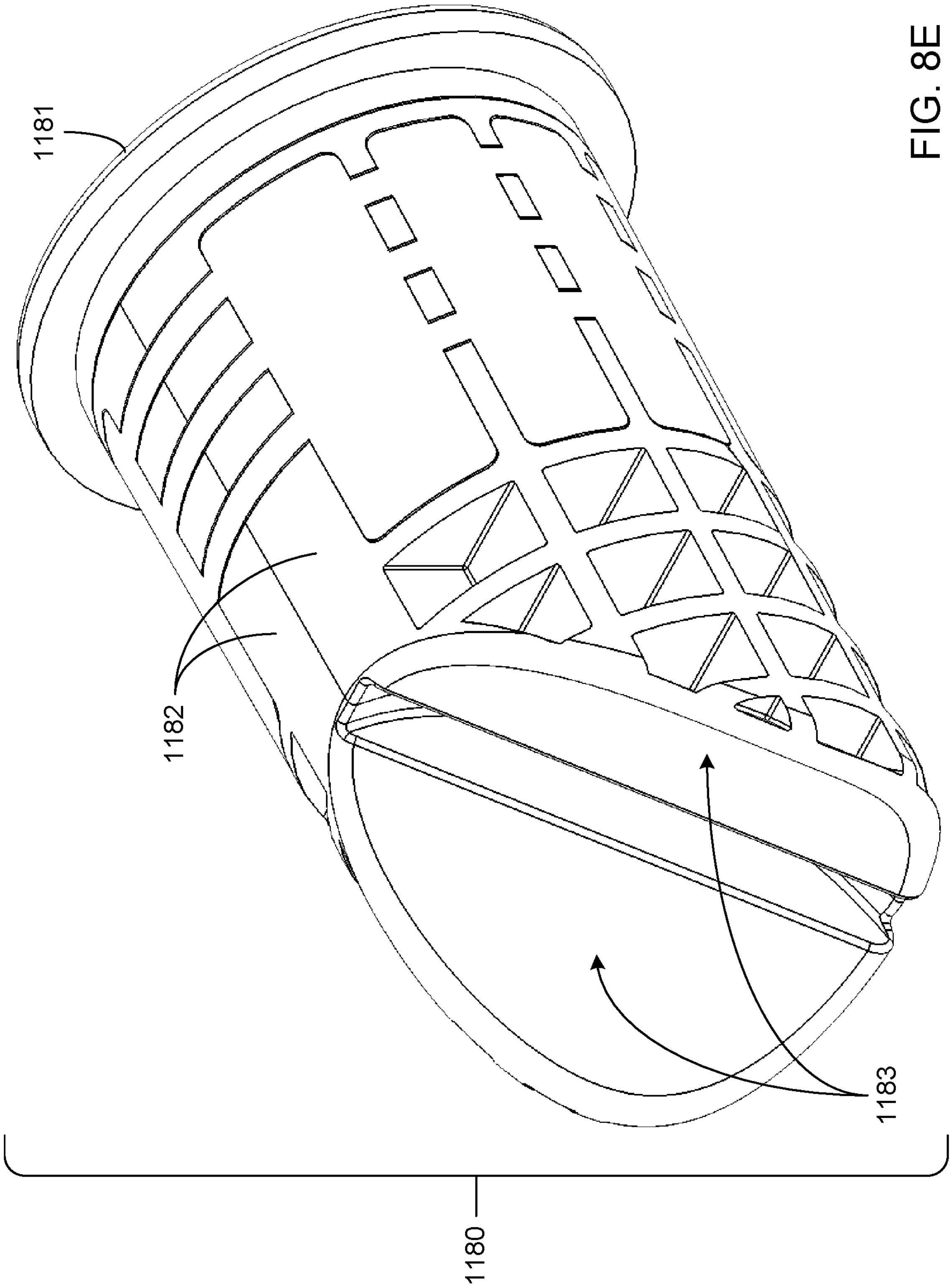
FIG. 8E is a perspective view of the plug of the inspiratory hose assembly of FIGS. 8A and 8B showing details of the shaping of the plug improve the flow of respiratory gases through the inspiratory hose assembly.

FIGS. 8D and 8E, taken together, depict various features of the plug 1180 and the electrical connector 1190 carried therein. As depicted, in some embodiments, the plug 1180 may be formed from multiple separately fabricated plastic components, including the depicted face portion 1181 and the depicted pair of "clamshell" portions 1182. In this depicted embodiment, much of the electrical connector 1190 (with its electrical contacts 1199 installed therein, and already soldered to the conductors 1299 of the heating wires 1290 of the support helix 1280) may be enclosed between the two clamshell portions 1182, which may be fastened to each other in any of a variety of ways. A portion of the support helix 1280 adjacent the electrical connector 1190 may also be enclosed between the two clamshell portions 1182. The face portion 1181 may then be molded over the assembled pair of the clamshell portions 1182 with the electrical connector 1190 enclosed between the clamshell portions 1182. In so molding the face portion 1181, portions of the plastics material of the face portion 1181, while in a molten state, may fill various convolutions formed within each of the two clamshell portions 1182 to further bond them together. In so doing, the face portion 1181 may also seal spaces between the two clamshell portions 1182 within which the electrical connector 1190 is held, as well as the portion of the support helix that is also enclosed therebetween. In so doing, the electrical connections between the conductors 1299 of the heating wires 1290 and the electrical contacts 1199 of the electrical connector 1190 may be entirely enclosed to seal and protect those connections against moisture present in the respiratory gases conveyed through the inspiratory inlet fitting 1100 to thereby prevent corrosion, etc.

Alternatively, in other embodiments, following the connection of the conductors 1299 of the heating wires 1290 of the support helix 1280 to the electrical contacts 1199 of the electrical connector 1190, the entire plug 1180 may simply be molded around the electrical connector 1190. A portion of the support helix 1280 adjacent the electrical connector 1190 may also be enclosed within such a molded form of the plug 1180.

Regardless of the exact manner in which the plug 1180 is formed and/or in which the electrical connector 1190 is caused to be enclosed within the plug 1180, the portion of the plug 1180 that extends furthest into the inspiration inlet fitting 1100 may be shaped to cooperate with interior surface portions of the inspiration inlet fitting 1100 to present a relatively unobstructed path for the flow of respiratory gases through the inspiration inlet fitting 1100 with relatively smooth surfaces encountered by the respiratory gases throughout that path. More precisely, and as best seen in FIG. 8E, as well as in FIGS. 1D, 1E and 8A, the portion of the plug 1180 that extends furthest into the inspiration inlet fitting 1100 may be provided with a concave surface 1183 that serves to define part of such a relatively unobstructed path with smooth surfaces for the flow of respiratory gases.

Figure 8F:
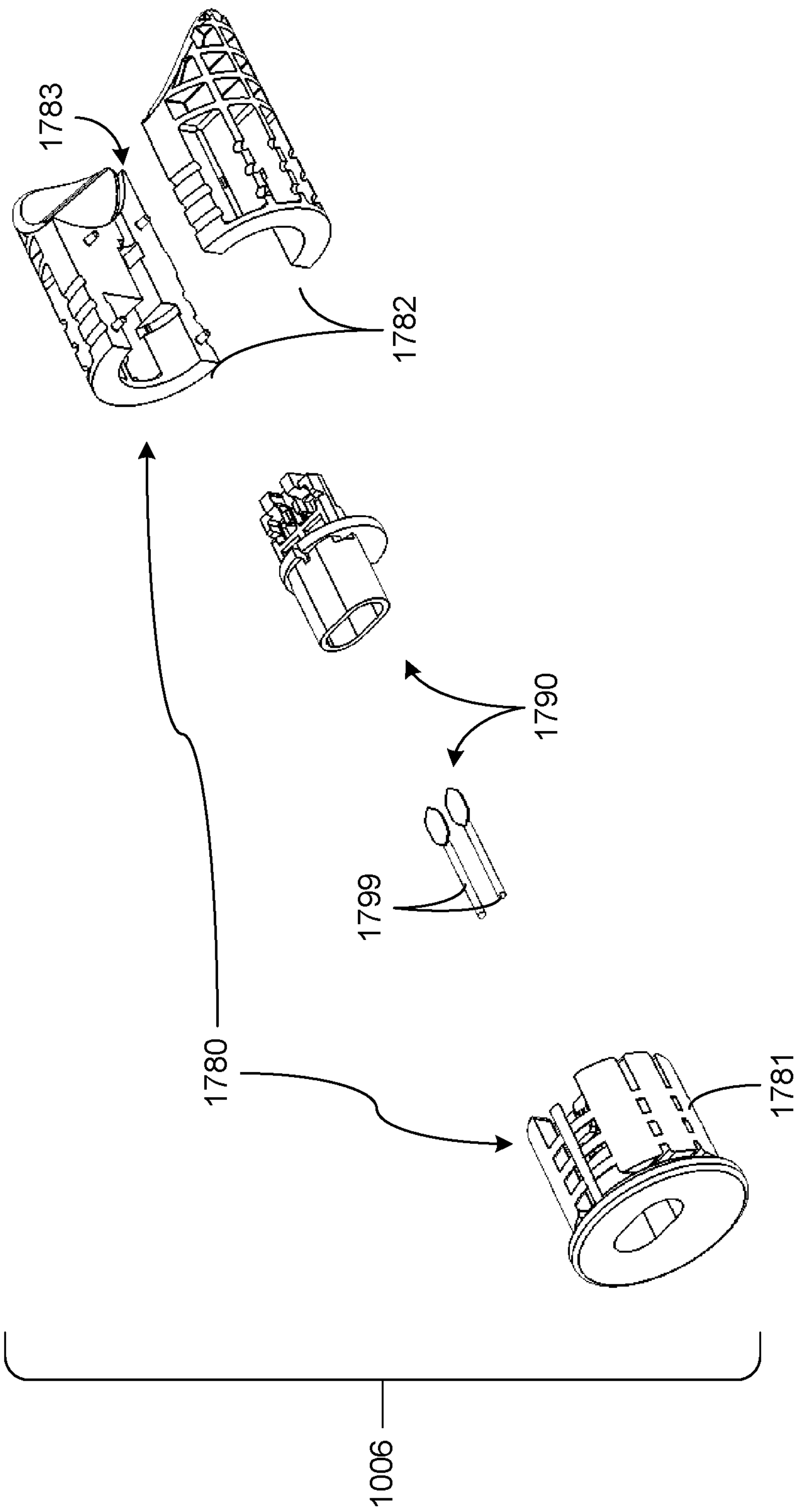
FIG. 8F is an exploded perspective view of the combination of the plug and electrical connector of the expiratory hose assembly of FIG. 8C showing details of the manner in which the plug may be assembled from multiple pieces around the electrical connector.
Figure 8G:
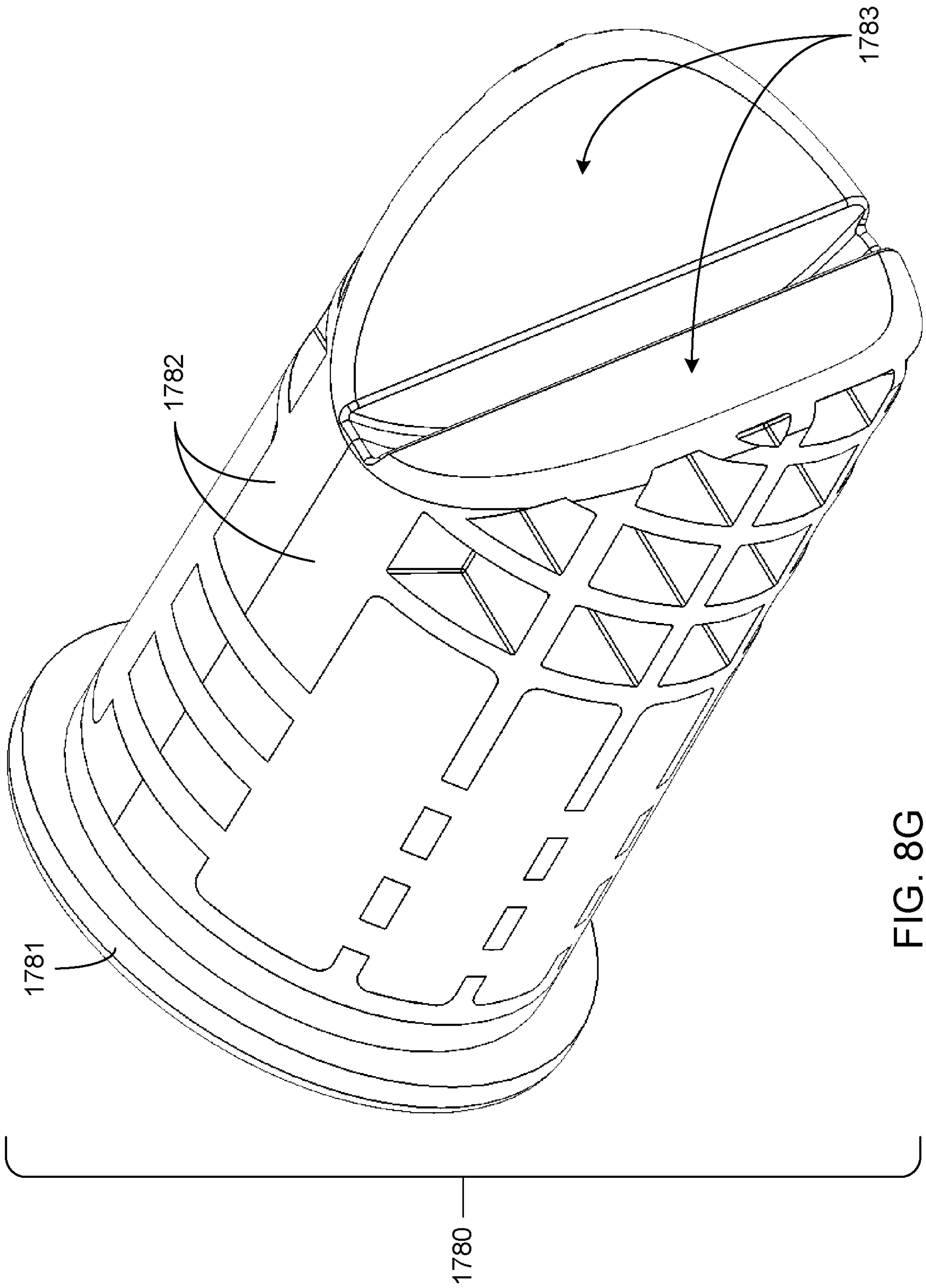
FIG. 8G is a perspective view of the plug of the expiratory hose assembly of FIG. 8C showing details of the shaping of the plug improve the flow of respiratory gases through the inspiratory hose assembly.

FIGS. 8F and 8G, taken together, depict similar features of the plug 1780 and the electrical connector 1790 carried therein. As depicted, in some embodiments, the plug 1780 may be formed from multiple separately fabricated plastic components, including the depicted face portion 1781 and the depicted pair of clamshell portions 1782. In this depicted embodiment, much of the electrical connector 1790 (with its electrical contacts 1799 installed therein, and already soldered to the conductors 1699 of the heating wires 1690 of the support helix 1680) may be enclosed between the two clamshell portions 1782, which may be fastened to each other in any of a variety of ways. A portion of the support helix 1680 adjacent the electrical connector 1790 may also be enclosed between the two clamshell portions 1782. The face portion 1781 may then be molded over the assembled pair of the claims clamshell portions 1782 to form the plug 1780 with the electrical connector 1790 sealed in place therein in a manner similar to what has been previously described in reference to the plug 1180.

Alternatively, in other embodiments, following the connection of the conductors 1699 of the heating wires 1690 of the support helix 1680 to the electrical contacts 1799 of the electrical connector 1790, the entire plug 1780 may simply be molded around the electrical connector 1790. A portion of the support helix 1680 adjacent the electrical connector 1790 may also be enclosed within such a molded form of the plug 1780.

As with the plug 1180, regardless of the exact manner in which the plug 1780 is formed and/or in which the electrical connector 1790 is caused to be enclosed within the plug 1780, the portion of the plug 1780 that extends furthest into the expiration outlet fitting 1700 may be shaped to cooperate with interior surface portions of the expiration outlet fitting 1700 to present a relatively unobstructed path for the flow of respiratory gases through the expiration outlet fitting 1700 with relatively smooth surfaces encountered by the respiratory gases throughout that path. More precisely, and as best seen in FIG. 8G, as well as in FIGS. 1D and 1E, the portion of the plug 1780 that extends furthest into the inspiration inlet fitting 1700 may be provided with a concave surface 1783 that serves to define part of such a relatively unobstructed path with smooth surfaces for the flow of respiratory gases.

It should be noted that, as depicted in FIGS. 8D and 8F, as well as throughout others of the figures in this present application, the electrical connectors 1190 and 1790 may be provided with differing physical shapes as a keying mechanism to prevent incorrect electrical connections between the medical device 990 and each of the heating wires 1290 and 1690 within the hoses 1200 and 1600, respectively. More specifically, the electrical connector 1190 is depicted as being a so-called "monkey face" connector having a shape that includes three lobes in which two of the lobes are each occupied by one of the electrical contacts 1199. In contrast, the electrical connector 1790 is depicted as having a more conventional elongate oval-like shape in which the electrical contacts 1799 are positioned toward opposite ends of the of the oval-like shape. As will be familiar to those skilled in the art of such medical devices as ventilators and CPAP devices, this depicted combination of forms of the electrical connectors 1190 and 1790 have become widely adopted for use in providing electric power for heating the hoses used with such medical devices.

As previously discussed, at the opposite end of the support helix 1280 from the end that is connected to the electrical connector 1190, the conductors 1299 of the pair of heating wires 1290 may be electrically connected to each other through crimping, soldering, etc., to form an electrical loop with the pair of heating wires 1290 through the support helix 1280 for heating the interior of the inspiration hose 1200. Similarly, at the opposite end of the support helix 1680 from the end that is connected to the electrical connector 1790, the conductors 1699 of the pair of heating wires 1690 may be similarly electrically connected to each other to form a separate electrical loop with the pair of heating wires 1690 through the support helix 1680 for separately heating the interior of the expiration hose 1600. As also previously discussed, the medical device 990 may operate each of these electrical loops separately and in different ways that may be selected to cause differing degrees of heating within each of the hoses 1200 and 1600. Indeed, as also previously discussed, the heating wires 1290 and 1690 may be selected to have different resistances in recognition of such differences in the manner in which each may be used.

Figure 9A:
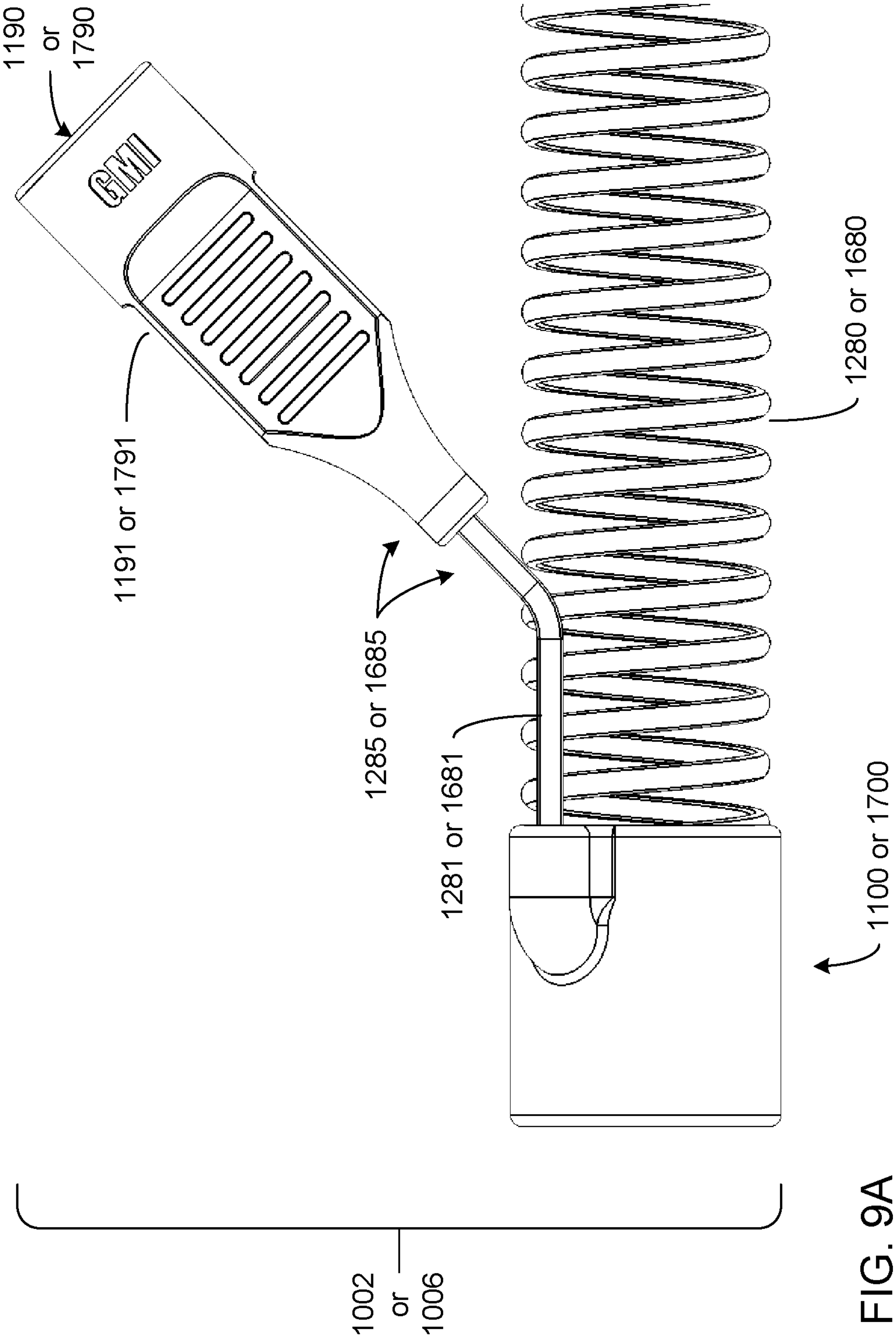
FIG. 9A is a partial elevational view of either the inspiratory hose assembly or the expiratory hose assembly of the embodiment of the heated respiratory hose assembly of FIG. 3B.
Figure 9B:
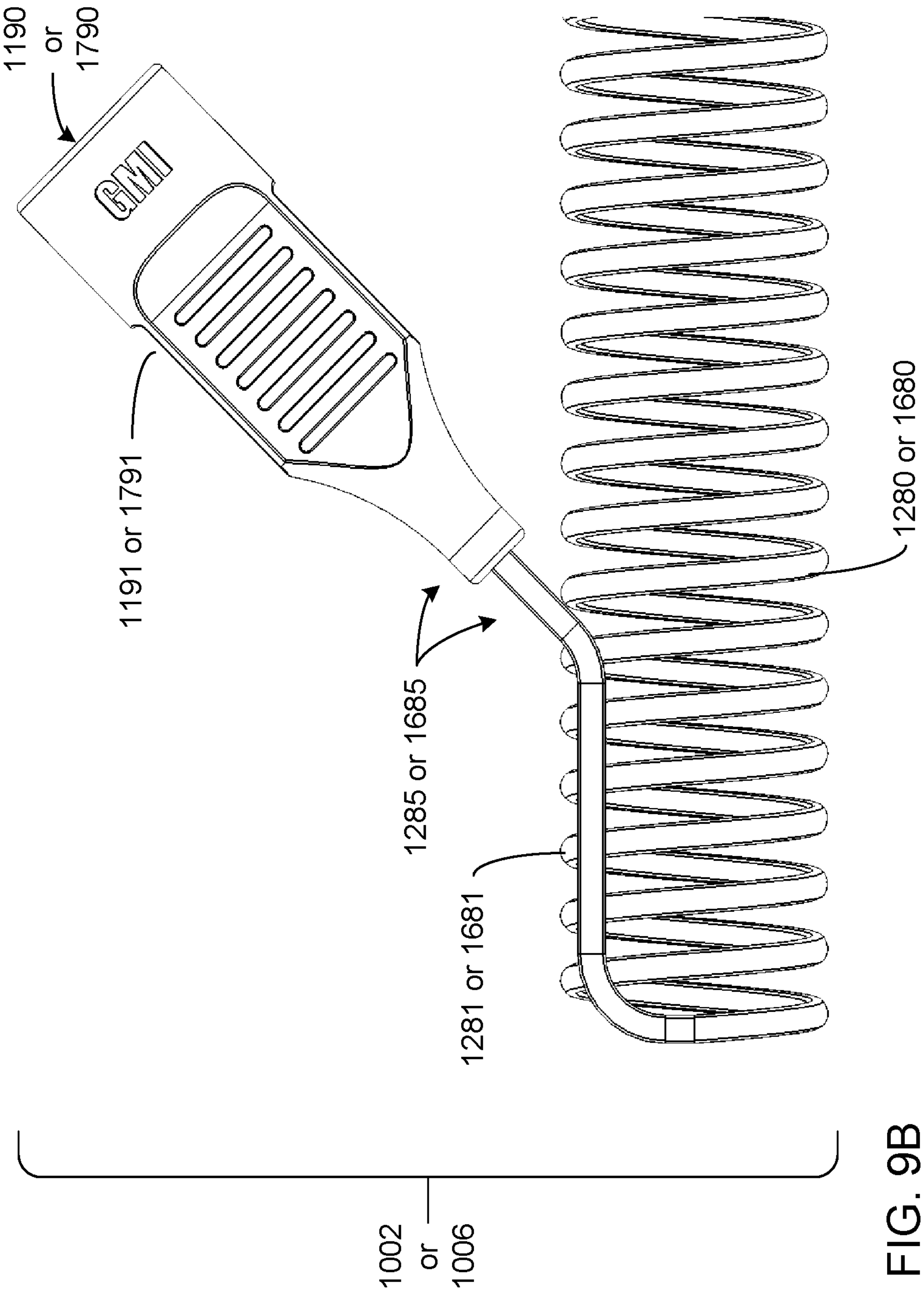
FIG. 9B is another partial elevational view of either the inspiratory hose assembly or the expiratory hose assembly of the embodiment of the heated respiratory hose assembly of FIG. 3B showing details of the manner in which the support helix is shaped and positioned within a hose fitting as part of forming a pigtail.
Figure 9C:
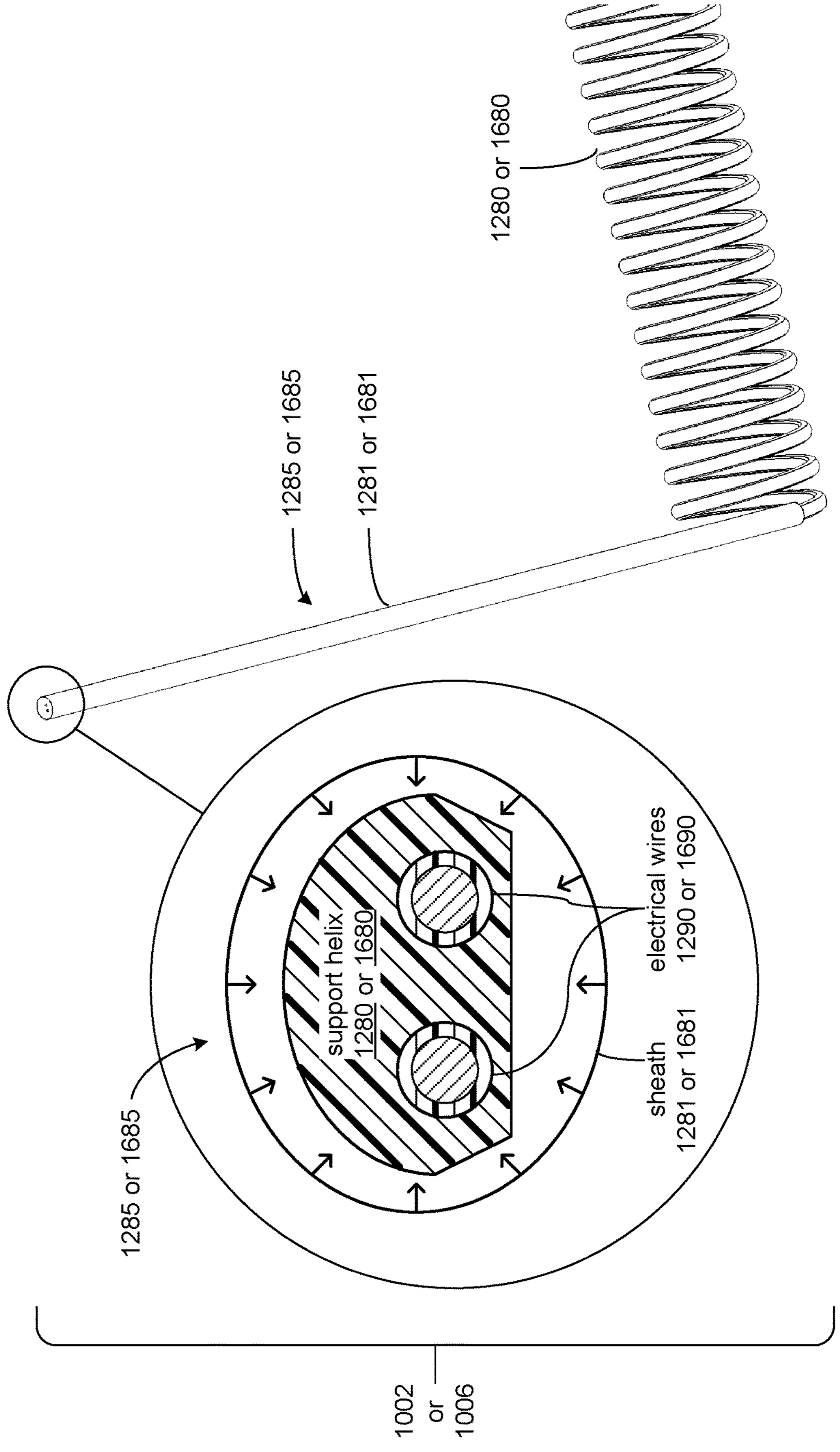
FIG. 9C is a combination of perspective and cross-sectional views of a portion of a pigtail of one of the hoses of either of the embodiments of heated respiratory hose assembly of any of FIG. 3B or 3C showing details of the formation of the pigtail from a portion of an unwound end of a support helix.

FIGS. 9A through 9C, taken together, depict various aspects of forming an electrical "pigtail" 1285 or 1685 from a portion of the support helix 1280 or 1680 for use in connecting the heating wires 1290 or 1690 to the medical device 990 to be provided with electrical power therefrom. In a manner similar to the embodiments depicted and discussed in reference to FIGS. 8A through 8G, FIGS. 9A through 9C present embodiments of the use of a portion of the support helix 1280 or 1680 as an electrical cable to advantageously avoid the creation of a electrical terminations where a transition is made between the heating wires 1290 or 1690, respectively, to non-heating wires. However, unlike the embodiments of FIGS. 8A through 8G in which the connector 1190 or 1790 is carried within the plug 1180 or 1780 installed within the fitting 1100 or 1700, respectively, in the embodiments of FIGS. 9A through 9C, the connector 1190 or 1790 is located in the environment external to the fitting 1100 or 1700 at the end of an electrical pigtail 1285 or 1685, respectively.

Each of FIGS. 9A through 9C depicts a subset of the components of either the inspiratory hose assembly 1002 or the expiratory hose assembly 1006 toward the end thereof that is to be connected to the medical device 990. More precisely, in each of FIGS. 9A through 9C, depictions of one of the undermold couplings 1800, and of the wall 1270 or 1670 of the hose 1200 or 1600 has been omitted to enable the helical path of the support helix 1280 or 1680, respectively, therein to be viewed more clearly. Additionally, in FIG. 9B, the depiction of either the inspiratory inlet fitting 1100 or the expiratory outlet fitting 1700 that is provided in FIG. 9A is also omitted to provide an uninterrupted view of the transition of the support helix 1280 or 1680 from its helical path for purposes of heating the interior of the hose 1200 or 1600 to a relatively straightened path for purposes of being used as an electrical cable to convey the heating wires 1290 or 1690 thereof to the connector 1190 or 1790.

Turning more specifically to FIGS. 9A and 9B, as depicted, where an end of a portion of the inspiratory hose 1200 is inserted into a portion of the inspiratory inlet fitting 1100, or where an end of a portion of the expiratory hose 1600 is inserted into a portion of the expiratory outlet fitting 1700, a portion of the support helix 1280 or 1680 is unwound from its helical path within the inspiratory hose 1200 or 1600 and is employed as an electrical cable to bring the heating wires 1290 or 1690 therein to the electrical connector 1190 or 1790 at an end of the electrical pigtail 1285 or 1685, respectively.

More specifically, a portion of the support helix 1280 or 1680 is pulled out of the end of the hose 1200 or 1600 (i.e., unwound therefrom) where that end is inserted into the fitting 1100 or 1700, respectively. The length of the unwound portion of the support helix 1280 or 1680 may be determined, at least in part, by the intended length of the electrical pigtail 1285 or 1685. The unwound portion of the support helix 1280 or 1680 may then be straightened to at least some degree for use as an electrical cable. This unwinding of the portion of the support helix 1280 may be performed prior to the threading of the depicted undermold coupling 1800 (again, not shown for purposes of visual clarity) onto the end of the hose 1200 or 1600 that is to be inserted into the fitting 1100 or 1700, respectively. As a result, the unwound portion of the support helix 1280 extends beyond the end of the 1200 or 1600 onto which the undermold coupling 1800 is threaded, thereby emerging from within the undermold coupling 1800 and extending further into the interior of the 1100 or 1700 than the end of the hose 1200 or 1600, respectively, onto which the undermold coupling 1800 is threaded. The unwound portion of the support helix 1280 or 1680 may then be fed through a channel and/or opening defined by a portion of the fitting 1100 or 1700 to be caused to extend into the environment external to the fitting 1100 or 1700 to serve as the core of the electrical pigtail 1285 or 1685.

Turning briefly to FIG. 9C, as depicted, the unwound portion of the support helix 1285 or 1685 may be covered in a sheath 1281 or 1681, at least where the unwound portion of the support helix 1285 or 1685 emerges from the fitting 1100 or 1700, respectively, and into the environment external thereto. Alternatively or additionally, the sheath 1281 or 1681 may cover at least part of the unwound portion of the support helix 1285 or 1685 within the fitting 1100 or 1700. In some embodiments, the sheath 1281 or 1681 may be a length of heatshrink tubing that is sleeved over the unwound portion of the support helix 1285 or 1685 (at least the length thereof that is within the environment external to the fitting 1200 or 1600), and then heated to cause the cross-section of the heatshrink tubing to shrink radially inward toward the exterior of the unwound portion of the support helix 1285 or 1685. Such an application of heat may also be used to aid in the straightening of the unwound portion of the support helix 1280 or 1680 and/or to somewhat change the shape thereof to conform to the interior surface of the heatshrink tubing as the heatshrink tubing is caused to tightly surround the unwound portion of the support helix 1285 or 1685, respectively (at least the length thereof that is within the environment external to the fitting 1200 or 1600).

Turning again more specifically to FIGS. 9A and 9B, the end of the unwound portion of the support helix 1280 or 1680 that extends toward the electrical connector 1190 or 1790 may be partly stripped away to remove at least enough of the flexible plastics material of the support helix 1280 or 1680 (and maybe also to strip away a portion of the sheath 1281 or 1681) to expose enough of the heating wires 1290 or 1690 therein to enable forming an electrical connection with the contacts 1199 or 1799 of the electrical connector 1190 or 1790, respectively. Again, this may also be done using typical wire stripping techniques. Also again, in separating the relatively short portion of the support helix 1280 or 1680 from the hose 1200 or 1600, portions of the wall 1270 or 1670 (again, not shown for purposes of visual clarity) that extend between adjacent coils of the support helix 1280 or 1680 that are included in the unwound portion thereof may be trimmed away.

It has been discovered through testing that a transition from the heating wires 1290 or 1690 of the support helix 1280 or 1680, and to non-heating wires to form the electrical pigtail 1285 or 1685 is unnecessary, especially where the electrical pigtail 1285 or 1685 additionally includes the sheath 1281 or 1681 to provide additional insulation against the heat that may be generated within the electrical pigtail 1285 or 1685 by the heating wires 1290 or 1690, respectively, therein.

Although the invention has been described in a preferred form with a certain degree of particularity, it is understood that the present disclosure of the preferred form has been made only by way of example, and that numerous changes in the details of construction and the manner of manufacture may be resorted to without departing from the spirit and scope of the invention. It is intended to protect whatever features of patentable novelty exist in the invention disclosed.

The invention claimed is:

1. A method of forming a hose comprising:
extruding a continuous web of plastics material from a first extruder of a hose making apparatus;
helically winding the extruded web about a mandrel or at least one rotating rod of the hose making apparatus to form a wall of the hose about a central axis of the hose;
extruding a first continuous bead of plastics material to have a first cross-section that defines a first lumen at a first location within the first cross-section;
cooling the first extruded bead sufficiently to cool the plastics material adjacent the first location within the first cross-section of the first extruded bead to cause the first lumen to retain its size and shape within the first cross-section;
re-heating the first extruded bead sufficiently to cause outer surface portions of the plastics material of the first extruded bead to become molten; and
helically winding the first extruded bead onto and about an external surface of the wall to provide the wall a first support helix.

2. The method of claim 1, wherein cooling the first extruded bead comprises:
routing the first extruded bead through a cooling liquid; and
maintaining the cooling liquid at a temperature that is selected to be sufficiently lower than a temperature of the first extruded bead at a second extruder as to cool the plastics material adjacent the first location within the cross-section of the first extruded bead to cause the first lumen to retain its size and shape within the first cross-section, and without causing cracking of the plastics material of the first extruded bead.

3. The method of claim 2, wherein maintaining the cooling liquid at the selected temperature comprises maintaining the cooling liquid within an elongate trough that is open to ambient air that surrounds the trough to expose the cooling liquid to an ambient temperature of the surrounding ambient air.

4. The method of claim 1, wherein re-heating the first extruded bead comprises:
routing the first extruded bead through a heating tube;
as the first extruded bead is routed through the heating tube, routing a flow of hot air into the heating tube to heat the outer surface portions of the first extruded bead; and
maintaining at least one of a volume and a temperature of the flow of hot air into the heating tube that is selected to cause the outer surface portions of the plastics material of the first extruded bead to become molten without causing the plastics material adjacent the first location within the first extruded bead to become molten.

5. The method of claim 4, wherein maintaining at least one of the volume and the temperature of the flow of hot air into the heating tube is based on at least one of a shape of the cross-section of the first extruded bead, a dimension of the cross-section of the first extruded bead, a speed at which the first extruded bead is routed through the heating tube, a length of the heating tube, a shape of a cross-section of the heating tube, and a dimension of the cross-section of the heating tube.

6. The method of claim 4, wherein at least one of a shape of the heating tube and a manner of routing the flow of hot air into the heating tube is selected to cause a pattern of flow of the hot air within the heating tube that urges the first extruded bead toward a center of a cross- section of the heating tube to enable an entirety of the outer surface portions of the plastics material of the first extruded bead to be exposed to the hot air.

7. The method of claim 1, wherein:

a cross-section of the extruded web of plastics material includes a pair of guide formations that extend radially outward from the external surface of the wall of the hose after the extruded web is helically wound about the mandrel or the at least one rotating rod; and the method further comprises using the pair of guide formations to guide the placement of the first extruded bead onto the wall as the first extruded bead is helically wound about the wall to guide an outer surface portion of the plastics material of the first extruded bead into contact with, and into bonding to, a portion of the external surface of the wall between the pair of guide formations.

8. The method of claim 7, wherein:

the first cross-section of the first extruded bead defines a first bonding surface;

the portion of the external surface of the wall between the pair of guide formations comprises a second bonding surface; and guiding the outer surface portion of the plastics material of the first extruded bead into contact with, and into bonding to, the portion of the external surface of the wall between the pair of guide formations comprises guiding the first bonding surface into contact with, and into bonding to, the second bonding surface.

9. The method of claim 8, wherein re-heating the first extruded bead comprises:

routing the first extruded bead past a heating device that outputs a flow of heated air along a path extending from the heating device, with the first extruded bead oriented to place the first bonding surface in the path of the flow of heated air to heat the first bonding surface to a greater degree than any other portion of the exterior of the first extruded bead; and maintaining at least one of a volume and a temperature of the flow of hot air output by the heating device at a level that is selected to cause the first bonding surface to become molten without causing the plastics material adjacent the first location within the first extruded bead to become molten.

10. The method of claim 9, wherein the maintenance of the at least one of the volume and the temperature is based on at least one of a shape of the cross-section of the first extruded bead, a dimension of the cross-section of the first extruded bead, a shape of the first bonding surface, a dimension of the first bonding surface and a speed at which the first extruded bead is routed past the heating device.

11. The method of claim 8, wherein re-heating the first extruded bead comprises:

routing the first extruded bead past a heating device that outputs radiant heat along a path extending from the heating device, with the first extruded bead oriented to place the first bonding surface in the path of the radiant heat to heat the first bonding surface to a greater degree than any other portion of the exterior of the first extruded bead; and maintaining a level of energy of the output of radiant heat output by the heating device at a level that is selected to cause the first bonding surface to become molten without causing the plastics material adjacent the first location within the first extruded bead to become molten.

12. The method of claim 11, wherein the maintenance of the level of energy of the output of radiant heat is based on at least one of a shape of the cross-section of the first extruded bead, a dimension of the cross-section of the first extruded bead, a shape of the first bonding surface, a dimension of the first bonding surface and a speed at which the first extruded bead is routed past the heating device.

13. The method of claim 1, further comprising extruding a second continuous bead of plastics material from a second extruder to have a second cross-section that defines a second lumen at a second location within the second cross-section;

cooling the second extruded bead sufficiently to cool the plastics material adjacent the second location within the second cross-section of the second extruded bead to cause the second lumen to retain its size and shape within the second cross-section;

re-heating the second extruded bead sufficiently to cause outer surface portions of the plastics material of the second extruded bead to become molten; and helically winding the second extruded bead onto and about the external surface of the wall to provide the wall a second support helix.

14. The method of claim 1, further comprising, following the cooling of the first extruded bead and prior to the re-heating of the first bonding surface:

winding a length of the first extruded bead onto a spool to enable the length of the first extruded bead to be stored;

storing the length of the first extruded bead among a plurality of stored lengths of extruded beads that are differentiated from each other by at least one characteristic;

selecting the length of the first extruded bead to be used to form the hose from among the plurality of stored lengths of extruded beads based on the at least one characteristic; and unwinding the length of the first extruded bead from the spool as the length of the first extruded bead is re-heated and then wound onto and about the external surface of the wall of the hose to form hose.

15. The method of claim 14, wherein the at least one characteristic comprises a characteristic selected from a group consisting of:

a shape of a cross-section of a length of extruded bead of the plurality of stored lengths of extruded beads;

a dimension of a cross-section of a length of extruded bead of the plurality of stored lengths of extruded beads;

a shape of a bonding surface of a length of extruded bead of the plurality of stored lengths of extruded beads;

a dimension of a bonding surface of a length of extruded bead of the plurality of stored lengths of extruded beads;

a quantity of electrical wires incorporated into a length of extruded bead of the plurality of stored lengths of extruded beads;

a size of an electrical wire incorporated into a length of extruded bead of the plurality of stored lengths of extruded beads;

a quantity of lumens incorporated into a length of extruded bead of the plurality of stored lengths of extruded beads;

a size of a lumen incorporated into a length of extruded bead of the plurality of stored lengths of extruded beads; and a characteristic of a plastics material from which a length of extruded bead of the plurality of stored lengths of extruded beads is formed.

16. The method of claim 8, wherein one of the first bonding surface and the second bonding surface has a concave shape to correspond to a convex shape of the other of the first bonding surface and the second bonding surface.

* * * * *